US012419946B2

(12) United States Patent
Heaton et al.

(10) Patent No.: US 12,419,946 B2
(45) Date of Patent: Sep. 23, 2025

(54) STABILIZED 9 AND 10 SEGMENTED INFLUENZA VIRUSES AS A VACCINE PLATFORM AND METHODS OF MAKING AND USING SAME

(71) Applicant: Duke University, Durham, NC (US)

(72) Inventors: Nicholas S. Heaton, Durham, NC (US); Alfred Harding, Durham, NC (US); Griffin Haas, New York, NY (US); Alanson Girton, Frederick, MD (US)

(73) Assignee: Duke University, Durham, NC (US)

( * ) Notice: Subject to any disclaimer, the term of this patent is extended or adjusted under 35 U.S.C. 154(b) by 444 days.

(21) Appl. No.: 17/428,921

(22) PCT Filed: Feb. 7, 2020

(86) PCT No.: PCT/US2020/017303
§ 371 (c)(1),
(2) Date: Aug. 5, 2021

(87) PCT Pub. No.: WO2020/163768
PCT Pub. Date: Aug. 13, 2020

(65) Prior Publication Data
US 2023/0060867 A1     Mar. 2, 2023

Related U.S. Application Data

(60) Provisional application No. 62/802,385, filed on Feb. 7, 2019.

(51) Int. Cl.
*A61K 39/145* (2006.01)
*A61K 9/00* (2006.01)
*A61K 39/00* (2006.01)
*A61P 31/16* (2006.01)
*C12N 15/09* (2006.01)

(52) U.S. Cl.
CPC .......... *A61K 39/145* (2013.01); *A61K 9/0043* (2013.01); *A61K 39/0011* (2013.01); *A61P 31/16* (2018.01); *C12N 15/09* (2013.01); *A61K 2039/5156* (2013.01); *A61K 2039/5252* (2013.01)

(58) Field of Classification Search
None
See application file for complete search history.

(56) References Cited

U.S. PATENT DOCUMENTS

| 11,596,683 B2 | 3/2023 | Heaton |
| 2008/0069821 A1 | 3/2008 | Yang |
| 2010/0221349 A1 | 9/2010 | Fuller |
| 2010/0297174 A1 | 11/2010 | Garcia-Sastre et al. |
| 2011/0033859 A1 | 2/2011 | De Fougerolles et al. |
| 2011/0104710 A1 | 5/2011 | Nagata et al. |
| 2012/0141525 A1 | 6/2012 | Jain et al. |
| 2012/0244183 A1 | 9/2012 | Garcia-Sastre |
| 2014/0220075 A1 | 8/2014 | Hoffman et al. |
| 2016/0279227 A1 | 9/2016 | Palese et al. |
| 2018/0008696 A1 | 1/2018 | Palese et al. |
| 2019/0351046 A1 | 11/2019 | Veljkovic et al. |

FOREIGN PATENT DOCUMENTS

| WO | 2009133249 A1 | 11/2009 |
| WO | 2011138032 A2 | 11/2011 |
| WO | 2017177029 A1 | 10/2017 |
| WO | 2019170871 A1 | 9/2019 |
| WO | 2022232298 A1 | 11/2022 |

OTHER PUBLICATIONS

Li J, Arevalo MT, Zeng M. Engineering influenza viral vectors. Bioengineered. 2013;4(1):9-14. Epub Aug. 28, 2012. doi: 10.4161/bioe.21950. PubMed PMID: 22922205; PubMed Central PMCID: PMCPMC3566024.
Li, F. et al. Generation of replication-competent recombinant influenza A viruses carrying a reporter gene harbored in the neuraminidase segment. J Viral 84, 12075-12081, doi: 10.1128/JVI.00046-10 (2010).
Liang Y, Hong Y, Parslow TG. cis-Acting packaging signals in the influenza virus PB1, PB2, and PA genomic RNA segments. J Virol. 2005;79(16):10348-55. doi: 10.1128/jvi.79.16.10348-10355.2005. PubMed PMID: 16051827; PubMed Central PMCID: PMCPMC1182667.
Manicassamy, B., et al. "Analysis of in vivo dynamics of influenza virus infection in mice using a GFP reporter virus." Proceedings of the National Academy of Sciences 107.25 (2010): 11531-11536.
Marsh GA, Hatami R, Palese P. Specific Residues of the Influenza A Virus Hemagglutinin Viral RNA are Important for Efficient Packaging into Budding Virions. Journal of Virology. 2007;81(18):9727-36. doi: 10.1128/jvi.01144-07.
Marshall N, Priyamvada L, Ende Z, Steel J, Lowen AC. Influenza Virus Reassortment Occurs with High Frequency in the Absence of Segment Mismatch. Plos Pathog. 2013;9(6).
Muramoto Y, Takada A, Fujii K, Noda T, Iwatsuki-Horimoto K, Watanabe S, et al. Hierarchy among viral RNA (vRNA) segments in their role in vRNA incorporation into influenza A virions. J Virol. 2006;80(5):2318-25. Epub Feb. 14, 2006. doi: 10.1128/JVI.80.5.2318-2325.2006. PubMed PMID: 16474138; PubMed Central PMCID: PMCPMC1395381.

(Continued)

*Primary Examiner* — Benjamin P Blumel
(74) *Attorney, Agent, or Firm* — Quarles & Brady, LLP

(57) ABSTRACT

The present invention provides a modified influenza A virus (IAV) comprising, consisting of, or consisting essentially of at least one artificial gene segment comprising a duplicated packaging signal, the result of which is a modified IAV that is replication competent and avirulent, and when co-infected with a wild type virus leads to segment exchange and compromises the spread of both viruses as well as methods of making and using same and methods of using the IAVs in the treatment and prevention of influenza-related diseases.

20 Claims, 34 Drawing Sheets
Specification includes a Sequence Listing.

(56) References Cited

OTHER PUBLICATIONS

Nakatsu S, Sagara H, Sakai-Tagawa Y, Sugaya N, Noda T, Kawaoka Y. Complete and Incomplete Genome Packaging of Influenza A and B Viruses. Mbio. 2016;7(5).

Noble S, McLain L, Dimmock NJ. Interfering vaccine: a novel antiviral that converts a potentially virulent infection into one that is subclinical and immunizing. Vaccine. 2004;22(23-24):3018-25. doi: 10.1016/j.vaccine.2004.02.013. PubMed PMID: 15297051.

Noda T, Sagara H, Yen A, Takada A, Kida H, Cheng RH, et al. Architecture of ribonucleoprotein complexes in influenza A virus particles. Nature. 2006;439(7075):490-2. Epub Jan. 27, 2006. doi: 10.1038/nature04378. PubMed PMID: 16437116.

Noda T, Sugita Y, Aoyama K, Hirase A, Kawakami E, Miyazawa A, et al. Three-dimensional analysis of ribonucleoprotein complexes in influenza A virus. Nature Communications. 2012;3:639.

Nogales A, Martinez-Sobrido L. Reverse Genetics Approaches for the Development of Influenza Vaccines. Int J Mol Sci. 2016;18(1). Epub Dec. 28, 2016. doi: 10.3390/ijms18010020. PubMed PMID: 28025504; PubMed Central PMCID: PMCPMC5297655.

Okamoto, S. et al. Intranasal immunization with a formalin-inactivated human influenza A virus whole-virion vaccine alone and intranasal immunization with a split-virion vaccine with mucosal adjuvants show similar levels of cross-protection. Clin Vaccine Immunol 19, 30 979-990, doi:10.1128/CVI.00016-12 (2012).

Pena L, et al. 2013. Influenza viruses with rearranged genomes as live-attenuated vaccines. J Virol 87:5118-5127. https://doi.org/10.1128/JVI.02490-12.

Saira K, Lin X, DePasse JV, Halpin R, Twaddle A, Stockwell T, et al. Sequence analysis of in vivo defective interfering-like RNA of influenza A H1N1 pandemic virus. J Virol. 2013;87(14):8064-74. Epub May 17, 2013. doi: 10.1128/JVI.00240-13. PubMed PMID: 23678180; PubMed Central PMCID: PMCPMC3700204.

Sasaki, S. et al. Comparison of the influenza virus-specific effector and memory B-cell responses to immunization of children and adults with live attenuated or inactivated influenza virus vaccines. J Virol 81, 215-228, doi:10.1128/JVI.01957-06 (2007).

Sekikawa, K. et al. Defects in functional expression of an influenza virus hemagglutinin lacking the signal peptide sequences. Proc Natl Acad Sci US A 80, 3563-3567 (1983).

Shapiro GI, Gurney T, Jr., Krug RM. Influenza virus gene expression: control mechanisms at early and late times of infection and nuclear-cytoplasmic transport of virus-specific RNAs. J Virol. 1987;61(3):764-73. Epub Mar. 1, 1987. PubMed PMID: 3806797; PubMed Central PMCID: PMCPMC254018.

Smith CM, Scott PD, O'Callaghan C, Easton AJ, Dimmock NJ. A Defective Interfering RNA Inhibits Infectious Influenza Virus Replication in Human Respiratory Tract Cells: A Potential New Human Antiviral. Viruses. 2016;8(8). Epub Aug. 25, 2016. doi: 10.3390/v8080237. PubMed PMID: 27556481; PubMed Central PMCID: PMCPMC4997599.

Soema PC, et al. 2015. Current and next generation influenza vaccines: formulation and production strategies. Eur J Pharm Biopharm 94:251-263. https://doi.org/10.1016/j.ejpb.2015.05.023.

Sridhar, S., Brokstad, K. A. & Cox, R. J. Influenza Vaccination Strategies: Comparing Inactivated and Live Attenuated Influenza Vaccines. Vaccines (Basel) 3, 373-389,doi:10.3390/vaccines3020373 (2015).

Sun Y, Jain D, Koziol-White CJ, Genoyer E, Gilbert M, Tapia K, et al. Immunostimulatory Defective Viral Genomes from Respiratory Syncytial Virus Promote a Strong Innate Antiviral Response during Infection in Mice and Humans. PLoS pathogens. 2015;11(9):e1005122. Epub Sep. 4, 2015. doi: 10.1371/journal.ppat.1005122. PubMed PMID: 26336095; PubMed Central PMCID: PMCPMC4559413.

Trombetta CM, Gianchecchi E, Montomoli E. Influenza vaccines: Evaluation of the safety profile. Hum Vaccin Immunother. 2018; 14(3):657-70. Epub Jan. 4, 2018. doi: 10.1080/21645515.2017.1423153. PubMed PMID: 29297746; PubMed Central PMCID: PMCPMC5861790.

Von Magnus P. Incomplete Forms of Influenza Virus. In: Smith KM, Lauffer MA, editors. Advances in Virus Research. 2: Academic Press; 1954. p. 59-79.

Wasik MA, Eichwald L, Genzel Y, Reichl U. Cell culture-based production of defective interfering particles for influenza antiviral therapy. Appl Microbiol Biotechnol. 2018;102(3):1167-77. Epub Dec. 6, 2017. doi: 10.1007/s00253-017-8660-3. PubMed PMID: 29204901; PubMed Central PMCID: PMCPMC5778153.

Williams GD, Townsend D, Wylie KM, Kim PJ, Amarasinghe GK, Kutluay SB, et al. Nucleotide resolution mapping of influenza A virus nucleoprotein-RNA interactions reveals RNA features required for replication. Nature Communications. 2018;9(1):465. doi: 10.1038/s41467-018-02886-w.

Ye, J. et al. Error-prone pcr-based mutagenesis strategy for rapidly generating high-yield influenza vaccine candidates. Virology 482:234-243 (2015).

Yount JS, Kraus TA, Horvath CM, Moran TM, Lopez CB. A novel role for viral-defective interfering particles in enhancing dendritic cell maturation. Journal of immunology (Baltimore, Md : 1950). 2006;177(7):4503-13. Epub Sep. 20, 2006. PubMed PMID: 16982887.

Zhang, R. et al. Clinical, epidemiological and virological characteristics of the first detected human case of avian influenza A(H5N6) virus. Infection, Genetics and Evolution 40:236-242 (2016).

Barik S. New treatments for influenza. BMC Med. 2012;10:104. Epub Sep. 15, 2012. doi: 10.1186/1741-7015-10-104. PubMed PMID: 22973873; PubMed Central PMCID: PMCPMC3523090.

Barman S, Franks J, Turner JC, Yoon SW, Webster RG, Webby RJ. 2015. Egg-adaptive mutations in H3N2v vaccine virus enhance egg-based production without loss of antigenicity or immunogenicity. Vaccine 33:3186-3192. https://doi.org/10.1016/j.vaccine.2015.05.011.

Belongia EA, et al., Marshfield Influenza Study Group. 2009. Effectiveness of inactivated influenza vaccines varied substantially with antigenic match from the 2004-2005 season to the 2006-2007 season. J Infect Dis 199:159-167. https://doi.org/10.1086/595861.

Belshe, R. B. et al. Live attenuated versus inactivated influenza vaccine in infants and young children. N Engl J Med 356, 685-696, doi: 10.1056/NEJMoa065368 (2007).

Breen M, et al. 2016. Replication-competent influenza A viruses expressing reporter genes. Viruses 8:E179. https://doi.org/10.3390/v8070179.

Brooke CB. Population Diversity and Collective Interactions during Influenza Virus Infection. J Virol. 2017;91(22). Epub Sep. 1, 2017. doi: 10.1128/JVI.01164-17. PubMed PMID: 28855247; PubMed Central PMCID: PMCPMC5660503.

Chou YY, Vafabakhsh R, Doganay S, Gao QS, Ha T, Palese P. One influenza virus particle packages eight unique viral RNAs as shown by FISH analysis. P Natl Acad Sci USA. 2012;109(23):9101-6. doi: 10.1073/pnas.1206069109. PubMed PMID: WOS:000304991100066.

Dadonaite B, Barilaite E, Fodor E, Laederach A, Bauer DL. The structure of the influenza A virus genome. bioRxiv.2017:236620. doi: 10.1101/236620.

Davis AR, Hiti AL, Nayak DP. Influenza defective interfering viral RNA is formed by internal deletion of genomic RNA. Proc Natl Acad Sci U S A. 1980;77(1):215-9. Epub Jan. 1, 1980. PubMed PMID: 6928614; PubMed Central PMCID: PMCPMC348239.

Diefenbacher M, Sun J, Brooke CB. The parts are greater than the whole: the role of semi-infectious particles in influenza A virus biology. Curr Opin Virol. 2018;33:42-6. Epub Jul. 28, 2018. doi: 10.1016/j.coviro.2018.07.002. PubMed PMID: 30053722.

Dimmock NJ, Dove BK, Scott PD, Meng B, Taylor I, Cheung L, et al. Cloned defective interfering influenza virus protects ferrets from pandemic 2009 influenza A virus and allows protective immunity to be established. PLoS One. 2012;7(12):e49394. Epub Dec. 20, 2012. doi: 10.1371/journal.pone.0049394. PubMed PMID: 23251341; PubMed Central PMCID: PMCPMC3521014.

Dimmock NJ, Easton AJ. Defective interfering influenza virus RNAs: time to reevaluate their clinical potential as broad-spectrum antivirals? J Virol. 2014;88(10):5217-27. Epub Feb. 28, 2014. doi: 10.1128/JVI.03193-13. PubMed PMID: 24574404; PubMed Central PMCID: PMCPMC4019098.

Dimmock NJ, Rainsford EW, Scott PD, Marriott AC. Influenza virus protecting RNA: an effective prophylactic and therapeutic

(56) References Cited

OTHER PUBLICATIONS antiviral. J Virol. 2008;82(17):8570-8. Epub Jun. 27, 2008. doi: 10.1128/JVI.00743-08. PubMed PMID: 18579602; PubMed Central PMCID: PMCPMC2519629.

Dumm RE, Heaton NS. The Development and Use of Reporter Influenza B Viruses. Viruses-Basel 11, (2019).

Dumm, R. E. et al. Non-lytic clearance of influenza B virus from infected cells preserves epithelial barrier function. Nat Commun 10, 779, doi:10.1038/s41467-019-08617-z (2019).

Eisfeld AJ, Neumann G, Kawaoka Y. At the centre: influenza A virus ribonucleoproteins. Nat Rev Microbiol. 2015;13(1):28-41. Epub Nov. 25, 2014. doi: 10.1038/nrmicro3367. PubMed PMID: 25417656; PubMed Central PMCID: PMCPMC5619696.

Fiege JK, et al. 2015. Investigating influenza A virus infection: tools to track infection and limit tropism. J Virol 89:6167-6170. https://doi.org/10.1128/JVI.00462-15.

Fodor, E., et al. "Rescue of influenza A virus from recombinant DNA." Journal of virology 73.11 (1999): 9679-9682.

Fournier E, Moules V, Essere B, Paillart J-C, Sirbat J-D, Cavalier A, et al. Interaction network linking the human H3N2 influenza A virus genomic RNA segments. Vaccine. 2012;30(51):7359-67.

Fujii K, Fujii Y, Noda T, Muramoto Y, Watanabe T, Takada A, et al. Importance of both the coding and the segment-specific noncoding regions of the influenza A virus NS segment for its efficient incorporation into virions. J Virol. 2005;79(6):3766-74. doi: 10.1128/jvi.79.6.3766-3774.2005. PubMed PMID: 15731270; PubMed Central PMCID: PMCPMC1075679.

Gao, Q., et al. "A nine-segment influenza a virus carrying subtype H1 and H3 hemagglutinins." Journal of virology 84.16 (2010): 8062-8071.

Gao, Q., et al. 2008. A seven-segmented influenza A virus expressing the influenza C virus glycoprotein HEF. J Virol 82:6419-6426. https://doi.org/10.1128/JVI.00514-08.

Gao, Q., et al. 2012. The influenza A virus PB2, PA, NP, and M segments play a pivotal role during genome packaging. J Virol 86:7043-7051. https://doi.org/10.1128/JVI.00662-12.

Gavazzi C, Yver M, Isel C, Smyth RP, Rosa-Calatrava M, Lina B, et al. A functional sequence-specific interaction between influenza A virus genomic RNA segments. Proceedings of the National Academy of Sciences. 2013;110 (41):16604-9. doi: 10.1073/pnas.1314419110.

Gerber M, Isel C, Moules V, Marquet R. Selective packaging of the influenza A genome and consequences for genetic reassortment. Trends in microbiology. 2014;22(8):446-55. Epub May 7, 2014. doi: 10.1016/j.tim.2014.04.001. PubMed PMID: 24798745.

Gog JR, Afonso EDS, Dalton RM, Leclercq I, Tiley L, Elton D, et al. Codon conservation in the influenza A virus genome defines RNA packaging signals. Nucleic Acids Research. 2007;35(6):1897-907. doi: 10.1093/nar/gkm087.

Goto H, Muramoto Y, Noda T, Kawaoka Y. The genome-packaging signal of the influenza A virus genome comprises a genome incorporation signal and a genome-bundling signal. J Virol. 2013;87(21):11316-22. Epub Aug. 9, 2013. doi: 10.1128/JVI.01301-13. PubMed PMID: 23926345; PubMed Central PMCID: PMCPMC3807325.

Haas et al., "Replication competent, 10-segmented influenza viruses as antiviral therapeutics," bioRxiv preprint first posted online Feb. 11, 2019; doi:http://dx.doi.org/10.1101/547059.

Harding AT, Haas GD, Chambers BS, Heaton NS (2019) Influenza viruses that require 10 genomic segments as antiviral therapeutics. PLoS Pathog 15(11): e1008098. https://doi.org/10.1371/journal.ppat.1008098.

Harding AT, Heaton NS. Efforts to Improve the Seasonal Influenza Vaccine. Vaccines (Basel). 2018;6(2). Epub Mar. 31, 2018. doi: 10.3390/vaccines6020019. PubMed PMID: 29601497; PubMed Central PMCID: PMCPMC6027170.

Harding, A. T., et al. "Rationally designed influenza virus vaccines that are antigenically stable during growth in eggs." MBio 8.3 (2017): e00669-17.

Harvey, R., et al. "A promoter mutation in the haemagglutinin segment of influenza A virus generates an effective candidate live attenuated vaccine." Influenza and other respiratory viruses 8.6 (2014): 605-612.

Hatada E, Hasegawa M, Mukaigawa J, Shimizu K, Fukuda R. Control of influenza virus gene expression: quantitative analysis of each viral RNA species in infected cells. J Biochem. 1989;105(4):537-46. Epub Apr. 1, 1989. PubMed PMID: 2760014.

Heaton NS, et al. 2013. In vivo bioluminescent imaging of influenza A virus infection and characterization of novel cross protective monoclonal antibodies. J Virol 87: 8272-8281. https://doi.org/10.1128/JVI.00969-13.

Heaton NS, et al. 2016. Targeting viral proteostasis limits influenza virus, HIV, and dengue virus infection. Immunity 44:46-58. https://doi.org/10.1016/j.immuni.2015.12.017.

Hoffmann, E., et al. "A DNA transfection system for generation of influenza A virus from eight plasmids." Proceedings of the National Academy of Sciences 97.11 (2000): 6108-6113.

Hoffmann, E., et al. "Rescue of influenza B virus from eight plasmids," Proc Natl Acad Sci U S A, 99(17): 11411-11416, 2002.

Hoft, D. F. et al. Live and inactivated influenza vaccines induce similar humoral responses, but only live vaccines induce diverse T-cell responses in young children. J Infect Dis 204, 845-853, doi: 10.1093/infdis/jir436 (2011).

Hutchinson EC, Curran MD, Read EK, Gog JR, Digard P. Mutational analysis of cis-acting RNA signals in segment 7 of influenza A virus. Journal of virology. 2008;82(23):11869-79. Epub Sep. 2024. doi: 10.1128/JVI.01634-08. PubMed PMID: 18815307.

Hutchinson EC, von Kirchbach JC, Gog JR, Digard P. Genome packaging in influenza A virus. J Gen Virol. 2010;91(Pt 2):313-28. Epub Dec. 4, 2009. doi: 10.1099/vir.0.017608-0. PubMed PMID: 19955561.

International Search Report and Written Opinion for International Patent Application No. PCT/US2020/017303 dated Apr. 27, 2020.

Jacobs NT, Onuoha NO, Anita A, Anita R, Steel J, Lowen AC. Incomplete influenza A virus genomes are abundant but readily complemented during spatially structured viral spread. bioRxiv. 2019. Epub Jan. 23, 2019. doi: https://doi.org/10.1101/529065.

Jenkins MR, Webby R, Doherty PC, Turner SJ. Addition of a prominent epitope affects influenza a virus-specific CD8 (+) T cell immunodominance hierarchies when antigen is limiting. Journal of Immunology 177, 2917-2925 (2006).

Jin H, Chen Z. 2014. Production of live attenuated influenza vaccines against seasonal and potential pandemic influenza viruses. Curr Opin Virol 6:34-39. https://doi.org/10.1016/j.coviro.2014.02.008.

Kummer S, Flottmann M, Schwanhausser B, Sieben C, Veit M, Selbach M, et al. Alteration of protein levels during influenza virus H1N1 infection in host cells: a proteomic survey of host and virus reveals differential dynamics. PLoS One. 2014;9(4):e94257. Epub Apr. 11, 2014. doi: 10.1371/journal.pone.0094257. PubMed PMID: 24718678; PubMed Central PMCID: PMCPMC3981805.

Lamb RA, Choppin PW. The Gene Structure and Replication of Influenza Virus. Annual Review of Biochemistry. 1983;52(1):467-506. doi: 10.1146/annurev.bi.52.070183.002343. PubMed PMID: 6351727.

Laske T, Heldt FS, Hoffmann H, Frensing T, Reichl U. Modeling the intracellular replication of influenza A virus in the presence of defective interfering RNAs. Virus Research. 2016;213:90-9. doi: https://doi.org/10.1016/j.virusres.2015.11.016.

Lee N, Le Sage V, Nanni AV, Snyder DJ, Cooper VS, Lakdawala SS. Genome-wide analysis of influenza viral RNA and nucleoprotein association. Nucleic acids research. 2017;45(15):8968-77. Epub Jul. 2007. doi: 10.1093/nar/gkx584. PubMed PMID: 28911100.

Li D, Lott WB, Lowry K, Jones A, Thu HM, Aaskov J. Defective interfering viral particles in acute dengue infections. PLoS One. 2011;6(4):e19447. Epub May 12, 2011. doi: 10.1371/journal.pone.0019447. PubMed PMID: 21559384; PubMed Central PMCID: PMCPMC3084866.

Eckert N, Wrensch F, Gärtner S, Palanisamy N, Goedecke U, Jäger N, et al. Influenza A Virus Encoding Secreted Gaussia Luciferase as Useful Tool to Analyze Viral Replication and its Inhibition by

(56) References Cited

OTHER PUBLICATIONS

Antiviral Compounds and Cellular Proteins. PLoS One [Internet]. 2014. [cited Nov. 24, 2020];9(5).

Engelhardt OG. Many ways to make an influenza virus—review of influenza virus reverse genetics methods. Influenza Other Respir Viruses. May 2013;7(3):249-56.

Karlsson EA, Meliopoulos VA, Savage C, Livingston B, Mehle A, Schultz-Cherry S. Visualizing real-time influenza virus infection, transmission and protection in ferrets. Nat Commun [Internet]. Mar. 6, 2015. [cited Nov. 24, 2020];6:6378.

Masic A., et al. "An eight-segment swine influenza virus harboring H1 and H3 hemagglutinins is attenuated and protective against H1N1 and H3N2 subtypes in pigs." Journal of virology 87.18 (2013): 10114-10125.

Pan W, Dong Z, Li F, Meng W, Feng L, Niu X, et al.. Visualizing influenza virus infection in living mice. Nat Commun [Internet]. 2013. [cited Nov. 13, 2020];4:2369.

Reuther P, Gopfert K, Dudek AH, Heiner M, Herold S, Schwemmle M. Generation of a variety of stable Influenza A reporter viruses by genetic engineering of the NS gene segment. Sci Rep [Internet]. Sep. 12, 2015. [cited Nov. 23, 2020];5(1):11346.

Rossman JS, Lamb RA. 2011. Influenza virus assembly and budding. Virology 411:229-36.

Sereinig S, et al. Influenza virus NS vectors expressing the mycobacterium tuberculosis ESAT-6 protein induce CD4+ Th1 immune response and protect animals against tuberculosis challenge. Clin Vaccine Immunol 13, 898-904 (2006).

Spronken M. I., et al. "Optimisations and challenges involved in the creation of various bioluminescent and fluorescent influenza A virus strains for in vitro and in vivo applications." PLoS One 10.8 (2015).

Sutton TC, Obadan A, Lavigne J, Chen H, Li W, Perez DR. Genome rearrangement of influenza virus for anti-viral drug screening. Virus Res [Internet]. Aug. 30, 2014. [cited Nov. 24, 2020];189:14-23.

Takizawa N, Momose F, Morikawa Y, Nomoto A. 2016. Influenza A Virus Hemagglutinin is Required for the Assembly of Viral Components Including Bundled vRNPs at the Lipid Raft. Viruses-Basel 8.

Yan D, Weisshaar M, Lamb K, Chung HK, Lin MZ, Plemper RK. Replication-Competent Influenza Virus and Respiratory Syncytial Virus Luciferase Reporter Strains Engineered for Co-Infections Identify Antiviral Compounds in Combination Screens. Biochemistry [Internet]. Sep. 15, 2015. [cited Nov. 24, 2020];54(36):5589-604.

FIG. 2 (continued)

E  9s PB1 mCherry Survival

F  9s PB2 sfGFP LD50 Survival

G  Cage Preparation → D -1; WT PR8 Lethal Challenge → D 0; 9s Virus Administered; Body Weight Monitored; D +14

I  9s PB1 DI / WT PR8 Coinfection Weight Loss

J  9s PB1 DI / WT PR8 Coinfection Survival

10s: PB2 sfGFP, PB1 mCherry
(Duplicated PA and NA PS)

FIG. 6

Assembly and viral propagation in the absence of 10s viruses

FIG. 6 (continued)

Assembly and viral propagation is disrupted by 10s viruses

A.  NA-PB1-NA

B.  PB1-mCherry-PB1

C.  NP-PB2-NP

D. PB2-sfGFP-PB2

E. NS-HA-NS

F. HA-sfGFP-HA

G. PA-PB2-PA

H. HA-M1-HA

I. M-zsGreen|M2-M

J. NA-NS1-NA

K. NS-mCherry|NEP-NS

STABILIZED 9 AND 10 SEGMENTED INFLUENZA VIRUSES AS A VACCINE PLATFORM AND METHODS OF MAKING AND USING SAME

CROSS-REFERENCE TO RELATED APPLICATIONS

This patent application is a national stage filing under 35 U.S.C. § 371 of International Patent Application no. PCT/US2020/017303, filed Feb. 7, 2020, which claims the benefit of priority of U.S. Provisional Patent Application No. 62/802,385, filed Feb. 7, 2019, which is incorporated herein by reference in its entirety.

STATEMENT REGARDING FEDERALLY SPONSORED RESEARCH

This invention was made with government support under Grant Number HHSN272201400005 awarded by the National Institutes of Health. The government has certain rights in this invention.

SEQUENCE LISTING

A Sequence Listing accompanies this application and is submitted as an ASCII text file of the sequence listing named "155554_00613_ST25.txt" which is 33,295 bytes in size and was created on Sep. 17, 2021. The sequence listing is electronically submitted via EFS-Web with the application and is incorporated herein by reference in its entirety.

INTRODUCTION

Influenza virus infections represent a substantial global burden on human health. Each year, it is estimated that influenza viruses cause up to 5 million severe infections globally, resulting in up to 645,000 mortalities [1, 2]. In 2018, patient care and productivity loss due to influenza infection cost an estimated $11.2 billion in the U.S. alone [3]. Influenza A viruses (IAVs), the major contributor to total human influenza disease, possess a segmented genome consisting of eight discrete, negative-sense viral RNAs (vRNAs) [4]. Each of the eight vRNA segments consist of terminal 5' and 3' untranslated regions (UTRs) flanking an internal open-reading frame that encodes that one or maximally two viral proteins [5]. The UTRs, as well as the proximal portions of the coding regions, form "packaging signals" that are both necessary and sufficient for incorporation of each vRNA into progeny virions [6-11]. Although the underlying mechanisms that control packaging are incompletely understood, it has been hypothesized that segments may potentially interact with one another via vRNA-vRNA interactions across genome segments [12-16]. In any case, experimental evidence has supported the theory that non-random genome packaging controls the proper incorporation of segments into progeny virions [17, 18]. The segmented nature of the viral genome, and at least some intra-strain conserved regions of the packaging signals, allows for reassortment to occur between strains that have coinfected the same host cell [19]. The process of genetic reassortment, termed antigenic shift, can lead to the development of novel strains and can cause pandemic outbreaks, such as the one that occurred in 2009 with the H1N1 pandemic "swine" flu virus [20].

Currently, the primary measure used to control IAV spread is prophylactic immunization. However, due to rapid viral accumulation of point mutations, a process known as antigenic drift, vaccination can have limited efficacy. In these cases, healthcare providers must turn to therapeutic options for treating influenza disease. Adamantanes, matrix ion channel inhibitors, were the first IAV therapeutics developed, and were approved for clinical use in 1966 [21]. However, shortly after their deployment, it was apparent that IAVs were capable of developing rapid resistance to matrix ion channel inhibitors [22, 23]. High levels of resistance to adamantanes are now widespread in H1, H3, H5, H7, H9, and H17 subtype influenza A viruses, retiring the use of matrix ion channel inhibitors in treating influenza disease [22, 24]. Neuraminidase inhibitors, such as oseltamivir, are now the most commonly used IAV therapeutic [25]. As with adamantanes, this class of antiviral suffers from resistance as well [26-28]. In fact, greater than 90 percent of 2008-2009 pre-pandemic, globally circulating H1N1s were reported as having resistance to oseltamivir alone [21]. While these levels have decreased since the arrival of the 2009 pandemic-clade H1N1s, resistant strains are still isolated each year, highlighting the risk of widespread evolution of antiviral resistance [29, 30]. Finally, an mRNA cap snatching inhibitor, Baloxavir, was recently FDA-approved [31, 32], and the rate at which viral resistance may be acquired is currently unknown.

One strategy for treating influenza is to mimic the activity of naturally occurring viral particles that harbor defective genomes. These defective interfering particles have the ability to interfere with productive viral assembly, preventing the spread of influenza viruses across the respiratory tract. Further, given the manner in which they target influenza segment packaging, a conserved feature of all influenza A viruses, resistance to this therapeutic strategy is unlikely, as it would be difficult or even impossible for the viruses to generate functional escape variants through acquisition of random mutations.

Defective viral particles are not unique to influenza viruses, and research has demonstrated their formation and importance for a number of RNA viruses [34-36]. For influenza viruses, defective interfering particles, or DIPs, are replication-incompetent virions that frequently harbor one or more viral gene segments with a significant truncation of the open reading frame (ORF) of that segment [37]. Deletions can occur spontaneously during the replication stage of the viral lifecycle when the viral RNA-dependent RNA polymerase skips over a portion of the ORF, and generates a large deletion in that segment while still maintaining the 5' and 3' packaging signals necessary for gene segment incorporation [38]. If this partially deleted segment is packaged into nascent virions, virus particles are produced that are capable of infecting a host cell, but are then unable to produce subsequent viable progeny due to the lack of the protein normally encoded by the defective vRNA segment [39]. While DIPs are themselves replication incompetent, due to their defective segments, they can be successfully propagated during coinfection with a "helper" wild-type IAV. Although it was believed that such coinfections are relatively uncommon, recent work has shown that co-infection may actually help facilitate productive virus replication [40]. If DIP coinfection does occur, the defective segment(s) of the interfering particle are replicated more quickly than their wild-type counterparts due to their significantly smaller size [33, 41]. This rapid replication allows the defective segment(s) to outcompete the wild-type vRNAs for genome packaging, interfering with the ability of replication-competent wild type IAV progeny to be generated and spread.

Due to the incomplete efficacy of these therapeutics, as well as emerging viral resistance, additional antiviral therapeutics are in in various stages of development [31]. Accordingly, there remains a need in the art for alternative therapeutic approaches for treating influenza.

SUMMARY

The present invention provides a construct or set of constructs for making a modified influenza A virus, modified influenza virus particles, vaccines and methods of making and using the same.

In some aspects, the disclosure provides a polynucleotide construct or set of constructs comprising one or more of the following domains: (i) a first domain comprising a 5' packaging signal and a 3' packaging signal of the polymerase acid (PA) segment and encoding polymerase basic subunit 2 (PB2); (ii) a second domain comprising a heterologous segment comprising a 5' packaging signal and 3' packaging signal of PB2 and a heterologous polynucleotide sequence; (iii) a third domain comprising a 5' packaging signal and a 3' packaging signal of polymerase acid (PA) and encoding polymerase basic subunit 1 (PB1); or (iv) a fourth domain comprising a heterologous segment comprising a 5' packaging signal of PB1 and a heterologous polynucleotide sequence; wherein the polynucleotide construct or set of constructs comprises: (a) the first domain (i) and the second domain (ii), (b) the third domain (iii) and the fourth domain (iv), or (c) the first, second, third and fourth domains (i), (ii), (iii) and (iv); and wherein the construct or set of constructs encodes at least two segments of a replication competent modified influenza A virus having at least nine gene segments.

In another aspect, the disclosure provides a polynucleotide construct or set of constructs comprising one or more of the following domains: (v) a fifth domain comprising a 5' packaging signal and a 3' packaging signal of neuraminidase (NA) and encoding PB1; (iv) the fourth domain comprising a heterologous segment comprising a 5' packaging signal of PB1 and a heterologous polynucleotide sequence; (vi) a sixth domain comprising a 5' packaging signal and a 3' packaging signal of NA and encoding (ii) the second domain comprising a heterologous segment comprising a 5' packaging signal and 3' packaging signal of PB2 and a heterologous polynucleotide sequence; wherein the polynucleotide construct or set of constructs comprises: (a) the fifth domain and the fourth domain, (b) the sixth domain and the second domain (iv), or (c) the second, fourth, fifth and sixth domains; and wherein the construct or set of constructs encodes at least two segments of a replication competent modified influenza A virus having at least nine gene segments.

In another aspect, the disclosure provides a polynucleotide construct or set of constructs including (d) the first, second and fourth domain (i), (ii), (iv) and (v) a fifth domain comprising a 5' packaging signal and a 3' packaging signal of neuraminidase (NA) and encoding PB1; or (e) the second, third and fourth domain (ii) (iii), (iv) and (vi) a sixth domain comprising a 5' packaging signal and a 3' packaging signal of NA and encoding PB2. In a further aspect, the construct or set of constructs comprises constructs encoding wild-type viral segments for PA, HA, NP, NA, M and NS and optionally for PB1 or optionally for PB2 such that the construct or set of constructs includes all the genes needed for viral replication in a cell.

In another aspect, the disclosure provides a cell comprising the polynucleotide construct or set of constructs described herein capable of producing modified influenza A virus (IAV). In one aspect, the cell comprises the polynucleotide construct or set of constructs of: the first, second, third and fourth domains; the first, second, fourth and fifth domains; the second, third, fourth and sixth domains or the second, fourth, fifth and sixth domains, and wherein the cell produces replication competent IAV with 10 gene segments when combined with viral segments for PA, HA, NP, NA, M and NS.

In yet another aspect, the disclosure provides a modified influenza A virus (IAV) comprising at least nine gene segments produced by the cell described herein.

In another aspect, the disclosure provides a modified IAV comprising at least 10 gene segments, wherein at least four gene segments are the reverse complement of the sequence of the first, second, third and fourth domains; the first, second, fourth and fifth domains; the second, third, fourth and sixth domains or the second, fourth, fifth and sixth domains described herein. In some aspects, the modified IAV is replication competent and avirulent.

In another aspect, the disclosure provides a vaccine comprising a modified IAV described herein.

In yet another aspect, the disclosure provides a method of making a modified influenza A virus (IAV), or vaccine thereof, the method comprising: inserting the polynucleotide construct or set of constructs as described herein into a cell in culture; and collecting the modified IAV from media from the cell culture. Modified IAV made by this method are also provided.

In a further aspect, the disclosure provides a method of reducing virulence of a wild-type influenza A strain in a subject, the method comprising: (a) administering the modified IAV or the vaccine described herein in an amount effective to reduce the virulence of the wild-type influenza A strain by at least 10 fold in the subject.

In another aspect, the disclosure provides a method of interfering with packaging of wild-type influenza A virus by increasing the non-viable virions produced by a cell, the method comprising: contacting the cell infected with a wild-type influenza A virus with modified IAV described herein in an amount effective to increase the amount of non-viable virions produced by the cell by at least $10^2$, preferably at least $10^3$.

In yet another aspect, the disclosure provides a method of treating or reducing at least one symptom caused by an influenza virus infection in a subject comprising administering to the subject a therapeutically effective amount of modified IAV described herein.

In yet a further aspect, the disclosure provides a method of immunizing a subject to at least one pathogen, the method comprising: administering the vaccine described herein to elicit an immune response.

In a further aspect, the disclosure provides a kit comprising the polynucleotide construct or set of constructs described herein and instructions.

BRIEF DESCRIPTION OF THE DRAWINGS

FIG. 6. Model for 10s viral interference with WT viral spread. WT PR8 virus (grey) replication produces viable progeny (top panel). 10s virus (orange) coinfection with WT PR8 virus facilitates incomplete genome packaging, resulting in disrupted WT PR8 replication and the production of non-viable progeny (lower panel). The black curved lines indicate packaging signal equivalence between the WT and 10s virus genomic segments, and incorporation of any of the four red-boxed segments into WT virions will generate non-viable genomic reassortants.

DETAILED DESCRIPTION

Figure 1:
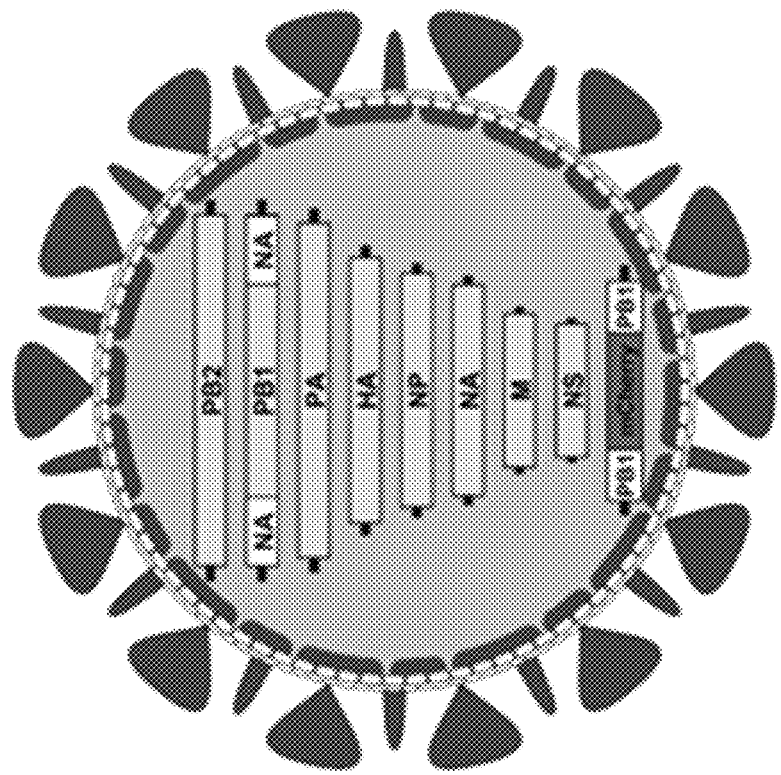
FIG. 1. 9-Segmented fluorescent viruses generate proportionally more defective interfering particles than WT IAV. (A and B) Genome design of the 9s PB1 mCherry virus (A) and the 9s PB2 sfGFP virus (B). (C) Growth curve of 9s PB1 mCherry (■), 9s PB2 sfGFP (Δ), and WT PR8 (●) viruses titered in MDCK cells 0, 24, 48, and 72 hours post-infection in 10-day old embryonated chicken eggs. (D) Fluorescent microscopy images of 9s PB1 mCherry, 9s PB2 sfGFP, or WT PR8 virus-infected MDCK cells at 0, 6, 12, and 24 hours post-infection; nuclei were stained blue using DAPI staining and the scale bar represents 100 micrometers. (E) Endpoint titer 72 hours post-infection in 10-day old embryonated chicken eggs of the 9-segmented fluorescent viruses as compared to WT PR8 virus. (F) HA assay 72 hours post infection in 10-day old embryonated chicken eggs of the 9-segmented fluorescent viruses as compared to WT PR8 virus. (G) The "DI Units" of the 9-segmented fluorescent viruses as compared to that of WT PR8 virus, calculated by dividing respective normalized HA units by normalized endpoint titer. For all graphs, * represents a p-value of ≤0.05 and ** represents a p-value of ≤0.001.
Figure 1:
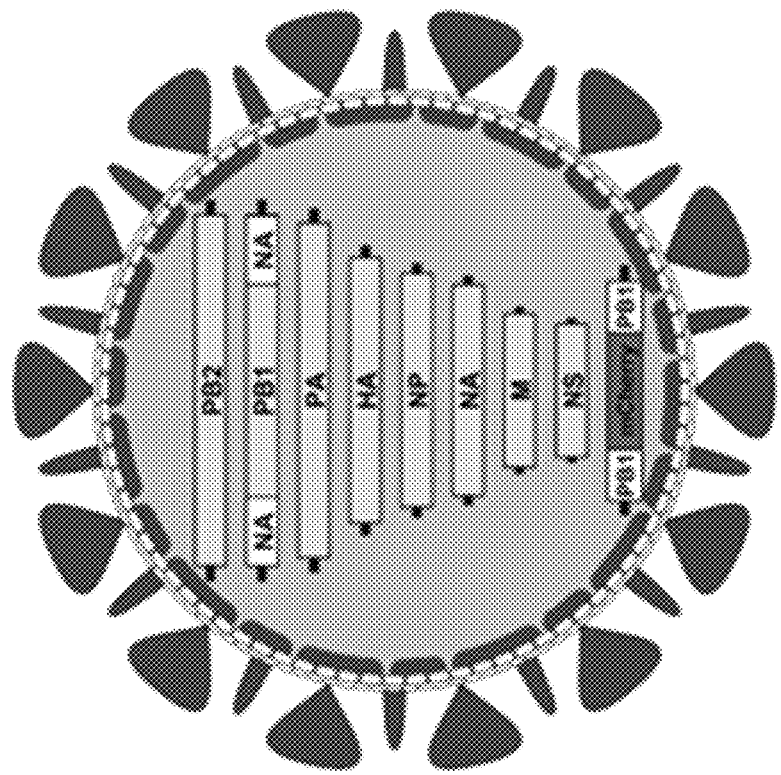
Figure 1:
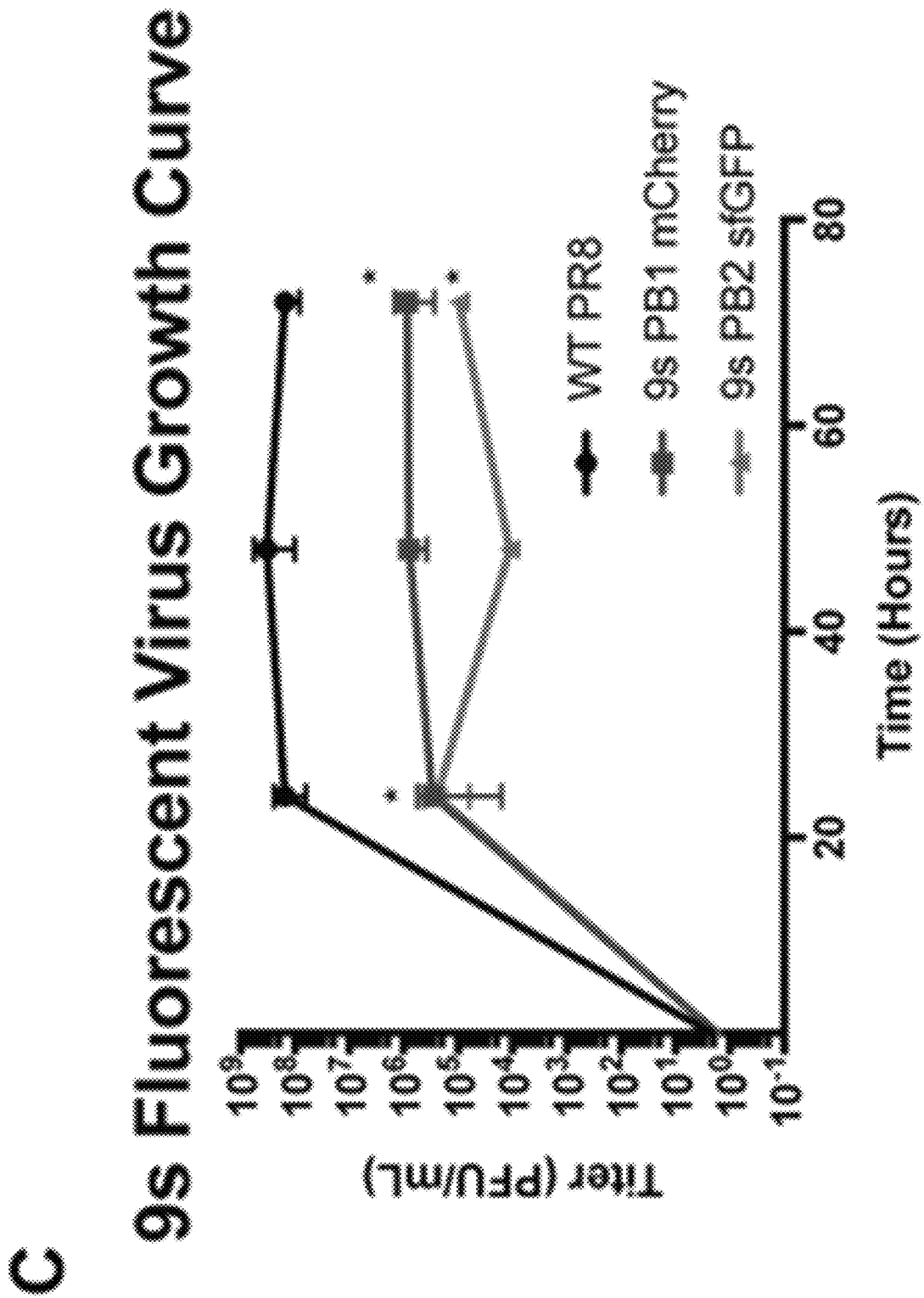
Figure 1:
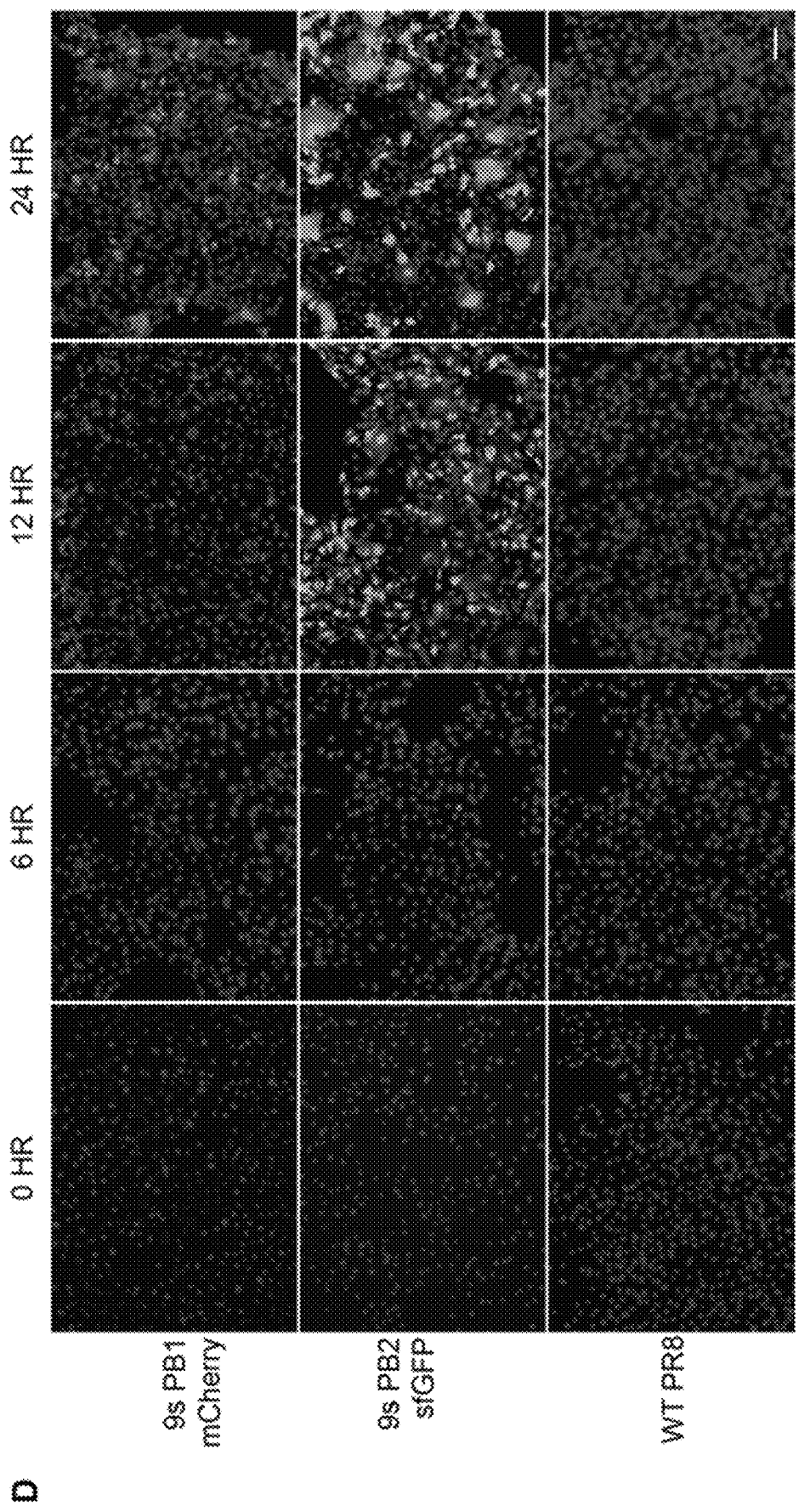
Figure 1:
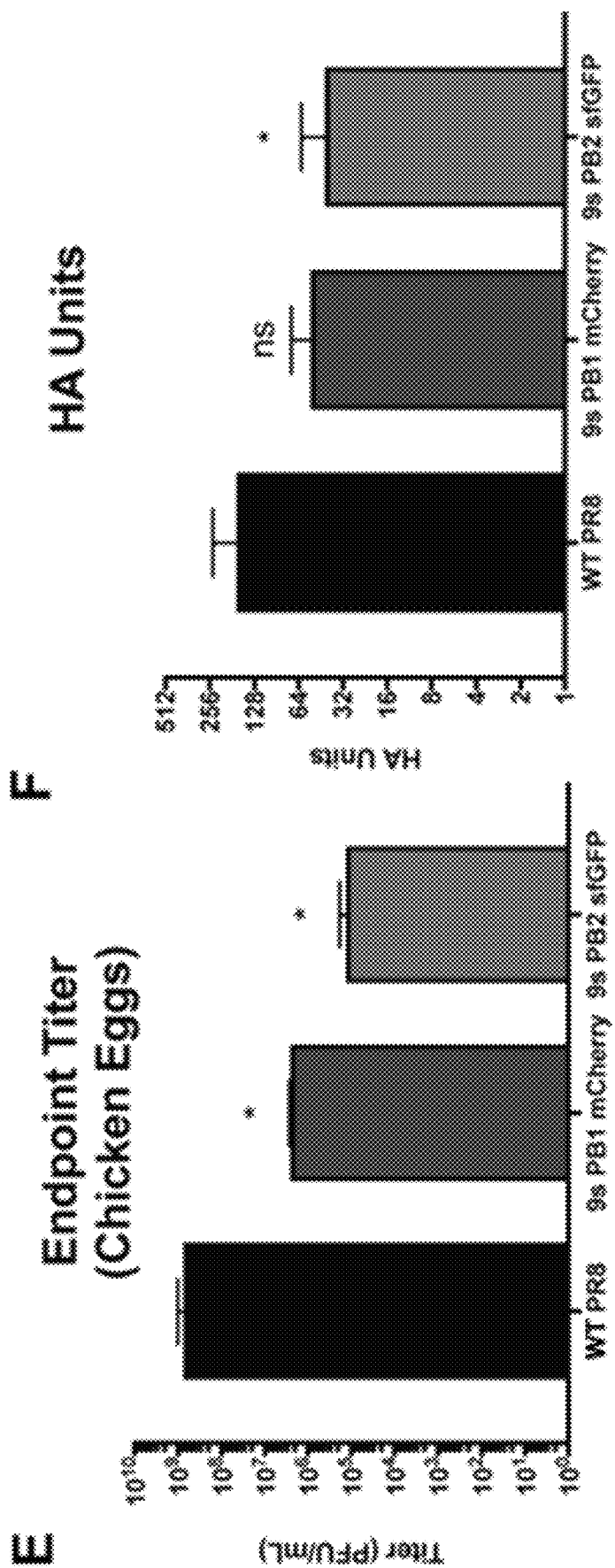
Figure 1:
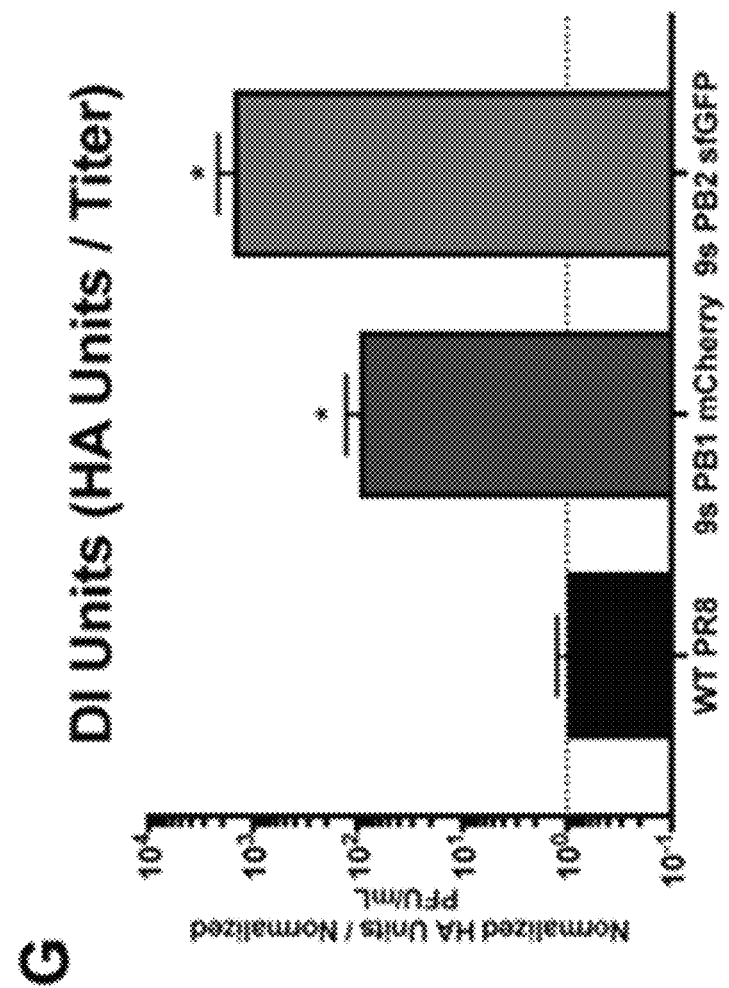

The disruptive effect of DIPs has long garnered attention as a potential influenza antiviral [42-44]. Studies have shown that laboratory produced DIPs can be used prophylactically and therapeutically to protect mice from a lethal wild type IAV infection [45]. Further, coinfection of this same DI virus design with a dose of the 2009 H1N1 pandemic virus was found to reduce the symptoms of disease in a ferret model [46]. This DI system has also been shown to be effective in vitro in human respiratory tract cell lines [47]. Despite these advances, options for generating DIPs have been limited. Initially, DIPs were synthesized via high multiplicity passaging, which not only generates diverse DI populations with varying efficacy, but also contains wild-type IAVs that must be inactivated by UV irradiation [48, 49]. Reverse genetic cloning has offered a means through which to generate populations of specific DIP genotypes, however this method requires the use of helper viruses for the proliferation of the DIPs, again necessitating a subsequent UV inactivation. Cell culture optimization for production of DIPs is under way, but is currently only able to produce high yield batches consisting of mixed DI populations with varying efficacy, or purer populations with a significantly reduced yield that are not sufficient for therapeutic use [50].

The present invention overcomes the prior drawbacks of DIPS by providing modified influenza A virus (IAV) particles that are self-replicating (i.e. replication competent) and avirulent, and are able to interfere with wildtype influenza infection reducing virulence, morbidity and mortality from influenza virus. The modified IAV therapeutically mimic the inhibitory activity of DIPs but are replication competent and do not require a helper virus for propagation in culture. These modified IAV are live-attenuated virus which harbor artificial genome segments that get packaged and propagated along with the virus. The modified virus was designed such that the artificial segments would not interfere with its own replication, allowing it to be amplified in isolation. However, when co-infection with a wild-type virus occurs, cross-packaging of genome segments between the two viruses leads to the production of an increase in non-viable particles and thus results in the halt, lowering or slowing of viral spread. In the Examples, the inventors demonstrate that this interference is mechanistically distinct from naturally occurring defective particles but was able to target the same viral process and was surprisingly able to rescue animals exposed to an otherwise lethal viral infection. Due to the mechanism of action of interfering with wildtype virus propagation and spread, these modified IAV are able to be used for diverse strains of influenza A including anti-viral resistant strains and strains that there is no vaccine to as of yet, as the mechanism of action doesn't depend on the virus encoding a specific influenza antigen to reduce or halt influenza virus spread. Thus, this viral-based approach represents a cost effective and scalable method to generate effective anti-influenza therapeutics when vaccines or anti-viral drugs become ineffective due to acquisition of viral resistance mutations.

Constructs, Modified Virus and Compositions

Wildtype influenza strains carry their genome across eight, negative sense RNA segments. These eight segments are required to be packaged during viral assembly to result in an infectious viral particle. As well known in the art, influenza viruses include eight ribonucleoprotein (RNP) complexes composed of single-stranded negative RNA viral gene segments (PB2, PB1, PA, HA, NP, NA, M, and NS) encapsidated by the viral nucleoprotein—NP. Surrounding the RNP complex is a matrix protein capsid and a lipid bilayer containing the two viral glycoproteins—HA and NA. Reverse genetics systems have been established using polynucleotide constructs that allow for generation of recombinant influenza viruses in tissue culture system. Using such systems, the present invention provides construct(s) that produce modified IAVs having 9 or 10 segment genomes (i.e. one or two extra artificial gene segments, also referred to as 9S or 10S for "9 segments" or "10 segments") by duplicating a packaging signal on two influenza gene segments. These 9 and 10 segment modified IAVs are replication competent and avirulent. These artificial genome segments are capable of acting as "decoy" segments that, when packaged by wild-type (WT) viruses, lead to the increased production of non-infectious viral particles. As shown in the Examples, despite 9-segmented and 10-segmented viruses being able to replicate and spread in vivo, these genomic modifications render the viruses avirulent. The inventors surprisingly found that only NA or PA duplicated packaging signals allowed for replication competent IAVs that were able to package a $9^{th}$ or $10^{th}$ gene segment, as the other packaging signals did not allow for replication competent IAVs (see, e.g., Table 1). Excitingly, as demonstrated in the examples, administration of 10-segmented viruses, both prophylactically and therapeutically, was able to rescue animals from normally lethally influenza virus infections. These modified IAVs can be used as a strain-independent mechanism to slow the kinetics of productive viral spread and therefore limit viral disease.

In order to produce modified IAVs, the influenza (−)RNA gene segments and necessary proteins are produced in tissue culture by expression from one or more polynucleotide constructs (e.g., plasmids) encoding the influenza gene segments to assemble influenza A virus particles. Intracellular reconstitution of the whole set of ribonucleoproteins (RNPs) consisting of viral RNAs, influenza virus polymerase subunits and nucleoprotein via introduction (e.g., transfection) of the construct or set of constructs results in the generation of a modified IAV. The present invention provides the construct or set of constructs, cells and methods of producing such modified IAV particles. Modified IAVs and compositions and vaccines comprising them are also described herein.

In one embodiment, the present invention provides a polynucleotide construct or set of constructs that encodes at least two segments of a replication competent modified influenza A virus (IAV), the IAV having at least nine gene segments (e.g., 9 or 10 segments). This construct or set of constructs can be introduced into a cell to produce replication competent IAVs of the present invention.

In one embodiment, the polynucleotide construct or set of constructs comprises one or more of the following domains:

(i) a first domain comprising a 5' packaging signal and a 3' packaging signal of the polymerase acid (PA) segment and encoding polymerase basic subunit 2 (PB2);

(ii) a second domain comprising a heterologous segment comprising a 5' packaging signal and 3' packaging signal of PB2 and a heterologous polynucleotide sequence;

(iii) a third domain comprising a 5' packaging signal and a 3' packaging signal of polymerase acid (PA) and encoding polymerase basic subunit 1 (PB1); or (iv) a fourth domain comprising a heterologous segment comprising a 5' packaging signal of PB1 and a heterologous polynucleotide sequence;

wherein the polynucleotide construct or set of constructs comprises: (a) the first domain (i) and the second domain (ii), (b) the third domain (iii) and the fourth domain (iv), or (c) the first, second, third and fourth domains (i), (ii), (iii) and (iv); and wherein the construct or set of constructs encodes at least two segments of a replication competent modified influenza A virus having at least nine gene segments.

In one embodiment, the construct or set of constructs comprises the first (i) domain comprising a 5' packaging signal and a 3' packaging signal of the polymerase acid (PA) segment and encoding polymerase basic subunit 2 (PB2); and the second (ii) domain comprising a heterologous segment comprising a 5' packaging signal and 3' packaging signal of PB2 and a heterologous polynucleotide sequence, to produce at least a 9 segment modified IAV. In another embodiment, the construct or set of constructs comprises the third (iii) domain and the fourth (iv) domain providing two segments that can be used to produce a 9 segment (9S) replication competent modified IAV.

In another embodiment, the construct or set of constructs encodes four segments that can be used to produce a 10 segment (10S) replication competent modified IAV, specifically the construct or set of constructs comprise the first domain, the second domain, the third domain and the fourth domain. As described more below, two domains, second domain (ii) and fourth domain (iv), both comprise a heterologous polynucleotide sequence. This heterologous polynucleotide sequence of the second and fourth domain can comprise the same heterologous polynucleotide sequence or can comprise two different heterologous polynucleotide sequences.

In another embodiment, the disclosure provides a polynucleotide construct or set of constructs comprising one or more of the following domains:
(v) a fifth domain comprising a 5' packaging signal and a 3' packaging signal of neuraminidase (NA) and encoding PB1;
(iv) the fourth domain comprising a heterologous segment comprising a 5' packaging signal of PB1 and a heterologous polynucleotide sequence;
(vi) a sixth domain comprising a 5' packaging signal and a 3' packaging signal of NA and encoding PB2; or
(ii). the second domain comprising a heterologous segment comprising a 5' packaging signal and 3' packaging signal of PB2 and a heterologous polynucleotide sequence;
wherein the polynucleotide construct or set of constructs comprises: (a) the fifth domain and the fourth domain, (b) the sixth domain and the second domain (iv), or (c) the second, fourth, fifth and sixth domains; and wherein the construct or set of constructs encodes at least two segments of a replication competent modified influenza A virus having at least nine gene segments.

In one particular example, the disclosure provides a polynucleotide construct or set of constructs comprising the second (ii) domain comprising a heterologous segment comprising a 5' packaging signal and 3' packaging signal of PB2 and a heterologous polynucleotide sequence; the fourth (iv) domain comprising a heterologous segment comprising a 5' packaging signal of PB1 and a heterologous polynucleotide sequence; the fifth (v) domain comprising a 5' packaging signal and a 3' packaging signal of neuraminidase (NA) and encoding PB1; and the sixth (vi) domain comprising a 5' packaging signal and a 3' packaging signal of NA and encoding PB2; wherein the construct or set of constructs encodes at least four segments of a replication competent 10-segment (10S) modified influenza A virus.

In another embodiment, the disclosure provides a polynucleotide construct or set of constructs comprises (d) the first, second and fourth domain (i), (ii), (iv) and (v) a fifth domain comprising a 5' packaging signal and a 3' packaging signal of neuraminidase (NA) and encoding PB1 where the construct or set of constructs encodes at least four segments of a replication competent 10S modified influenza A virus. This example provides for a ten segment (10S) modified IAV virus in which four artificial segments (two comprising a non-native packaging signal with the viral open reading frames (i.e. first and fifth domain) and with viral packaging signals without viral open reading frames (i.e. domain (ii) and domain (iv)) are incorporated. Two of the artificial segments comprise the 5' and 3' packaging signal from either NA or PA with the viral open reading frame of either PB1 or PB2. The other two artificial segments (second and fourth domain) comprise a heterologous sequence. The heterologous polynucleotide sequence of the second and fourth domain can comprise the same heterologous polynucleotide sequence or each domain can comprise a different heterologous polynucleotide sequences, as described in more detail below.

Another embodiment provides a polynucleotide construct or set of constructs comprising (e) the second, third and fourth domain (ii) (iii), (iv) and (vi) a sixth domain comprising a 5' packaging signal and a 3' packaging signal of NA and encoding PB2. This embodiment provides for the constructs to produce a 10S modified IAV comprising two artificial segments (encoded by domains (ii) and (iv)) which each comprise a heterologous polynucleotide sequence.

This heterologous polynucleotide sequence of the second and fourth domain can have the same heterologous polynucleotide sequence or can comprise two different heterologous polynucleotide sequences. Suitable heterologous sequences are defined below.

The construct or set of constructs described herein further comprise an additional construct(s) encoding the wild-type segments necessary to provide all 8 segments of the wild-type influenza genome (polymerase basic subunit 2 (PB2, segment 1), polymerase basic subunit 1 (PB1, segment 2), polymerase acidic subunit (PA, segment 3), hemagglutinin (HA, segment 4), nucleoprotein (NP, segment 5,), neuraminidase (NA, segment 6), matrix (M, segment 7), and nonstructural protein (NS, segment 8). For example, the construct or set of constructs described above can further comprising construct(s) encoding wild-type viral segments for PA, HA, NP, NA, M and NS. These segments and methods of reverse engineering to produce such segments within constructs are known in the art, for example, as demonstrated in the examples below. In some embodiments, an additional PB1 or PB2 construct can also be included in construct or sets of constructs in which PB1 or PB2 is not already encoded by one of the domains.

In a construct or set of constructs described above in which PB1 is not encoded by one of the domains, the construct or set of constructs will further comprise a PB1 construct encoding wild-type viral segment for PB1. This is in addition to the construct(s) encoding wild-type viral segments for PA, HA, NP, NA, M and NS. For example, in a construct or set of constructs comprising first domain (i) and second (ii) domain, or comprising second domain (ii) and sixth (vi) domain described above, an additional PB-1 construct can also be included, in addition to the construct(s) encoding wild-type viral segments for PA, HA, NP, NA, M and NS.

In a construct or set of constructs described above in which none of the domains encode PB2, the construct or set of constructs further comprise a PB2 construct encoding wild-type viral segment for PB2. Again, this is in addition to the construct(s) encoding wild-type viral segments for PA, HA, NP, NA, M and NS. For example, in a construct or set of constructs comprising the third (iii) domain and fourth (iv) domain or fourth (iv) domain and fifth (v) domain described above, an additional PB2 construct can be included, in addition to construct(s) encoding wild-type viral segments for PA, HA, NP, NA, M and NS.

The term "construct" refers to a polynucleotide sequence capable of transporting another nucleic acid to which it has been linked and expressing the gene encoded within the nucleic acid sequence. The polynucleotide sequence is usually under the control of a transcriptional promoter allowing the regulation of the transcription of said polynucleotide in a host cell. Said polynucleotide can also be linked to appropriate control sequences allowing the regulation of its translation in a host cell. Suitable constructs are known in the art, and include, for example, vectors and plasmids. A set of constructs includes one or more constructs. A "plasmid" refers to a circular double stranded DNA loop into which additional DNA segments may be ligated, specifically exogenous DNA segments. Certain constructs are capable of autonomous replication in a host cell into which they are introduced (e.g., bacterial vectors having a bacterial origin of replication and episomal mammalian vectors). Other constructs can be integrated into the genome of a host cell upon introduction into the host cell, and thereby are replicated along with the host genome. Moreover, certain constructs are capable of directing the expression of exogenous genes to which they are operatively linked. Such constructs or vectors are referred to herein as "recombinant expression vectors" (or simply, "expression vectors"). In general, expression vectors in recombinant DNA techniques are often in the form of plasmids. Other constructs such as BACs, YACs or others may also be used and are well known to those of skill in the art. Vectors can also include additional selectable marker genes and other genetic elements known in the art. A plasmid or vector can preferably transduce, transform or infect a cell, thereby causing the cell to express the mRNA and proteins encoded by the plasmid.

In a preferred embodiment, the construct or set of constructs is a plasmid or a set of plasmids. It has been shown that recombinant influenza A virus can be made by reverse genetics by using one or more plasmids to produce infectious IAV from a host cell. It is contemplated that multiple plasmids may be used, as described in the examples and prior art (e.g., Heaton N S, Leyva-Grado V H, Tan G S, Eggink D, Hai R, Palese P. In vivo bioluminescent imaging of influenza a virus infection and characterization of novel cross-protective monoclonal antibodies. J Virol. 2013; 87(15):8272-81. Epub 2013 May 24. doi: 10.1128/JVI.00969-13. PubMed PMID: 23698304; PubMed Central PMCID: PMCPMC3719835), or a single plasmid (for example, as described in "One-Plasmid System To Generate Influenza Virus in Cultured Chicken Cells for Potential Use in Influenza Vaccine", Xiangmin Zhang, Wei Kong, Shamaila Ashraf, Roy Curtiss III, Journal of Virology August 2009, 83 (18) 9296-9303; DOI: 10.1128/JVI.00781-09).

Suitable plasmids may include, without limitation, plasmids typically used to rescue influenza viruses in cells such as plasmids used in the 12 plasmid and 8 plasmid reverse genetic systems well-known in the art. See, e.g., Neumann et al., PNAS 96:9345-9350 (1999); Fodor et al., J. Virol. 73:9679-9682 (1999); Hoffmann et al., PNAS 97:6108-6113 (2000); Hoffmann et al., Virology 267:310-317 (2000). Preferably, the plasmid is a pDZ plasmid used with 8 plasmid reverse genetic systems. The pDZ plasmid is an ambisense plasmid including a human RNA polymerase I promoter and a terminator sequence that controls the expression of the negative sense viral RNA. In an opposite orientation to this viral RNA unit, the viral proteins from the same viral RNA genes are expressed using a chicken β-actin promoter and polyA sequence. Plasmids for encoding the eight segments of influenza viruses are known in the art. For example, eight pDZ plasmids are available that each encode influenza virus segment 1 (PB2), segment 2 (PB1), segment 3 (PA), segment 4 (HA), segment 5 (NP), segment 6 (NA), segment 7 (M), and segment 8 (NS). Other construct systems are contemplated to be within the scope of the present invention.

The term "packaging signal" refer to the cis-acting sequence or sequences within the influenza genome segment required to ensure that each influenza virion has a full complement of the influenza genome (i.e., all 8 segments). Influenza virus packaging signal(s) have been identified for each influenza A virus segment. See, e.g., Gao et al. J. Virol. 86:7043-7051 (2012). As demonstrated in the examples, it was surprisingly found that only the 5' and 3' packaging signals from NA or PA are able to be duplicated within the virion and allow for replication competent IAVs that were able to package a $9^{th}$ or $10^{th}$ gene segment. 5' and 3' packaging signals refers to the pair of packaging signals found at the 3' and 5' end of the wildtype virus genome. The packaging signal of PA used in the present invention comprises 5' packaging signal of PA, SEQ ID NO:1, or portion thereof, and 3' packaging signal of PA, SEQ ID NO:2, or portion thereof. The packaging signal of NA used in the present invention comprises 5' packaging signal of NA, SEQ ID NO:3, or portion thereof, and the 3' packaging signal of NA, SEQ ID NO:4, or portion thereof. For example, the modified IAV described herein may include, without limitation, SEQ ID NO:1 and SEQ ID NO:2 or SEQ ID NO:3 and SEQ ID NO:4.

As described in the examples, incorporating the packaging signal of NA or PA into the genome segment encoding for PB1 and/or PB2, allows for the use of the PB1 and/or PB2 packaging signal to incorporate an artificial genome segment into the IAV (e.g., to create modified 9S or 10S IAV). Thus, the 5' and 3' packaging signals of PB1 and/or PB2 are used to incorporate one or two artificial genome segments into the modified IAV, wherein the artificial genome segments comprise a heterologous polynucleotide sequence. This is exemplified in the second (ii) or fourth (iv) domain described above.

Suitably, in some embodiments of the construct or set of constructs described herein, the 5' packaging signal of PB1 in the domains is SEQ ID NO:5, the 3' packaging signal of PB1 in the domains is SEQ ID NO:6; the 5' packaging signal of PB2 in the domains is SEQ ID NO:7; the 3' packaging signal of PB2 in the domains is SEQ ID NO:8, or a combination thereof.

In examples in which the NA or PA packaging signal is incorporated into the domain encoding for PB2 (e.g., the first domain or the sixth domain), the polynucleotide encoding PB2 is mutated to disable the native packaging signal of PB2 within the open reading frame of PB2 polynucleotide sequence. Suitable methods for mutating the polynucleotide sequence are known in the art, and the sequence is mutated at a sufficient number of nucleotides in order to disable the PB2 packaging signal. For example, in some examples, the polynucleotide sequence encoding PB2 is SEQ ID NO:16 (from (A/Puerto Rico/8/1934)) or SEQ ID NO:17 (from (A/Wyoming/03/2003)). Both SEQ ID NO:16 and SEQ ID NO:17 have non-functional PB2 signal sequences. Polynucleotide sequences encoding PB2 from other influenza A stains are also contemplated to be able to be adapted for use in the present invention.

In examples in which the NA or PA packaging signal is incorporated into the domain encoding for PB1 (e.g., the third domain or the fifth domain), the polynucleotide sequence encoding PB1 is mutated to disable the native packaging signal of PB1 within the open reading frame of PB1. The sequence is mutated at a sufficient number of nucleotides in order to disable the PB2 packaging signal, and methods of mutating are known in the art. For example, in one example, a suitable polynucleotide sequence encoding PB1 is SEQ ID NO:15 which has a non-functional PB1 packaging signal. Polynucleotide sequences encoding PB1 from other influenza A stains are also contemplated to be able to be adapted for use in the present invention.

The term "heterologous polynucleotide sequence" as used herein (for example, as in the second domain, the fourth domain or both) refers to an engineered (e.g., not native) polynucleotide sequence engineered and not found in native influenza virus in nature. Specifically, the heterologous polynucleotide sequence is engineered between the 5' and 3' packaging signals of the second or fourth domain. The heterologous polynucleotide sequence may contain only a few linker nucleotides sufficient to link the 5' packaging signal to the 3' packaging signal. In other embodiments, the heterologous polynucleotide sequence comprising one or more multiple cloning sites (MCS). Suitable multiple cloning sites are known in the art. In another non-limiting example, the heterologous polynucleotide sequence can contain one or more enzyme restriction sites. These MCS or enzyme restriction sites may be used to clone in one or more polynucleotides encoding a protein of interest. In another nonlimiting example, the heterologous polynucleotide sequence of the second domain, the fourth domain, or both comprises a polynucleotide sequence encoding for a polypeptide of interest. In some examples, the second domain encodes for a different polypeptide of interest than the fourth domain.

The encoded polypeptide of interest may be any polypeptide having an open reading frame sequence of about 3.5 kbp or less, preferably 3.2 kbp or less. Suitable polypeptides of interest include, but are not limited to, for example, markers, a heterologous antigen, or immunomodulatory protein. The polypeptide of interest may also be a fusion protein of two or more different proteins or heterologous antigens. In some examples, wherein the modified IAV has 10 segments (10S), each additional artificial gene segment not encoding a viral ORF can independently encode a polypeptide of interest, e.g., a marker, a heterologous antigen or immunomodulatory protein. In another example, the modified IAV may contain two or more proteins of interest within a single artificial gene segment, wherein the two or more antigens that are linked by a linker (e.g., detachable linker), as described in publication Harding A T, Heaton B E, Dumm R E, Heaton N S. Rationally Designed Influenza Virus Vaccines That Are Antigenically Stable during Growth in Eggs. mBio. 2017 Jun. 6, Vol. 8 no. 3 e00669-17 doi: 10.1128/mBio.00669-17. PMID: 28588131, the contents of which are incorporated by reference in its entirety. In other words, a single artificial gene segment may encode two or more heterologous antigens, for example, two or more influenza antigens (e.g., NA or HA from a different strain, etc.). Modified IAV can have one or two artificial gene segment comprising a polynucleotide sequence encoding the heterologous antigen or immunomodulatory protein flanked on the 3'-end and 5'-end by a PB1 or PB2 packaging signal described above.

The term heterologous antigen as used herein is used to describe an antigen of interest that is not native to the IAV parental influenza strain from which the IAV was derived. In some examples, the heterologous antigen may be to a different antigen, for example, an antigen from a pathogenic organism, a tumor antigen, a disease-associated antigen, among others. In some examples, the antigen may be an influenza antigen that is to a different influenza strain (i.e., as shown in the examples, an antigen from an influenza strain that is not Wild-type A/Puerto Rico/8/1934 (PR8), e.g., neuraminidase (NA) or hemagglutinin (HA)). In other examples, the heterologous antigen may be an antigen to another pathogenic organism which are known in the art, for example, a virus, fungus or parasite. Pathogenic organisms and associate antigens (e.g., proteins from the pathogen) are known in the art. For example, pathogenic viruses include, but are not limited to, for example, smallpox, mumps, measles, chickenpox, ebola, HIV, rubella, hepatitis, papilloma, among others, and may be from the following viral families: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, Togaviridae, among others. Pathogenic bacteria are known in the art and include, but are not limited to, for example, gram positive and gram negative bacteria, such as, for example, *Salmonella, Listeria* and *E. coli, Streptococcus, Pseudomonas, Shigella, Campylobacter*, among others, and can belong to the bacteria species including, but not limited to, *Bacillus* (e.g, *Bacillus anthracis*), *Bartonella, Bordetella* (e.g. *Bordetella pertussis*), *Borrelia, Brucella, Campylobacter, Chlamydia, Chlamydophilia, Clostridium, Corynebacterium, Enterococcus, Escherichia, Francisella, Haemophilus, Helcibater, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio, Yersinia*, among others. Suitable pathogenic fungus include, but are not limited to, for example, the following species: *Candida, Aspergillus, Cryptococcus, Histoplasma, Pneumocystis, Stachybotrys*, among others. Pathogenic parasites are known in the art and include, for example, protozoa (e.g., plasmodium), helminths (e.g., schistosomiasis), Acanthamoebiasis, Babesiosis, Balantidiasis, Blastocystosis, Coccidia, *Entamoeba histolytica, Giardia, Cystoisospora belli, Leishmania, Rhinosporidium seeberi, Toxoplasma gondii, Trichomonas vaginalis*, worms, among others. One skilled in the art would be able to determine acceptable pathogenic antigens to be used for vaccination in the present technology.

In some embodiments, the artificial gene segment encodes an immunomodulatory protein. Immunomodulatory protein as used herein refers to proteins that when express can enhance, induce or amplify an immune response. For example, an immunomodulatory protein can be included within the modified IAV described herein, and such can help to enhance the immune response to the influenza virus or a heterologous antigen being carried by the modified IAV. Suitable immunomodulatory proteins are known to one skilled in the art. Suitable immunomodulatory proteins include, but are not limited to, for example, adjuvants (e.g., bacterial proteins), checkpoint inhibitors (e.g, PD-1 agonists, PDL-1 agonists, CTLA-4 agonists, etc), cytokines, toll-like receptor (TLR) agonists, adjuvants (including, for example bacterial proteins (e.g., flagellin)), and the like.

In other embodiments, the artificial gene segment encodes a marker. Suitable markers are known in the art and include, but are not limited to, for example, detectable markers, tags, and the like. Suitable detectable markers include luminescent proteins, fluorescent proteins (e.g., green fluorescent protein (GFP), red fluorescent protein (RFP), mCherry, Cerulean Fluorescent Protein, Cyan and Yellow Super Fluorescent Protein, blue fluorescent protein, among others).

As used herein, a "polypeptide: or "protein" or "peptide" are used interchangeably to refer to a polymer of amino acids. A "protein" as contemplated herein typically comprises a polymer of naturally occurring amino acids (e.g., alanine, argininine, asparagine, aspartic acid, cysteine, glutamine, glutamic acid, glycine, histidine, isoleucine, leucine, lysine, methionine, phenylalaninine, proline, serine, threonine, typotophan, tyrosine, and valine).

The polynucleotides provided herein may be prepared by methods available to those skilled in the art. Notably, each of the polynucleotides claimed are recombinant molecules and as such do not occur in nature. Generally, the nomenclature used herein and the laboratory procedures utilized in the present invention include molecular, biochemical, and recombinant DNA techniques that are well known and commonly employed in the art. Standard techniques available to those skilled in the art may be used for cloning, DNA and RNA isolation, amplification, purification and making of recombinant modified IAV. Such techniques are thoroughly explained in the literature.

The heterologous segment of the second domain and the fourth domain are a size capable of being packaged into the influenza virion. The engineered artificial influenza gene segments can comprise no insert (i.e., just contain the 5' and 3' packaging signals linked by a linking non-encoding nucleotide or polynucleotide) or an insert up to about 3.3 kbp, which results in an gene segment of less than 3.5 kbp. Thus, each heterologous segment (e.g., second domain and fourth domain) may be from about 300 base pairs (bp) to about 3.5 kbp, alternatively from about 800 bp to about 2400 bp. Ranges and sizes of artificial gene segments within these ranges are contemplated and considered within the scope of the present invention.

Suitably, in some embodiments, to increase the likelihood of the additional heterologous (artificial) gene segments being packaged into virions, the artificial gene segment domains (e.g., second domain, fourth domain or both) may be designed to have a length commensurate with the length of one of the eight wild-type gene segments (e.g., about 2300-2350 bp (segment 2(PB1)/segment 1(PB2)), about 2100-2300 bp, e.g., 2233 bp (segment 3 (PA)), about 1700-1800 bp, e.g., 1778 bp (segment 4 (HA)), about 1500-1600 bp, e.g., 156 bp (segment 5 (NP)), about 1400-1450 bp, e.g., 1413 bp (segment 6 (NA)), about 1000 bp-1100 bp, e.g., 1027 bp (segment 7 (M)), or about 850-900 bp, e.g., 890 bp (segment 8 (NS))). However, the present invention is not limited by any of these sizes or ranges and contemplates any suitable artificial gene segment that is able to be packaged into virions for the practice of the current technology Suitable construct or set of constructs are described in the examples. In some example, the first the first domain is SEQ ID NO:12 or SEQ ID NO:14; and/or the fifth domain is SEQ ID NO:11.

The disclosure also provides a cell comprising the polynucleotide construct or set of constructs described herein capable of producing modified influenza A virus (IAV). In one embodiment, the cell comprises the polynucleotide construct or set of constructs of: the first, second, third and fourth domains; the first, second, fourth and fifth domains; the second, third, fourth and sixth domains or the second, fourth, fifth and sixth domains, and wherein the cell produces replication competent IAV with 10 gene segments. The cell may further comprise one or more constructs comprising wild-type viral segments for PA, HA, NP, NA, M and NS, and in some examples, wild-type viral segments for PB1 and/or PB2. Suitable cells in accordance with the present invention include eukaryotic cells. Suitable eukaryotic cells include, without limitation, mammalian cells or chicken cells. The cell may be a cell in culture or may be an embryonated chicken egg. Suitable mammalian cells include, without limitation, a MDCK cell, A549 cell, a 5 CHO cell, a HEK293 cell, a HEK293T cell, a HeLa cell, a NS0 cell, a Sp2/0 cell, a COS cell, a BK cell, a NIH3T3 cell, a FRhL-2 cell, a MRC-5 cell, a WI-38 cell, a CEF cell, a CEK cell, a DF-1 cell, or a Vero cell. Modified IAVs produced by the cells described herein are also provided.

In another aspect, the present invention relates to methods for producing a replication competent modified influenza A virus. A method of making a modified influenza A virus (IAV), or vaccine thereof, the method comprising: (i) inserting the polynucleotide construct or set of constructs described herein into a cell in culture; and (iii) collecting the modified IAV from media from the cell culture. Modified IAV made by the method are also contemplated.

As used herein, "inserting" describes a process by which exogenous polynucleotides (e.g., DNA or RNA) or viral particles are introduced into a recipient cell. Methods of introducing the disclosed polynucleotides, plasmids, and plasmid compositions into a cell are known in the art and may include, without limitation, transfection, transformation, and microinjection methods. Transformation or transfection may occur under natural or artificial conditions according to various methods well known in the art, and may rely on any known method for the insertion of foreign nucleic acid sequences into a host cell. The method for transformation or transfection is selected based on the type of host cell being transformed and may include, without limitation, lipofection, bacteriophage or viral infection, electroporation, heat shock, and particle bombardment. Microinjection of polynucleotides may also be used to introduce the disclosed polynucleotides, plasmids, and plasmid compositions into cells. In some embodiments, the disclosed polynucleotides, plasmids, and plasmid compositions may be introduced into cells using a lipofectamine-based transfection.

The methods for producing influenza virus may also further include additional steps used in harvesting the influenza virus from the cell. In embodiments including cells in culture, the methods may further include harvesting the supernatant of the culture by, for example, centrifugation or pipetting. In embodiments where the cell is an embryonated chicken egg, the methods may further include harvesting the allantoic fluid from the embryonated chicken egg.

The disclosure further provides a modified influenza A virus (IAV) comprising at least nine gene segments produced by methods known in the art using the polynucleotide construct or set of constructs, and cells, described herein. In another embodiment, the disclosure provides modified IAV comprising at least 10 gene segments, wherein at least four gene segments are the reverse complement of the sequence of the first, second, third and fourth domains; the first, second, fourth and fifth domains; the second, third, fourth and sixth domains or the second, fourth, fifth and sixth domains described above. The modified IAV is replication competent. In some embodiments, the modified IAV is avirulent.

Replication competent, as used herein, refers to virus particles that are able to self-replicate and do not need a helper virus or expression of a required protein by the cell in order to infect a cell. The term replication competent may be used interchangeably with the terms self-replicating or self-propagating.

The modified IAVs described herein are avirulent. The term "avirulent" as used herein describes a virus that has at least a 10 fold, preferably a 100 fold, most preferably a 1000 fold reduction in morbidity and mortality as compared to a wildtype strain. As demonstrated in the examples, avirulence can be determined using a mouse model, wherein the avirulent strain is unable to induce signs of mortality or morbidity after administering 10×, 100×, and/or 1000× more infectious viral particles than the parental strains lethal dose. For example, the modified IAVs described herein were tested against parental strain (Wild-type A/Puerto Rico/8/1934) in mice, the parental strain having a lethal dose of approximately 10 pfu. The modified 10S IAV described herein unable to induce any signs of morbidity or mortality after administering $10^4$ pfu, i.e., avirulent.

The modified IAV is replication competent and avirulent, and when co-infected with a wild-type virus leads to segment exchange and reduction of the spread of both viruses (i.e., the modified virus and the wildtype virus). The modified IAV can be used for treatment of influenza virus infections, the result of use of the modified IAV is a reduction in viral virulence, morbidity and mortality due to virus infection. Further, the modified IAVs, being avirulent, can also be used as a vaccine carrying not only antigens for influenza but heterologous antigens, including pathogenic antigens or tumor antigens, or as a vaccine that carries and additional immunostimulatory protein that enhances the immune response.

The term "artificial gene segment" refers to an influenza genomic viral segment that is not native to the influenza virus (i.e., engineered) and is capable of being packaged into influenza virions. Two such artificial segment comprises the 5' and 3' packaging signal or portion thereof from either PB1 or PB2 (from a wild-type strain) and a heterologous polynucleotide sequence. Two other artificial segments comprise the 5' and 3' packaging signal or portion thereof from NA or PA and encode the sequence of PB1 or PB2, as described in more detail herein (preferably wherein the packaging signal of PB1 or PB2 has been disabled). Thus, in some embodiments, the modified IAV contain at least two artificial gene segments, and in some embodiments the modified IAV contain four artificial gene segments.

Another aspect of the present invention provides a vaccine or vaccine composition comprising, consisting of, or consisting essentially of a modified IAV as provided herein, in some examples, an influenza vaccine. In some embodiments, the vaccine further comprises a pharmaceutically acceptable carrier. In some embodiments, the vaccine further comprises an adjuvant. The vaccine may be live-attenuated modified IAV or may be heat-inactivated IAV. Preferably, the vaccine is a live modified IAV vaccine as the live modified IAV is able interfere with packaging of wildtype IAV and to reduce the virulence of a wildtype strain within a subject.

In one embodiment, the vaccine further comprises a pharmaceutically acceptable carrier. Any pharmaceutically acceptable carrier may be used with the present invention. The term "pharmaceutically acceptable" means approved by a regulatory agency of the Federal or a state government or listed in the U.S. The term "carrier" refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration. The particular formulation may also depend on whether the virus is live or inactivated. The vaccine compositions may include a pharmaceutical carrier, excipient, or diluent, which are nontoxic to the cell or subject being exposed thereto at the dosages and concentrations employed. Often a pharmaceutical diluent is in an aqueous pH buffered solution. Examples of pharmaceutical carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant. The vaccine compositions described herein may include adjuvants to increase immunogenicity of the composition. The adjuvant may be any of the currently FDA-licensed adjuvants for influenza vaccine usage including, without limitation, aluminum salt (alum) and the squalene oil-in-water emulsion systems MF59 (Wadman 2005 (Novartis)) and AS03 (GlaxoSmithKline).

In some embodiments, these vaccine compositions comprise one or more of a mineral adjuvant, gel-based adjuvant, tensoactive agent, bacterial product, oil emulsion, particulated adjuvant, fusion protein, and lipopeptide. Mineral salt adjuvants include aluminum adjuvants, salts of calcium (e.g. calcium phosphate), iron and zirconium. Gel-based adjuvants include aluminum gel-based adjuvants and acemannan. Tensoactive agents include Quil A, saponin derived from an aqueous extract from the bark of *Quillaja saponaria*; saponins, tensoactive glycosides containing a hydrophobic nucleus of triterpenoid structure with carbohydrate chains linked to the nucleus, and QS-21. Bacterial products include cell wall peptidoglycan or lipopolysaccharide of Gramnegative bacteria (e.g. from *Mycobacterium* spp., *Corynebacterium parvum, C. granulosum, Bordetella pertussis* and *Neisseria meningitidis*), N-acetyl muramyl-L-alanyl-D-isoglutamine (MDP), different compounds derived from MDP (e.g. threonyl-MDP), lipopolysaccharides (LPS) (e.g. from the cell wall of Gram-negative bacteria), trehalose dimycolate 5 (TDM), cholera toxin or other bacterial toxins, and DNA containing CpG motifs. Oil emulsions include FIA, Montanide, Adjuvant 65, Lipovant, the montanide family of oil-based adjuvants, and various liposomes. Among particulated and polymeric systems, poly (DL-lactide-coglycolide) microspheres have been extensively studied and find use herein. Notably, several of the delivery particles noted above may also act as adjuvants. In some embodiments, the vaccine compositions further include cytokines (e.g. IFN-γ, granulocyte-macrophage colony stimulating factor (GM-CSF) IL-2, or IL-12) or immunostimulatory molecules such as FasL, CD40 ligand or a toll-like receptor agonist, or carbohydrate adjuvants (e.g. inulin-derived adjuvants, such as, gamma inulin, algammulin, and polysaccharides based on glucose and mannose, such as glucans, dextrans, lentinans, glucomannans and galactomannans).

In some embodiments, adjuvant formulations are useful in the present invention and include alum salts in combination with other adjuvants such as Lipid A, algammulin, immunostimulatory complexes (ISCOMS), which are virus like particles of 30-40 nm and dodecahedric structure, composed of Quil A, lipids, and cholesterol.

In some embodiments, the additional adjuvants are described in Jennings et al. Adjuvants and Delivery Systems for Viral Vaccines-Mechanisms and Potential. In: Brown F, Haaheim L R, (eds). Modulation of the Immune Response to Vaccine Antigens. Dev. Biol. Stand, Vol. 92. Basel: Karger 1998; 19-28 and/or Sayers et al. J Biomed Biotechnol. 2012; 2012: 831486, and/or Petrovsky and Aguilar, Immunology and Cell Biology (2004) 82, 488-496. In some embodiments, the adjuvant is an aluminum gel or salt, such as aluminum hydroxide, aluminum phosphate, and potassium aluminum sulfate, AS04 (which is composed of aluminum salt and MPL), and ALHYDROGEL. In some embodiments, the aluminum gel or salt is a formulation or mixture with any of the additional adjuvants described herein.

In some embodiments, pharmaceutical compositions include oil-in-water emulsion formulations, saponin adjuvants, ovalbumin, Freunds Adjuvant, cytokines, and/or chitosans. Illustrative compositions comprise one or more of the following. (1) ovalbumin (e.g. ENDOFIT); (2) oil-in-water emulsion formulations, with or without other specific 5 immunostimulating agents, such as: (a) MF59 (PCT Publ. No. WO 90/14837), which may contain 5% Squalene, 0.5% Tween 80, and 0.5% Span 85 (optionally containing various amounts of MTP-PE) formulated into submicron particles, (b) SAF, containing 10% Squalane, 0.4% Tween 80, 5% pluronic-blocked polymer L121, and thr-MDP either microfluidized into a submicron emulsion or vortexed to generate a larger particle size emulsion, (c) RIBI adjuvant system (RAS), (RIBI IMMUNOCHEM, Hamilton, MO.) containing 2% Squalene, 0.2% Tween 80, and, optionally, one or more bacterial cell wall components from the group of monophosphorylipid A (MPL), trehalose dimycolate (TDM), and cell wall skeleton (CWS), including MPL+ CWS (DETOX™); and (d) ADDAVAX (Invitrogen); (3) saponin adjuvants, such as STIMULON (Cambridge Bioscience, Worcester, Mass.); (4) Complete Freunds Adjuvant (CFA) and Incomplete Freunds Adjuvant (IFA); (5) cytokines, such as interleukins (by way of non-limiting example, IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; (6) chitosans and other derivatives of chitin or poly-N-acetyl-D-glucosamine in which the greater proportion of the N-acetyl groups have been removed through hydrolysis; and (7) other substances that act as immunostimulating agents to enhance the effectiveness of the composition, e.g., monophosphoryl lipid A.

In other embodiments, adjuvants include a flagellin-based agent, an aluminium salt or gel, a pattern recognition receptors (PRR) agonist, CpG ODNs and imidazoquinolines. In some embodiments, adjuvants include a TLR agonist (e.g. TLR1, and/or TLR2, and/or TLR3, and/or TLR4, and/or TLR5, and/or TLR6, and/or TLR7, and/or TLR8, and/or TLR9, and/or TLR10, and/or TLR11, and/or TLR12, and/or TLR13), a nucleotide-binding oligomerization domain (NOD) agonist, a stimulator of interferon genes (STING) ligand, or related agent.

Suitably, the vaccines compositions described herein are capable of eliciting an immune response to an influenza virus or polypeptide thereof when administered to a subject. In another aspect, the vaccine described herein are capable of eliciting an immune response to a heterologous antigen encoded by the modified IAV. In some embodiments, the compositions or vaccine compositions including modified influenza viruses described herein may include at least $10^6$ pfu/mL, $10^7$ pfu/mL, $10^8$ pfu/mL, or $10^9$ pfu/mL.

Advantageously, the modified IAV or vaccine may be introduced into the lungs by any suitable route. Pulmonary administration can also be employed, using e.g. an inhaler or nebulizer or formulate it with an aerosolizing agent. Methods of introduction include but are not limited to intradermal, intramuscular, intraperitoneal, intravenous, intranasal, epidural or oral routes. Introduction by intranasal routes is preferred. In one embodiment, the vaccine is formulated for intramuscular delivery. In another embodiment, the vaccine is formulated for intranasal delivery.

In yet another embodiment, the disclosure provides a method of reducing virulence of a wild-type influenza A strain in a subject, the method comprising: (a) administering one or more modified IAV described herein or the vaccine described herein in an amount effective to reduce the virulence of the wild-type influenza A strain by at least 10 fold in a subject infected with or exposed to the wildtype Influenza A strain. In another embodiment, the virulence is reduced at least 100 fold. In a further embodiment, the virulence is reduced at least 1000 fold. The subject may be a subject having been diagnosed with influenza A. In other embodiments, the subject may be a subject exposed to influenza A virus. In another embodiment, the subject may be a subject showing one or more symptom of influenza A virus.

In yet another embodiment, the disclosure provides a method of interfering with packaging of wild-type influenza A virus by increasing the non-viable virions produced by a cell, the method comprising: contacting the cell infected with a wild-type influenza A virus with modified IAV of described herein in an amount effective to increase the amount of non-viable virions produced by the cell by at least $10^2$, preferably at least $10^3$. In some embodiments, the cell is in vivo within a subject. In this embodiment, the method comprises: administering the modified IAV to a subject having a wild-type influenza A infection. In some embodiments, the modified IAV are administered intramuscularly or intranasally.

In another aspect, the present disclosure provides a method of treating and/or reducing at least one symptom caused by an influenza virus infection in a subject comprising, consisting of, or consisting essentially of administering to the subject a therapeutically effective amount of a modified IAV as provided herein. In some examples, the subject is administered the modified IAV after having contracted influenza A virus infection. In other examples, the subject is administered the modified IAV prior to showing symptoms of influenza A virus infection. In some examples, the modified IAV encodes a second influenza antigen that differs from the parent strain of the IAV. In further examples, the modified IAV encodes an immunomodulatory protein.

The disclosure further provides a method of immunizing a subject to at least one pathogen, the method comprising administering the vaccine described herein to elicit an immune response. The vaccine preferably comprises a heterologous polynucleotide encoding an antigen from at least one pathogen as described for the modified IAV above. In some embodiments, the pathogen is influenza A virus. In some examples, the vaccine comprises modified IAV which encodes a heterologous antigen to the pathogen, and wherein the pathogen is a virus, bacteria, fungus or parasite, described above.

In some embodiments, the vaccine comprises an IAV that encodes one or more immunomodulatory proteins capable of enhancing the immune response.

The present disclosure provides kit comprising the polynucleotide construct or set of constructs described herein and instructions. The polynucleotide construct or set of constructs comprises multiple polynucleotide constructs.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results. The amount of the pharmaceutical composition of the present disclosure which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for administration are generally about $10^4$-$10^9$ pfu and can be administered once, or multiple times with intervals as often as needed. Pharmaceutical compositions of the present invention comprising $10^4$-$10^9$ pfu of modified IAVs can be administered intranasally, intratracheally, intramuscularly or subcutaneously. Effective doses may be extrapolated from dose-response curves derived from in vitro or animal model test systems.

Unless otherwise specified or indicated by context, the terms "a", "an", and "the" mean "one or more." For example, "a protein" or "an RNA" should be interpreted to mean "one or more proteins" or "one or more RNAs," respectively.

"About" is used to provide flexibility to a numerical range endpoint by providing that a given value may be "slightly above" or "slightly below" the endpoint without affecting the desired result, for example, plus or minus 10% (+/−10%). Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

The present invention has been described in terms of one or more preferred embodiments, and it should be appreciated that many equivalents, alternatives, variations, and modifications, aside from those expressly stated, are possible and within the scope of the invention.

The following Examples are provided by way of illustration and not by way of limitation.

EXAMPLES

Influenza A viruses (IAVs) encode their genome as eight negative sense RNA segments. During viral assembly, the failure to package all eight segments, or packaging of a mutated segment, renders the resultant virion incompletely infectious. It is known that the accumulation of these defective particles can limit viral disease by interfering with the spread of fully infectious particles. To harness this phenomenon therapeutically, we defined which viral packaging signals were amenable to duplication and developed a viral genetic platform, which allowed the production of replication competent IAVs that package up to two additional artificial genome segments for a total of 10 segments. In the following Example, we demonstrate that these artificial genome segments are capable of acting as "decoy" segments that, when packaged by wild-type (WT) viruses, lead to the production of non-infectious viral particles. Despite the fact that the 10-segmented viruses are able to replicate and spread in vivo, these genomic modifications render the viruses avirulent. Excitingly, administration of 10-segmented viruses, both prophylactically and therapeutically, was able to rescue animals from normally lethally influenza virus infections. Thus, 10-segmented influenza viruses represent a potent anti-influenza biological therapy that targets the strain-independent process of viral assembly to slow the kinetics of productive viral spread and therefore limit viral disease.

Materials and Methods

Ethics Statement. All mice were purchased from Jackson Laboratories and maintained in Duke University animal facilities. All procedures were carried out in compliance with Duke University IACUC protocol A189-18-08. If our daily monitoring revealed signs of suffering defined as: posturing, ambulating difficulty, ruffled fur, lack of grooming, piloerection, restlessness, pacing, reluctance to move, or bodyweight loss exceeding 20%, then the animal was euthanized. The primary euthanasia method used was $CO_2$ asphyxiation, followed be the secondary euthanasia method, a bilateral thoracotomy.

Animal Infections. Eight to 10-week-old C57BL/6 mice were used for all experiments, with a sample size of at least 4 mice per dose of virus. Prior to infection, mice were anesthetized with a 100-microliter injection of a ketamine-xylazine mixture. Mice were weighed and tail-marked, and 40 microliters of virus diluted in pharmaceutical-grade PBS was administered intranasally. Mice were weighed daily and euthanized once the predetermined humane endpoint, 80% of their starting bodyweight, was reached. Dose determination was based upon $LD_{50}$ experiments in mice, calculated as half of the highest dose causing only mild disease in mice. Euthanasia was performed via $CO_2$ as the primary method, and a bilateral thoracotomy was performed as the secondary method. All procedures were approved by the Duke University IACUC.

Cell Culture. Madin-Darby canine kidney (MDCK) cells were grown in minimal essential medium (MEM) supplemented with 10% fetal bovine serum, HEPES, NaHCO3, GlutaMAX, and penicillin-streptomycin. Human embryonic kidney 293T cells were grown in Dulbecco's modified Eagle's medium (DMEM) supplemented with 10% fetal bovine serum, GlutaMAX, and penicillin-streptomycin. All cells were cultivated at 37° C., at a 5% $CO_2$ content, in the humidity controlled Heracell™ VIOS 160i Thermo Scientific incubators.

Cloning and rescue of 9s and 10s viruses. Recombinant influenza viruses were generated as previously described by use of the ambisense pDZ rescue plasmid system [63]. The 9s PB1 mCherry virus was generated as previously described [52]. The mCherry fluorescent protein coding sequence was adjacent to a 5' Kozak sequence (gccacc) and was cloned into a PR8 PB1 packaging vector using PCR and subsequent NEBuilder® HiFi DNA Assembly reaction. The PB1 packaging vector consisted of nucleotides 1-146 of the 5'-most PB1 sequence (with all ATG start sites silently mutated); an ECORV and Pme1 sequence separated the subsequent 3'-most PR8 PB1 sequence of nucleotides 2189-2341. The PB1 coding sequence (nucleotides 25-2298) is adjacent to a 5' Kozak sequence and was cloned into a PR8 NA packaging vector using PCR and subsequent NEBuilder® HiFi DNA Assembly reaction. The PB1 coding sequence 5'-most 75 nt and 3'-most 81 nt were silently mutated to remove packaging signal activity. The NA packaging vector consisted of nucleotides 1-173 of the 5'-most PR8 NA sequence (with all ATG start sites silently mutated); an ECORV and Pme1 sequence separated the subsequent 3'-most NA sequence of nucleotides 1205-1413. Packaging vectors and primers were synthesized as ordered through Integrated DNA Technologies, Inc. Virus was generated by transfecting 1 microgram of recombinant PB1-mCherry-PB1 and NA-PB1-NA plasmids into low-passage 293T cells alongside 0.5 micrograms of each of the remaining 7 respective wildtype plasmids (PB2, PA, HA, NP, NA, M, NS). Transfections were conducted using 12 microliters of Mirus Trans-IT LT1 reagent in 200 microliters of OPTI-MEM. Rescue supernatant was collected after 24 hours of incubation, with 200 microliters injected into 10-day-old chicken eggs purchased from Charles River Laboratories, Inc. Eggs were allowed to incubate virus for 72 hours prior to collection of allantoic fluid. Viruses were purified via plaquing in MDCK cells and subsequent amplification in chicken eggs.

The 9s PB2 sfGFP virus was generated as follows: The sfGFP fluorescent protein coding sequence was adjacent to a 5' Kozak sequence and was cloned into a PR8 PB2 packaging vector using PCR and subsequent NEBuilder® HiFi DNA Assembly reaction. The PB2 packaging vector consisted of nucleotides 1-158 of the 5'-most PB2 sequence (with all ATG start sites silently mutated); an Nhe1 and Xho1 sequence separated the subsequent 3'-most PB2 sequence of nucleotides 2189-2341. The PB2 coding sequence (nucleotides 25-2298) is adjacent to a 5' Kozak sequence and was cloned into a PR8 PA packaging vector using PCR and subsequent NEBuilder® HiFi DNA Assembly reaction. The PB1 coding sequence 5'-most 30 nt and 3'-most 85 nt were silently mutated to remove packaging signal activity. The PA packaging vector consisted of nucleotides 1-129 of the 5'-most PA sequence (with all ATG start sites silently mutated); an ECORV and Pme1 sequence separated the subsequent 3'-most PA sequence of nucleotides 2050-2233. Virus was generated by transfecting 1 microgram of recombinant PB2-sfGFP-PB2 and PA-PB2-PA plasmids into low-passage 293T cells alongside 0.5 micrograms of each of the remaining 7 respective wildtype plasmids (PB1, PA, HA, NP, NA, M, NS). Transfections were conducted using 12 microliters of Mirus Trans-IT LT1 reagent in 200 microliters of OPTI-MEM. Rescue supernatant was collected after 24 hours of incubation, with 200 microliters injected into 10-day-old chicken eggs. Eggs were allowed to incubate virus for 72 hours prior to collection of allantoic fluid. Viruses were purified via plaquing in MDCK cells and subsequent amplification in chicken eggs.

The 9s PB1 DI virus was generated as follows: the design of the PB1 DI segment is based upon characterization of INS002, as described in [38]. DNA was synthesized via Integrated DNA Technologies, Inc. in which the aforementioned PB1 packaging vector contained PR8 PB1 nucleotides 146-190 followed by nucleotides 2094-2188. In the 5'-most region of this construct, all ATG start codons were silently mutated to prevent generation of uncharacterized transcripts and protein products. Virus was generated by transfecting 0.75 microgram of recombinant PB1-DI-PB1 plasmid and 1 microgram of NA-PB1-NA plasmid into low-passage 293T cells alongside 0.5 micrograms of each of the remaining 7 respective wildtype plasmids (PB2, PA, HA, NP, NA, M, NS). Transfections were conducted using 12 microliters of MIRUS Mirus Trans-IT LT1 reagent in 200 microliters of OPTI-MEM. Rescue supernatant was collected after 24 hours of incubation, with 200 microliters injected into 10-day-old chicken eggs purchased from Charles River Laboratories, Inc. Eggs were allowed to incubate virus for 72 hours prior to collection of allantoic fluid. Viruses were purified via plaquing in MDCK cells and subsequent amplification in chicken eggs.

The 10-segment PB2 sfGFP, PB1 mCherry virus was generated by transfecting 1 microgram of recombinant PB2-sfGFP-PB2, PA-PB2-PA, PB1-mCherry-PB1, and NA-PB1-NA plasmids into low-passage 293T cells alongside 0.5 micrograms of each of the remaining 6 respective wildtype plasmids (PA, HA, NP, NA, M, NS). Transfections were conducted using 14 microliters of Minis Trans-IT LT1 reagent in 200 microliters of OPTI-MEM. Rescue supernatant was collected after 24 hours of incubation, with 200 microliters injected into 10-day-old chicken eggs. Eggs were allowed to incubate virus for 72 hours prior to collection of allantoic fluid. Viruses were purified via plaquing in MDCK cells and subsequent amplification in chicken eggs. Stocks of concentrated 10s virions were prepared using a 30% sucrose cushion for 1 h at 25,700 rpm on the Sorvall TH-641 swinging bucket rotor.

Viral titering. Allantoic fluid was collected from chicken eggs following infection, and viral titer was determined via standard plaque assay procedures on MDCK cells. Briefly, cells were incubated for 1 h in 500 microliters of diluted virus suspension at 37° C., before removing the virus and applying the agar overlay. Cells were then incubated at 37° C. for 72 h before being fixed in 4% paraformaldehyde (PFA) in phosphate-buffered saline (PBS) for at least 4 h. The 4% PFA was then aspirated, and the agar layer was removed before washing cells in PBS and incubating them at 4° C. overnight in mouse serum from PR8-infected mice. Mouse serum was diluted 1:2,000 in antibody dilution buffer, which was made using 5% (wt/vol) nonfat dried milk and 0.05% Tween 20 in PBS. Following the overnight incubation in primary antibody, plaque assays were washed with PBS three times and then incubated for 1 h in anti-mouse IgG horseradish peroxidase (HRP)-conjugated sheep antibody (GE Healthcare) diluted 1:4,000 in antibody dilution buffer. Assays were then washed three additional times with PBS and incubated in 0.5 ml of True Blue reagent for 30 min to allow for the staining of plaques. Once plaques were visible, plates were washed with water and allowed to dry before counting (only wells with greater than 3 plaques were used for the calculation of endpoint titer).

Viral Growth Curves. For each growth curve, 200 PFU of respective virus was injected into 10-day old embryonated chicken eggs. Eggs were refrigerated at 0, 24, 48, or 72 hours post-infection and allatonic fluid was collected after 48 hours of refrigeration at 4° C. Aliquots of allantoic fluid were immediately frozen at −80° C. to be thawed for use in HA assays and standard plaque assay procedures. All experiments were conducted in biological triplicate.

Hemagglutination (HA) assay. Hemagglutination (HA) assays were performed by diluting virus-containing allantoic fluid in cold PBS. 50 microliters of chicken blood diluted 1:80 in cold PBS was mixed with each sample and incubated at 4° C. overnight prior to scoring.

DI unit calculation. Defective Interfering or "DI" Units were calculated by normalizing a virus's HA score and endpoint titer to that of WT PR8. These normalized values were then averaged, and the HA score was divided by its normalized, averaged endpoint titer.

Microscopy time course. 12-wells of MDCK cells were seeded with approximately 85,000 cells for use 24 hours later for all microscopy experiments. MDCKs were infected for 1 hour at an MOI of 0.05 with either 9s PB1 mCherry, 9s PB2 sfGFP, or WT PR8 virus diluted in PBS/BSA at a total volume of 500 microliters. MDCKs were infected at an MOI of 0.1 with the 10s virus. The WT PR8 control was infected at an MOI of 0.05. Following the incubation period, the infection medium was removed and cells were placed in complete medium supplemented with 1:1000 diluted TPCK trypsin. At the indicated time after infection, MDCK cell medium was removed and replaced with 1 ml of warm PBS. Cells were incubated with Hoechst stain (1 microliter/ml of PBS) to allow for the staining of nuclei, and imaging was performed on the Zoe fluorescent cell imager (Bio-Rad) using the same gain, exposure and zoom settings for all images taken. Images were then processed with ImageJ (NIH).

Results

Evaluation of Viral Genetic Manipulations Capable of Generating 9-Segmented IAVs We were interested in generating influenza viruses that could be genetically programmed to harbor artificial genomic segments that would interfere with the correct packaging of genome segments into nascent virions. It was previously reported that the NA packaging signals could be duplicated and utilized to package a ninth genomic segment [51]. While this approach was utilized to encode additional antigens as a vaccine platform, we theorized that this and similar approaches could be utilized to generate viruses harboring artificial, interfering segments. We therefore tested the ability to duplicate various packaging signals and generate 9-segmented viruses. We tested: NA, NP, HA, and PA duplicated packaging signals harboring different viral proteins in different combinations (Table 1). In all cases, the "$9^{th}$" segment (FIG. 7) was designed with unique packaging signals so that it would always be packaged, but failure to package the duplicated packaging signal segment would lead to the loss of an essential viral protein. The $9^{th}$ segment always encoded super-folder GFP (sfGFP) or mCherry. Surprisingly, very few segment duplications were amenable to this approach. As previously reported, duplication of the NA packaging signal is tolerated, but of everything else tested, only duplication of the PA packaging signal was tolerated (Table 1).

Figure 7:
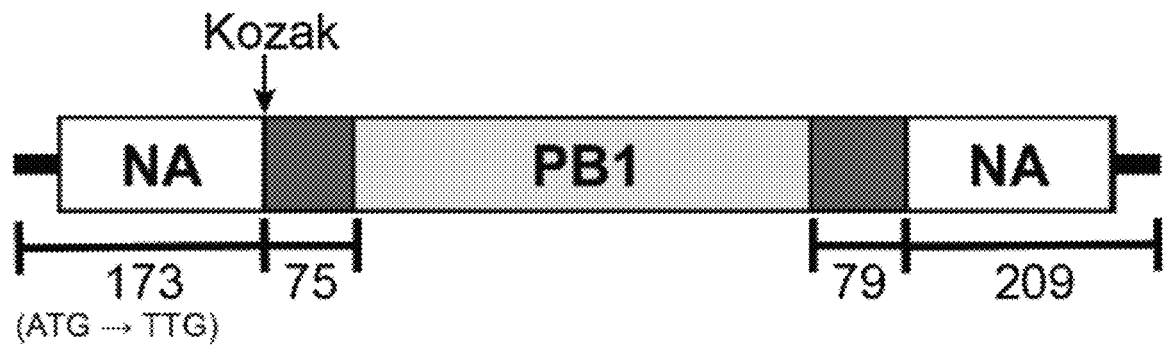
FIG. 7. Diagrams of the artificial viral segments tested in this study. (A) Design of PB1 ORF flanked by NA packaging signals. (B) Design of mCherry flanked by PB1 packaging signals. (C) Design of PB2 ORF flanked by NP packaging signals. (D) Design of sfGFP flanked by PB2 packaging signals. (E) Design of the HA ORF flanked by NS packaging signals. (F) Design of sfGFP flanked by HA packaging signals. (G) Design of PB2 ORF flanked by PA packaging signals. (H) Design of M1 ORF flanked by HA packaging signals. (I) Design of the zsGreen (splice site) M2 ORF flanked by M packaging signals. (J) Design of the NS1 ORF flanked by NA packaging signals. (K) Design of the mCherry (splice site) NEP ORF flanked by NS packaging signals. For all diagrams, the indicated regions define the number of nucleotides. Dark grey regions represent silently mutagenized regions of the viral ORF.
Figure 7:
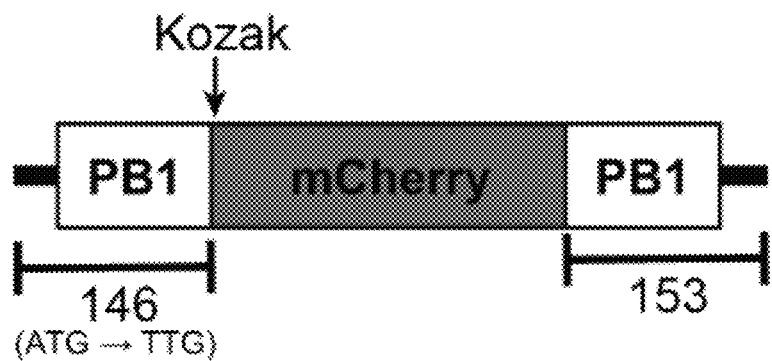
Figure 7:
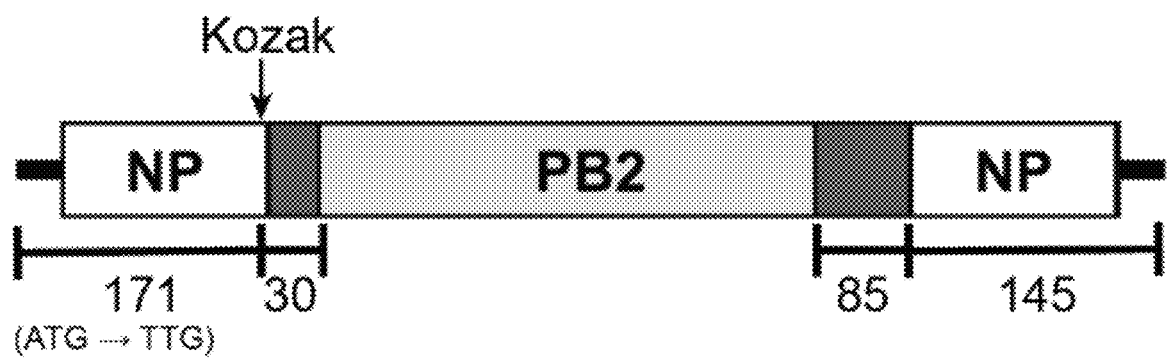
Figure 7:
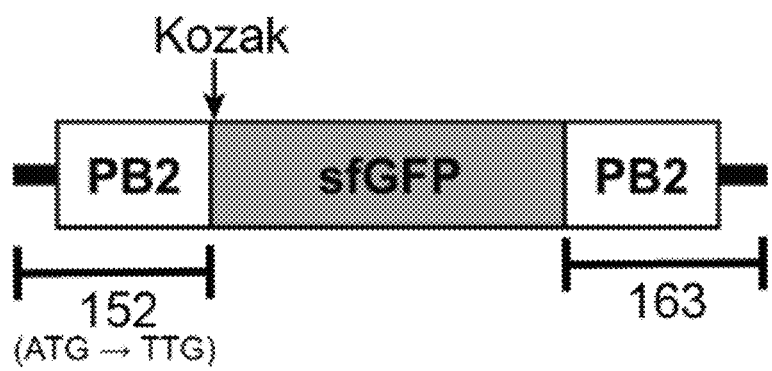
Figure 7:
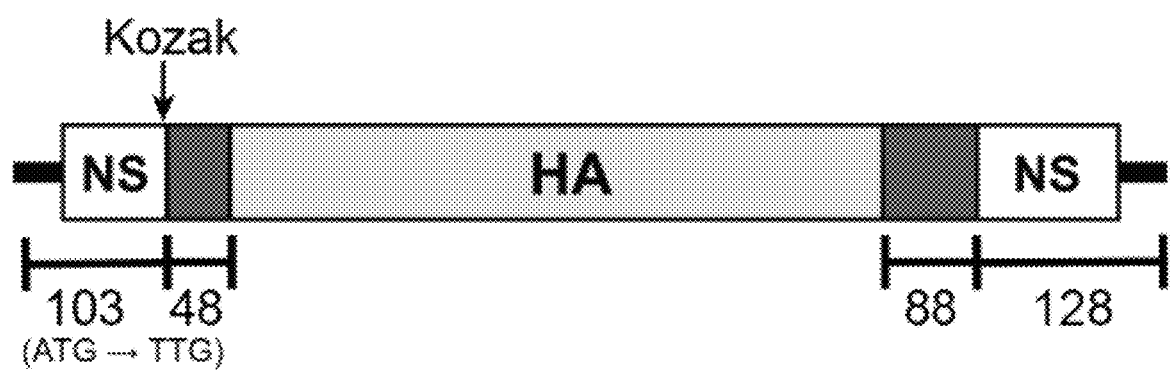
Figure 7:
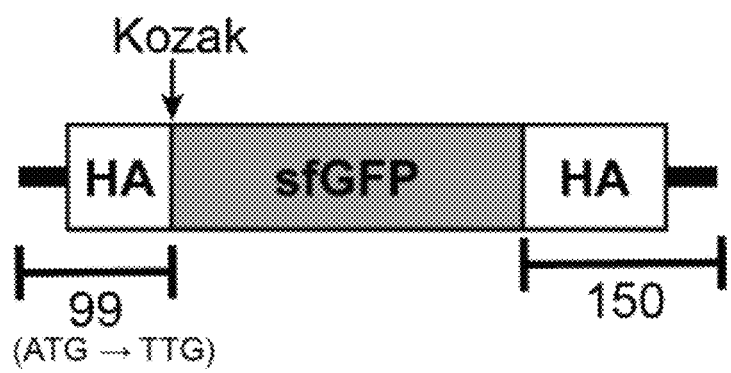
Figure 7:
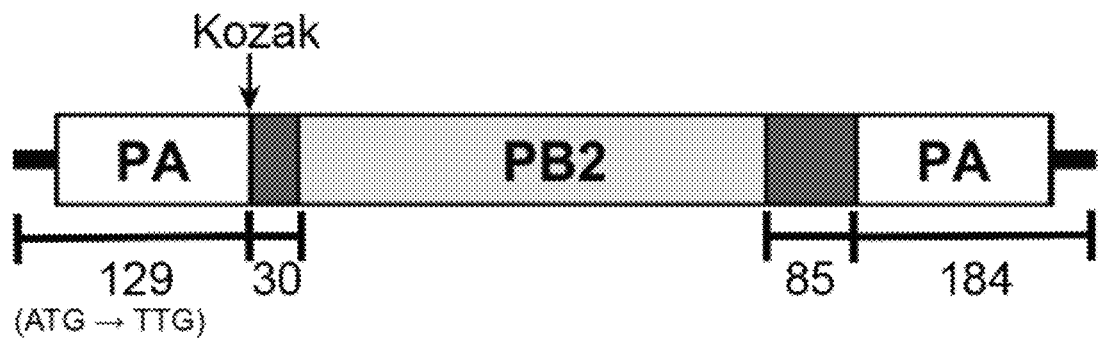
Figure 7:
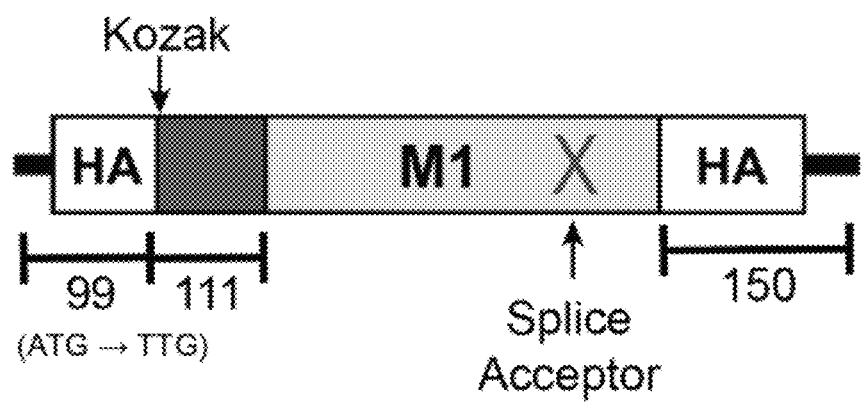
Figure 7:
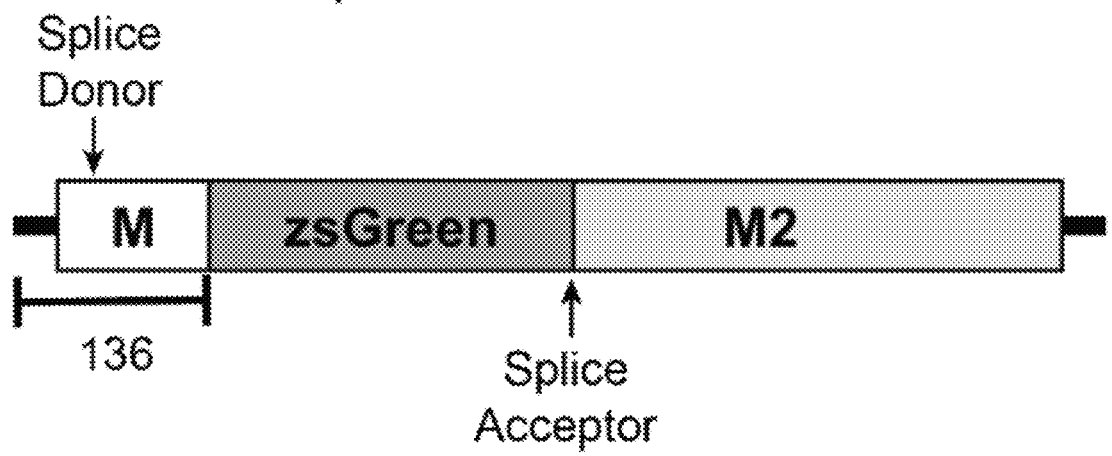
Figure 7:
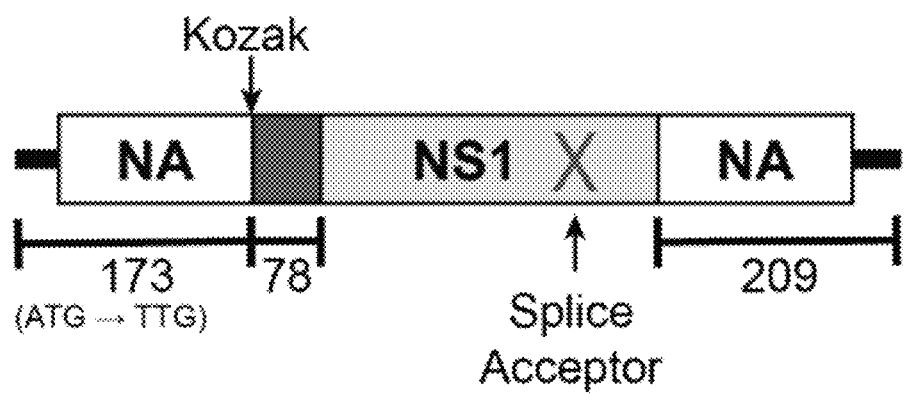
Figure 7:
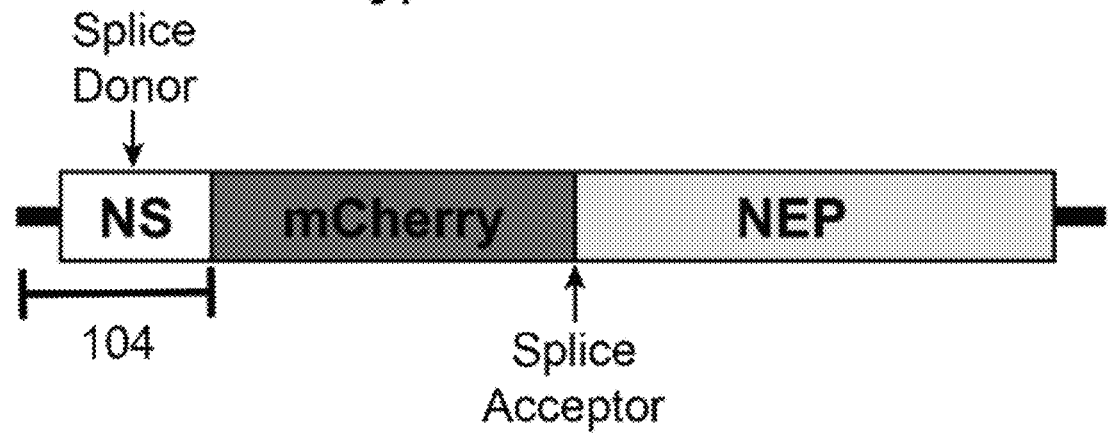

Additionally, we also tested the potential of using splice sites in the 7th and 8th segments of IAV to generate 9S viruses expressing either M1 or NS1 in the ninth segment and a fluorescent protein 5' to M2 or NEP in segment 7 or 8, respectively (Table 1, FIG. 7). Duplicating HA packaging signals and encoding M1 as an artificial segment was unsuccessful, however duplicating the NA packaging signals and encoding NS1 successfully yielded 9S virions. The "NS" segment encoding mCherry and NEP however, immediately lost mCherry signal upon viral rescue, indicating that this approach is not useful for the stable incorporation of protein or nucleic acid. From these experiments we conclude that the duplication of packaging signals is not a generalizable approach for all segments, but in some specific cases, such as the with NA and PA packaging signals, this approach can be utilized to force viral packaging of a 9$^{th}$ genomic segment.

TABLE 1.9 segmented virus design strategies. A description of the manipulated packaging signals, encoded proteins, and success of rescuing each 9 segmented IAV strategy.

| | Segment Design | Protein | Successful Rescue? |
|---|---|---|---|
| | 9s PB1-mCherry-PB1/NA-PB1-NA Design | | |
| 1 | WT PB2 | PB2 | Yes |
| 2 | NA-PB1-NA | PB1 | (Gao et al.) |
| 3 | WT PA | PA | |
| 4 | WT HA | HA | |
| 5 | WT NP | NP | |
| 6 | WT NA | NA | |
| 7 | WT M | M1, M2 | |
| 8 | WT NS | NS1, NEP | |
| 9 | PB1-mCherry-PB1 | mCherry | |
| | 9s PB2-sfGFP-PB2/NP-PB2-NP Design | | |
| 1 | NP-PB2-NP | PB2 | No |
| 2 | WT PB1 | PB1 | |
| 3 | WT PA | PA | |
| 4 | WT HA | HA | |
| 5 | WT NP | NP | |
| 6 | WT NA | NA | |
| 7 | WT M | M1, M2 | |
| 8 | WT NS | NS1, NEP | |
| 9 | PB2-sfGFP-PB2 | sfGFP | |
| | 9S HA-sfGFP-HA/NS-HA-NS Design | | |
| 1 | WT PB2 | PB2 | No |
| 2 | WT PB1 | PB1 | |
| 3 | WT PA | PA | |
| 4 | NS-HA-NS | HA | |
| 5 | WT NP | NP | |
| 6 | WT NA | NA | |
| 7 | WT M | M1, M2 | |
| 8 | WT NS | NS1, NEP | |
| 9 | HA-sfGFP-HA | sfGFP | |
| | 9s PB2-sfGFP-PB2/PA-PB2-PA Design | | |
| 1 | PA-PB2-PA | PB2 | Yes |
| 2 | WT PB1 | PB1 | |
| 3 | WT PA | PA | |
| 4 | WT HA | HA | |
| 5 | WT NP | NP | |
| 6 | WT NA | NA | |
| 7 | WT M | M1, M2 | |
| 8 | WT NS | NS1, NEP | |
| 9 | PB2-sfGFP-PB2 | sfGFP | |
| | 9s M-zsGreen\|M2-M/HA-M1-HA | | |
| 1 | WT PB2 | PB2 | No |
| 2 | WT PB1 | PB1 | |
| 3 | WT PA | PA | |
| 4 | WT HA | HA | |
| 5 | WT NP | NP | |
| 6 | WT NA | NA | |
| 7 | HA-M1-HA | M1 | |
| 8 | WT NS | NS1, NEP | |
| 9 | M-zsGreen \| M2-M | zsGreen, M2 | |
| | 9s NS-mCherry\|NEP-NS/NA-NS1-NA | | |
| 1 | WT PB2 | PB2 | Yes (Unstable) |
| 2 | WT PB1 | PB1 | |
| 3 | WT PA | PA | |
| 4 | WT HA | HA | |
| 5 | WT NP | NP | |
| 6 | WT NA | NA | |
| 7 | WT M | M1, M2 | |
| 8 | NA-NS1-NA | NS1 | |
| 9 | NS-mCherry \| NEP-NS | mCherry, NEP | |

Characterization of 9-Segmented Viruses and Their Therapeutic Efficacy

After determining which combinations of packaging signal duplications were tolerable, we began in vitro characterizations of the 9S PB1 mCherry virus, with duplicated NA packaging signals, and the 9S PB2 sfGFP virus, with duplicated PA packaging signals (FIG. 1A-1B). Multicycle growth experiments, both in embryonated chicken eggs and in MDCK cells, demonstrated that while both of these viruses exhibit attenuated levels of growth (FIG. 1C), they do successfully package and propagate the artificial segment (FIG. 1D). We hypothesized that the decreased viral growth may be due to the viruses only packaging one of the segments that harbors the duplicated packaging signal. If this were the case, we would expect to observe a large number of defective, 8 segmented viruses lacking an essential viral protein. In order to test this, we grew the viruses in embryonated chicken eggs and measured infectious particles via plaque assay, and we also performed a hemagglutinin (HA) assay, which measures both infectious and noninfectious particles (FIG. 1E-1F). Again, we observed a dramatic reduction in viral titer, however the magnitude of the observed defect in the HA assay was much smaller. To represent this difference, we calculated the "Relative DI units" of our 9S viruses, relative to WT virus, with WT set at an arbitrary value of 1, by dividing HA units by the endpoint titer (FIG. 1G). As expected, the 9S PB1 mCherry virus produced ~$10^2$ times more non-viable progeny than did the WT PR8 virus, while the 9S PB2 sfGFP virus produced ~$10^3$ times more non-viable progeny than did WT PR8 (FIG. 1G). Thus, both 9S viruses produced a significantly higher ratio of non-viable to viable virions than WT PR8 virus, and that ratio was, to some extent, dictated by which viral segment had been duplicated.

Figure 2:
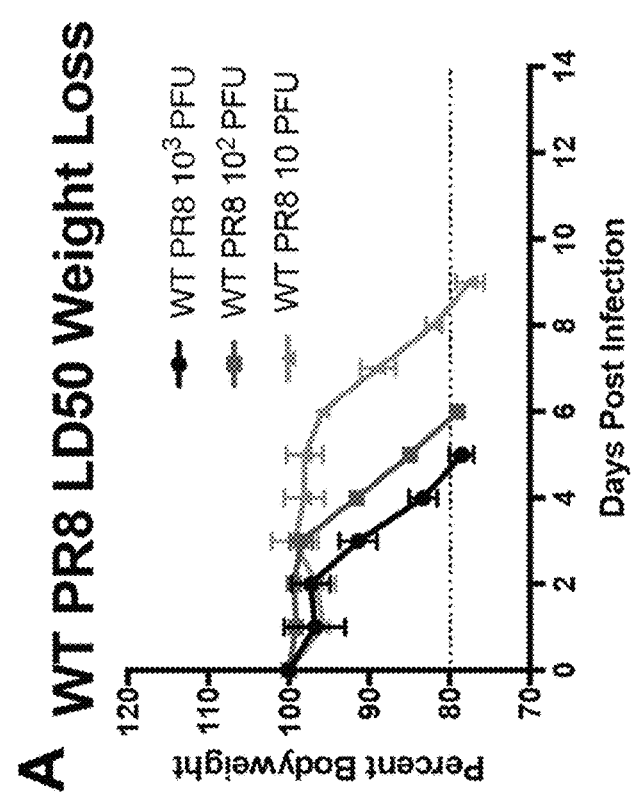
FIG. 2. 9-Segmented influenza viruses are highly attenuated and their administration at the time of infection can protect from lethal viral challenge. (A-C) Weight loss curves from infections with the indicated doses of WT PR8 virus (A), the 9s PB1 mCherry virus (B), or the 9s PB2 sfGFP virus (C). (D-F) Survival curves from infections with the indicated doses of WT PR8 virus (D), the 9s PB1 mCherry virus (E), or the 9s PB2 sfGFP virus (F). (G) Schema of C57BL/6J coinfection challenges. (H-J) Weight-loss curves from infecting mice with a lethal dose of WT PR8 ((●), 20 PFU) (H), a sublethal dose of the 9s PB1 mCherry virus ((▲), 500 PFU), or a lethal dose of WT PR8 virus in combination with 500 PFU 9s PB1 mCherry virus (□) (I),or a sublethal dose of the 9s PB2 sfGFP virus ((▲) 500 PFU) or a lethal dose of WT PR8 virus in combination with 500 PFU 9s PB2 sfGFP virus (□) (J). (K-M) Survival curves from coinfections challenging mice described in panels H-J, respectively.
Figure 2:
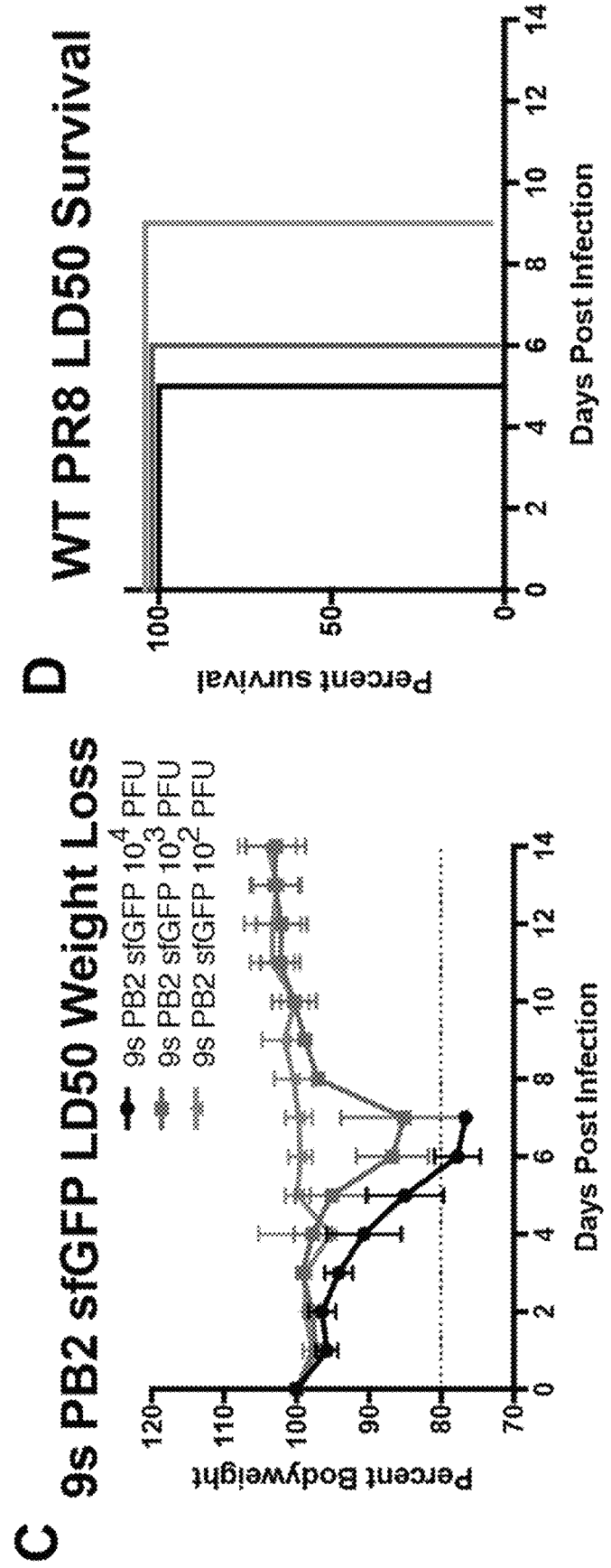
Figure 2:
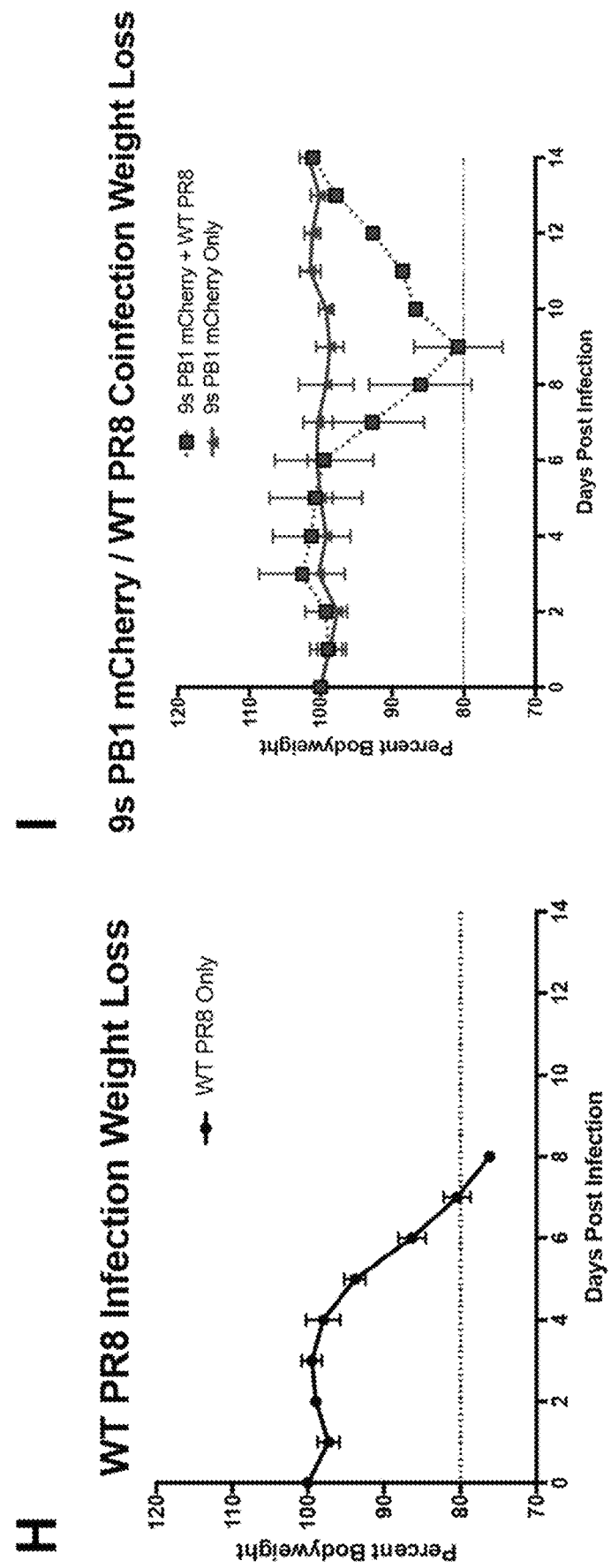
Figure 2:
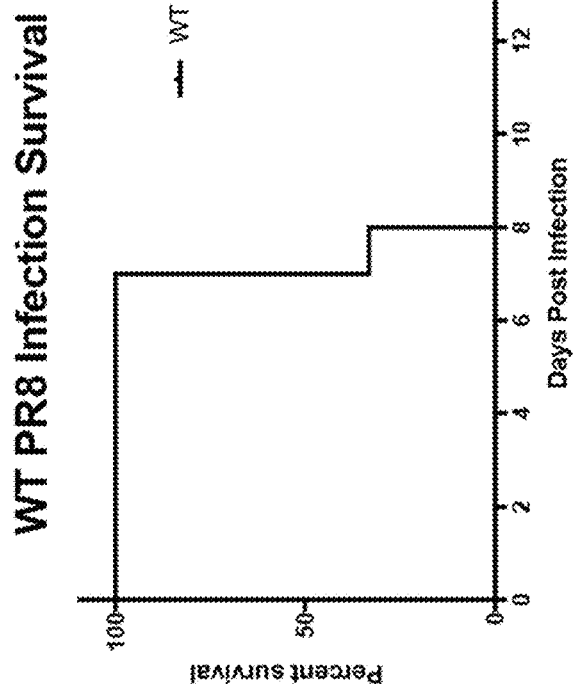
Figure 2:
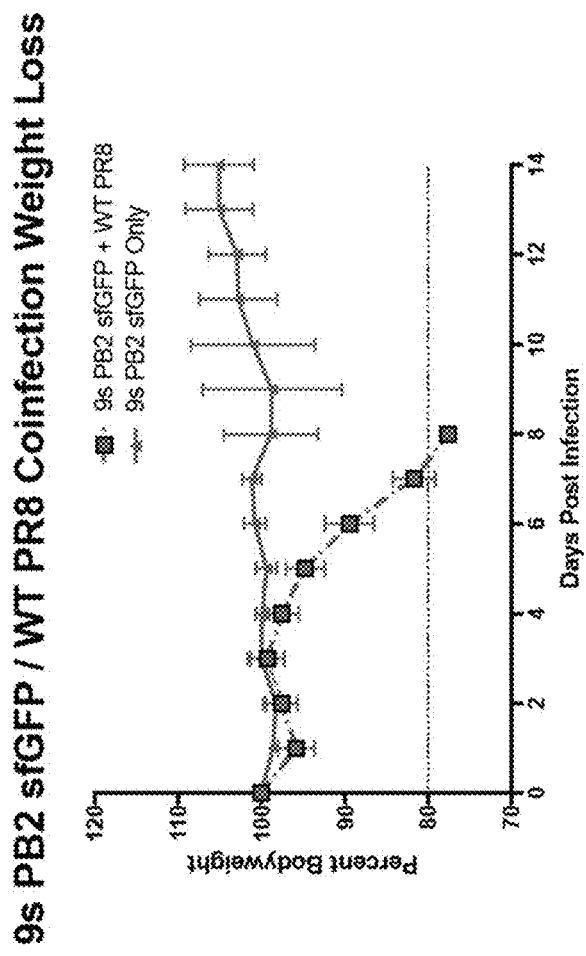
Figure 2:
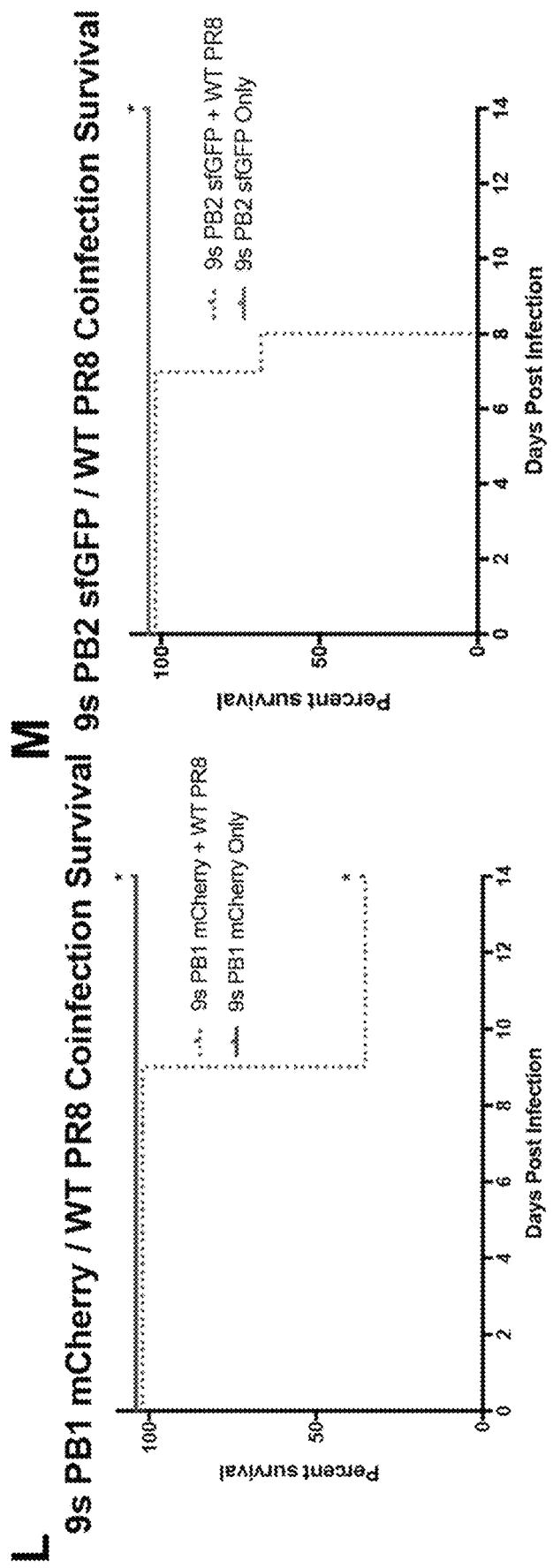

We next wanted to assess how a 9$^{th}$ segment affected the virulence of the virus, as well as assay the ability of the two 9S fluorescent viruses to modulate influenza disease. To determine if the addition of the 9$^{th}$ segment attenuated the virus, LD50 experiments were performed in immunocompetent C57BL/6 mice. Wild-type PR8 virus was found to be lethal at all doses tested, killing all infected mice with as little as 10 PFU (FIG. 2A-2D). The two 9S viruses, however, were significantly attenuated relative to the parental virus. The 9S PB1 mCherry virus required $10^4$ PFU for lethality and $10^2$ PFU treated animals showed no death or weight loss (FIGS. 2B, 2E). Similarly, the 9S PB2 sfGFP caused lethal disease at a dose of $10^4$ PFU and $10^2$ PFU treated animals exhibited no death or weight loss (FIGS. 2C, 2F). The attenuation of the 9S viruses suggested that these viral genomic designs may fit the criteria of a live-attenuated therapeutic. We therefore assessed the capability of each 9-segmented fluorescent virus to interfere with a lethal challenge of WT PR8. For this initial test, we coinfected animals with 20 PFU of WT virus in combination with 500 PFU of either the 9S PB1 mCherry or the 9S PB2 sfGFP virus and monitored animals for body weight loss for 14 days post-infection FIG. 2G). 500 PFU of the 9S viruses was chosen as the highest dose that would not be expected to induce any clinical disease. Non-treated control animals rapidly lost body weight and succumbed to the challenge, as expected (FIGS. 2H, 2K). Administration of the 9S PB1 mCherry virus caused a measurable protective effect, with treated animals experiencing an ~48 hour delay in the onset of body weight loss when compared to the lethal WT PR8 challenge (FIG. 2I). Moreover, 25% of coinfected animals survived and recovered from this normally lethal challenge with WT PR8 (FIG. 2L). In contrast, the 9S PB2 sfGFP virus did not cause treated animals to display any statistically significant reduction in weight loss or increased survival compared to the lethal WT PR8 challenge alone (FIGS. 2J, 2M).

The Artificial Viral Segment Size is not Correlated With Therapeutic Effect

Figure 3:
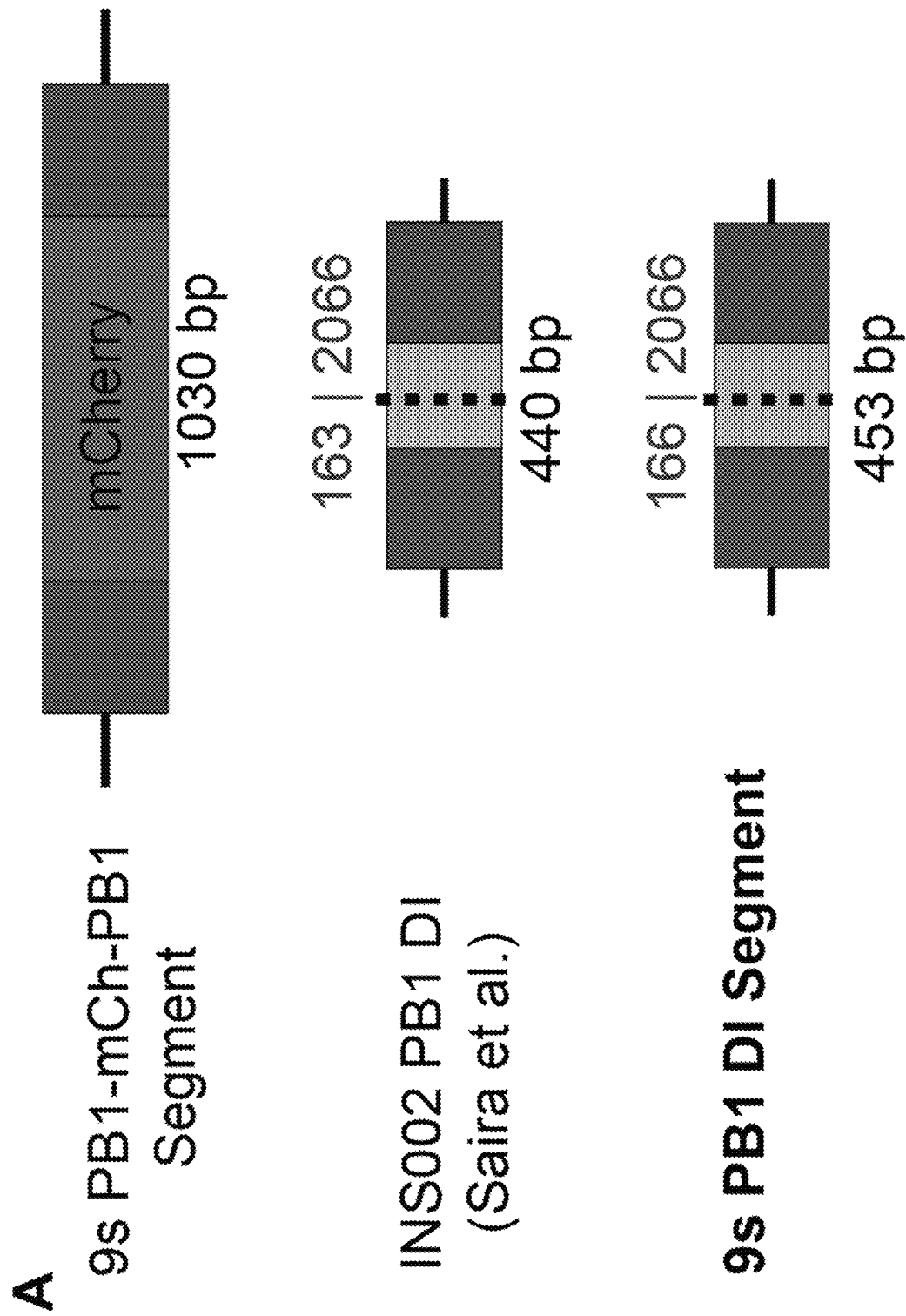
FIG. 3. 9-Segmented influenza viruses can harbor a natural defective interfering-like segment. (A) A schematic comparing the 9s PB1-mCherry-PB1 segment and the INS002 PB1 DI segment, which acted as a basis for the design of the 9s PB1 DI segment. (B) A schematic detailing the genome design of the 9s PB1 DI virus, including a ninth PB1-DI-PB1 segment. (C) Growth curve of the 9s PB1 DI virus titered in MDCK-cells at 0, 24, 48, and 72 hours post-infection in 10-day old embryonated chicken eggs. (D) Endpoint titer 72 hours post-infection in embryonated chicken eggs of the 9s PB1 DI virus as compared to WT PR8 virus. (E) HA assay 72 hours post infection in 10-day old embryonated chicken eggs of the 9s PB1 DI virus as compared to WT PR8 virus. (F) The "DI Units" of the 9s PB1 DI virus as compared to that of WT PR8 virus, calculated by dividing normalized HA units by normalized endpoint titer. (G) Weight loss curves from infection with the indicated doses of the 9s PB1 DI virus. (H) Survival curves from infections with the indicated doses of 9s PB1 DI virus. (I) Weight-loss curves from infecting mice with a sublethal dose of the 9s PB1 DI virus ((▲), 500 PFU), a lethal dose of WT PR8 ((●), 20 PFU), or a lethal dose of WT PR8 virus in combination with 500 PFU 9s PB1 DI virus (□). (J) Survival curves from infections described in panel I. For all graphs, * represents a p-value of ≤0.05 and ** represents a p-value of ≤0.001.
Figure 3:
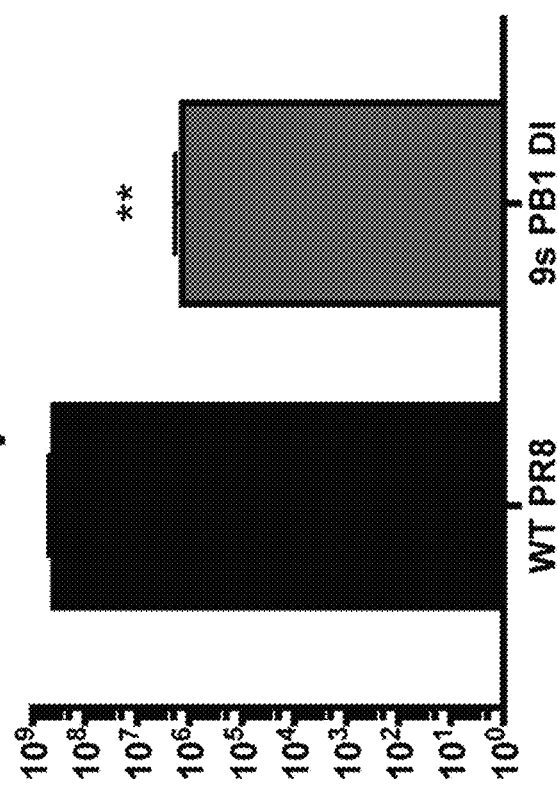
Figure 3:
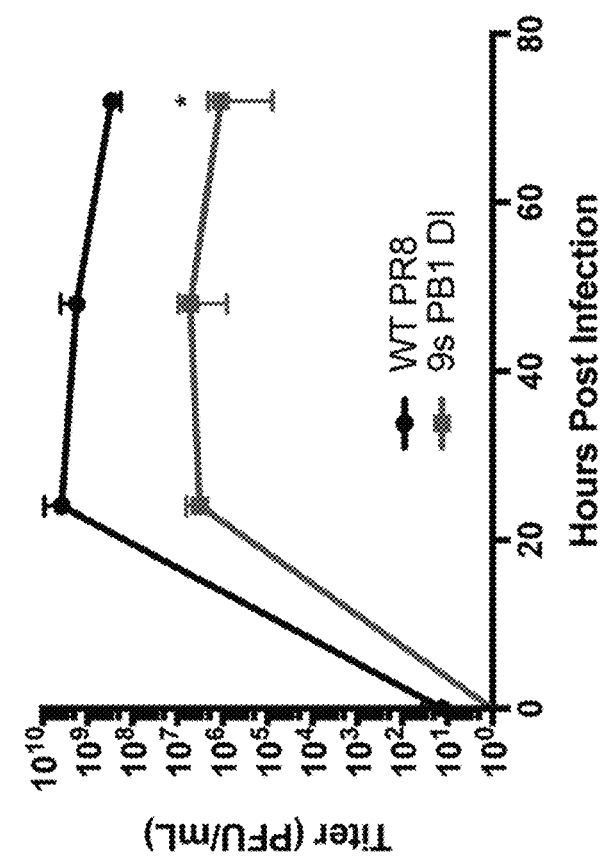
Figure 3:
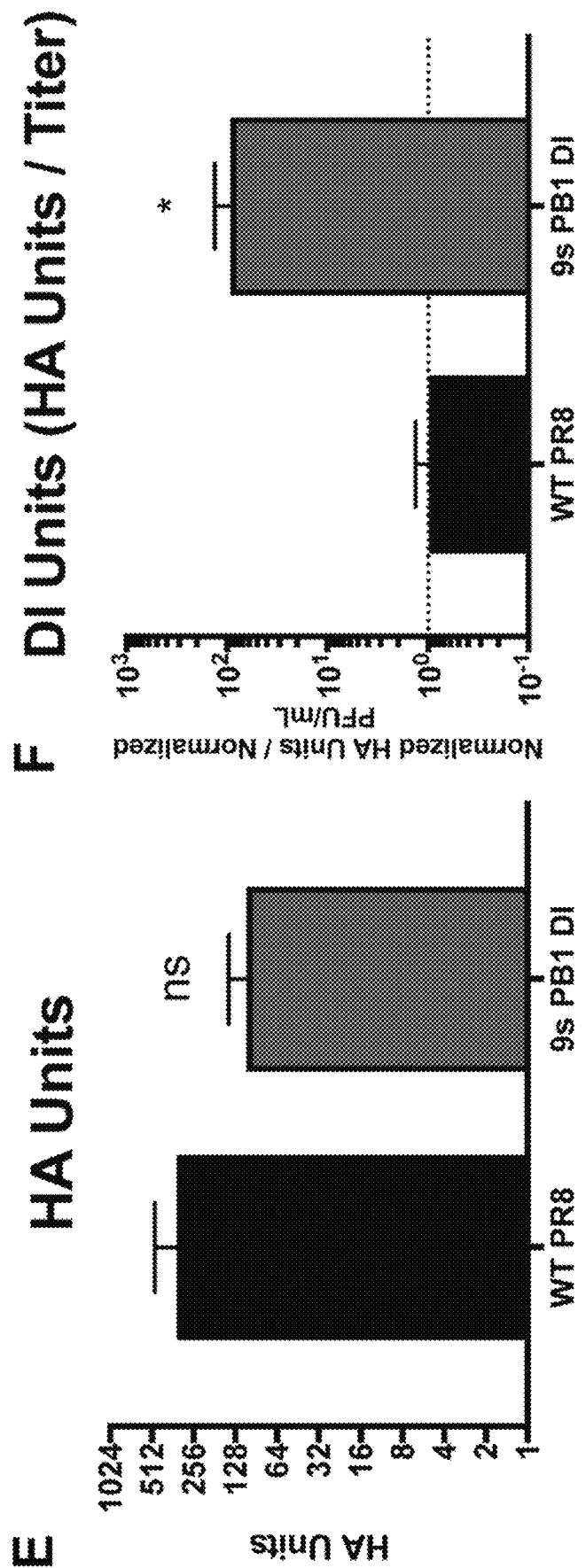
Figure 3:
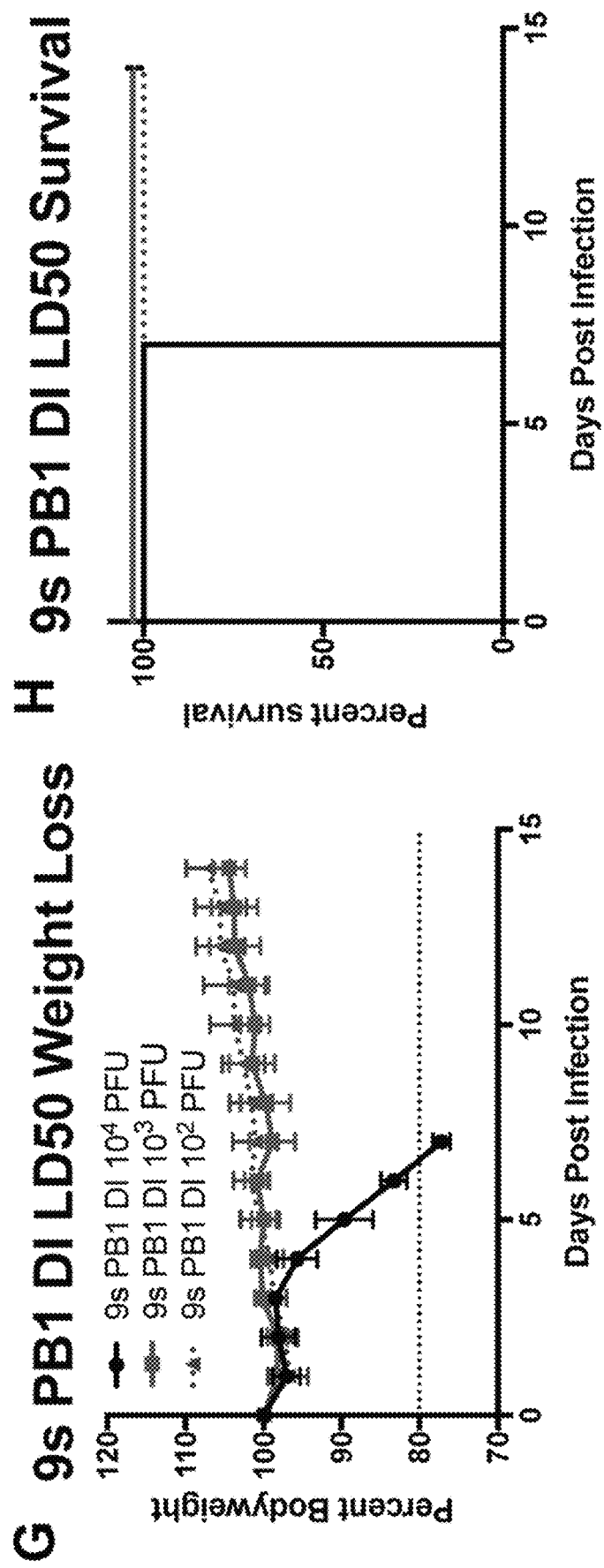
Figure 3:
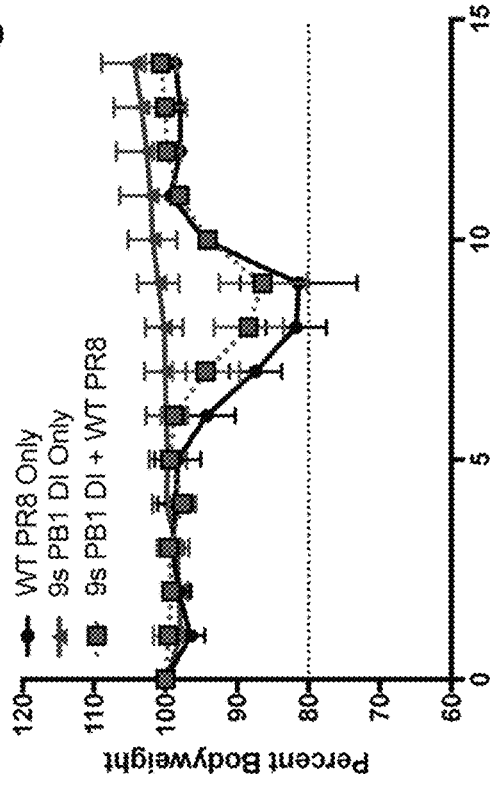
Figure 3:
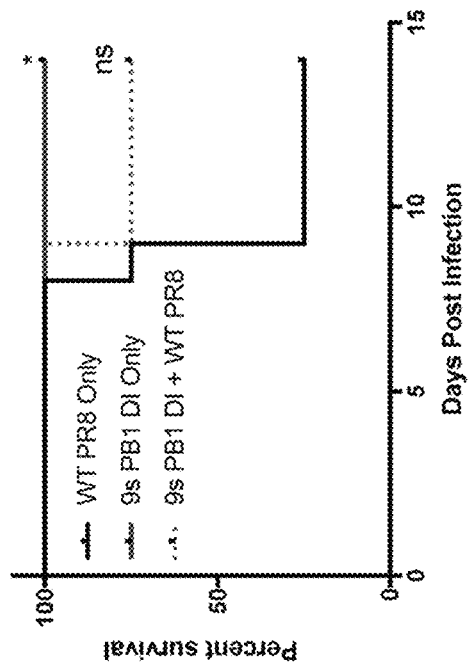

While the 9S PB1 mCherry virus did offer some therapeutic effect, the effect size was minimal. We hypothesized that this was likely due to the design of our segment. During normal WT replication, DI segments arise from the large-scale deletion of ORFs, often reducing the size of a DI segment to a total of less than 500 nucleotides. This significant reduction in size causes the DI segment to be replicated much faster than the full-length WT segment, drastically enhancing the chance that the DI segment is packaged into a progeny virion over the WT one. Our artificial segments, however, were actually larger than a standard DI segment, potentially reducing the efficacy of this strategy. In order to determine if the protective effect of a 9S virus could be augmented by making it more like a DIP, we designed a DI-like oligonucleotide to replace PB1 mCherry, based on a previously characterized PB1 DI segment reported by Saira et al. [38] (FIG. 3A). We chose to focus on the PB1-mCherry segment as this segment showed a larger degree of protection from challenge relative to the PB2-sfGFP segment. We used the PB1 DI segment was in place of the mCherry expressing segment to generate a virus harboring a more DI-like segment (FIG. 3B). The 9S PB1 DI virus again was attenuated relative to WT viruses by approximately the same magnitude as the other 9S viruses (FIG. 3C). Analysis of titer and HA units after growth in chicken eggs revealed that similarly to the other 9S viruses, the 9S PB1 DI virus produced roughly $10^2$ times more non-viable progeny than WT PR8 virus (FIG. 1D-1F).

As expected, the 9S PB1 DI virus was significantly attenuated in vivo, even more so than the previous 9S viruses. Only the highest dose tested, $10^4$ PFU, was lethal, whereas the other two doses, $10^3$ and $10^2$ PFU, caused no death or weight loss (FIG. 3G-3H). To test the protective efficacy of the 9S DI virus, we simultaneously treated mice with 500 PFU of the DI virus together with a normally lethal dose of WT PR8. Similar to the 9S PB1 mCherry virus, the 9S PB1 DI virus was found to confer a protective effect, with weight loss occurring 24 hours later than seen in the control, WT PR8 challenged mice, and an increase in survival rates (FIGS. 3I, 3J). Thus, the 9S PB1 DI virus had a very similar protective effect to the 9S PB1 mCherry virus, suggesting that the ability of these viruses to interfere with influenza disease is independent of the artificial genome segment size.

Figure 4:
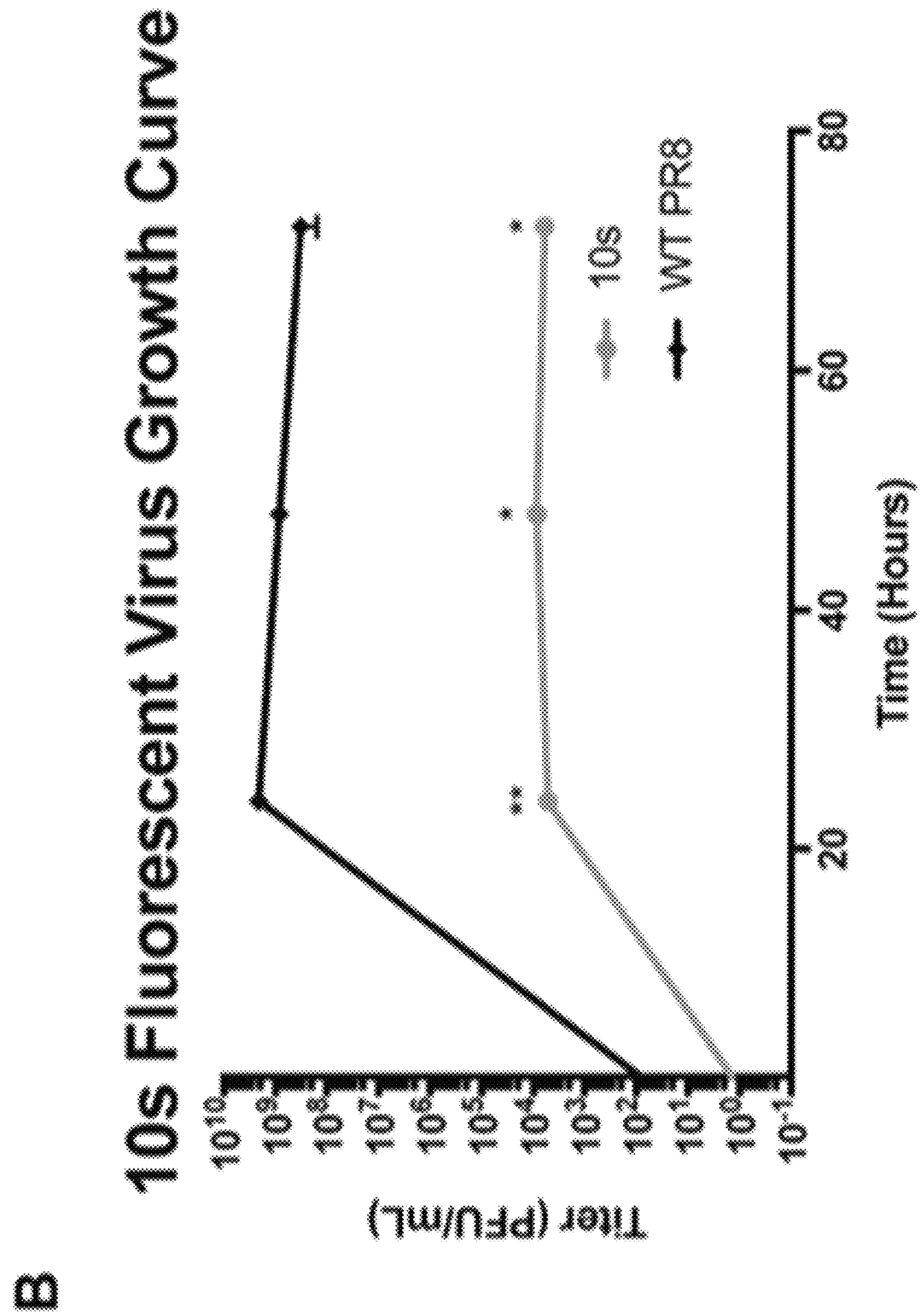
FIG. 4. 10-Segmented fluorescent viruses can be generated by combining two 9-segmented approaches. (A) Genome design of the 10s PB2 sfGFP PB1 mCherry virus. (B) Growth curve of the 10s virus measuring titered in MDCK cells at 0, 24, 48, and 72 hours post-infection in 10-day old embryonated chicken eggs as compared to PR8 WT. (C) Fluorescent microscopy images of 10s or WT PR8 virus-infected MDCK cells at 0, 6, 12, and 24 hours post-infection; nuclei were stained blue using DAPI staining, and the scale bar represents 100 micrometers. (D) Endpoint titer 72 hours post-infection in 10-day old embryonated chicken eggs of the 10s virus as compared to WT PR8 virus. (E) HA assay of the 10s virus as compared to WT PR8 virus. (F) The "DI Units" of the 10s virus as compared to that of WT PR8 virus, calculated by dividing normalized HA units by normalized endpoint titer. For all graphs, * represents a p-value of ≤0.05 and ** represents a p-value of ≤0.001.
Figure 4:
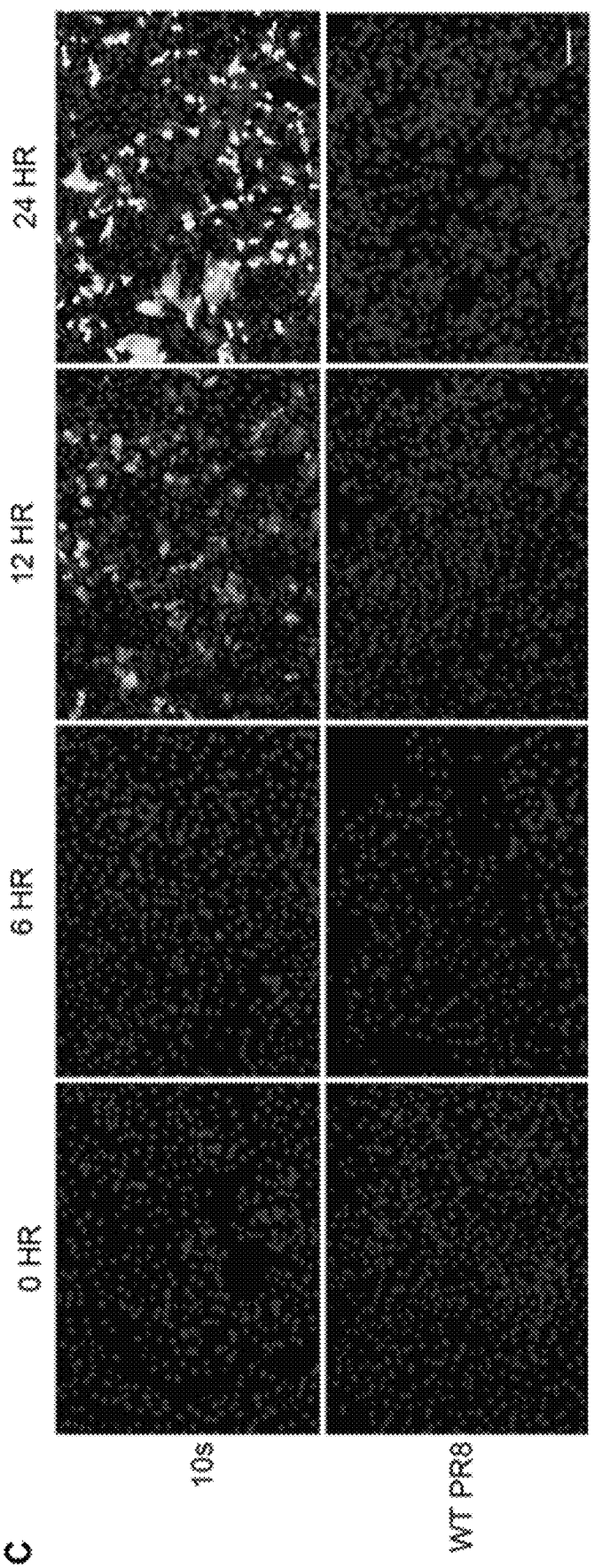
Figure 4:
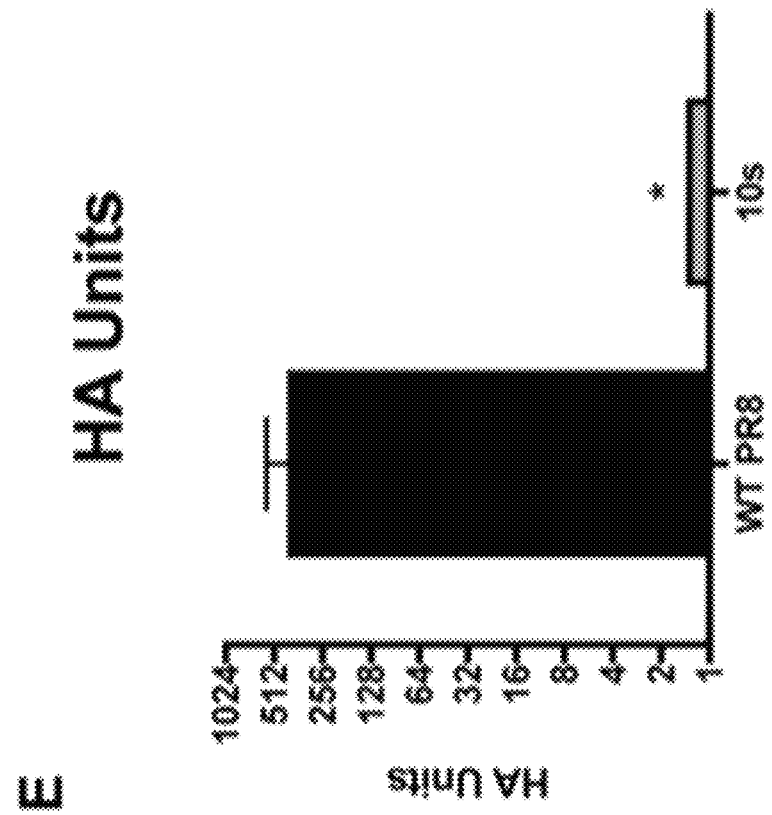
Figure 4:
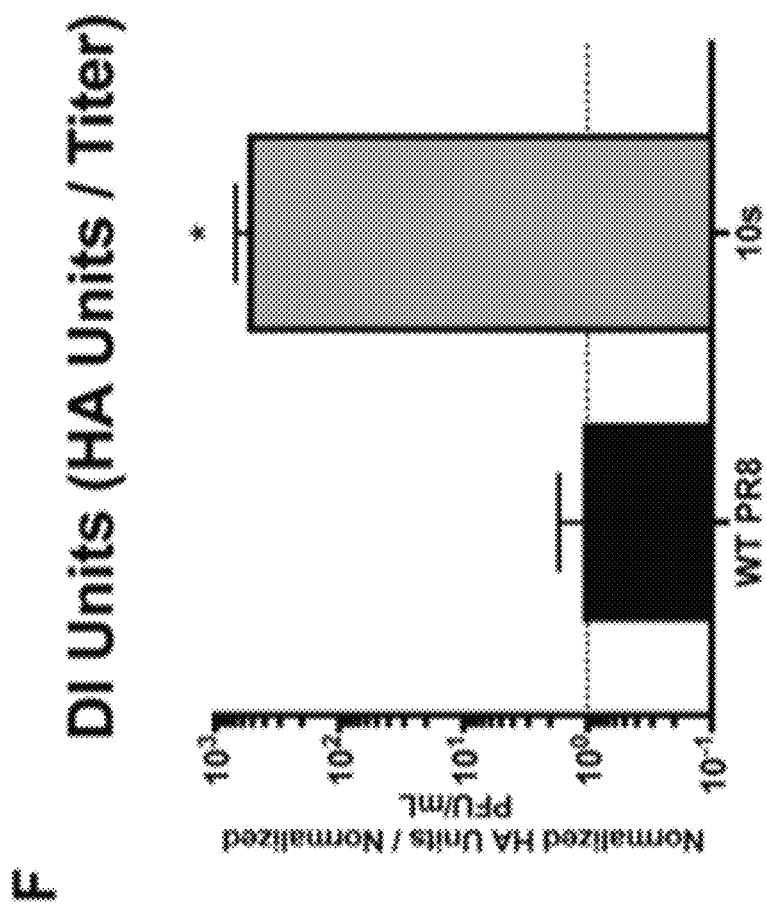

10-Segmented IAVs are Viable and Their Administration Can Rescue Infected Animals From Lethal Viral Disease Since the size of the DI segment did not appear to play a critical role in interfering with viral replication/packaging, we hypothesized that potentially increasing the number of segments would increase the ability of the virus to interfere with WT viral spread. Given that we able to successfully utilize two 9S genome packaging strategies, that utilized distinct packaging signal duplications, to generate two different viable 9S IAV variants, we considered the possibility of combining the two to generate a viable 10S IAV. Indeed, these two strategies were compatible, and we were successful in rescuing a 10S IAV harboring 6 WT segments alongside four genetically manipulated ones (FIG. 4A). Growth curve analysis of the 10S virus shows it is extremely attenuated, even more than the 9S viruses (FIG. 4B). A fluorescent microscopy time course of the 10S virus revealed that virus indeed functionally co-packaged both of the fluorescent artificial segments at all timepoints (FIG. 4C). Analysis of viral titer and HA units after growth in chicken eggs demonstrated that the 10S virus, while highly attenuated, produced a significantly higher ratio of nonviable progeny, nearly $10^3$ times higher than WT PR8 virus (FIG. 4D-4F).

Figure 5:
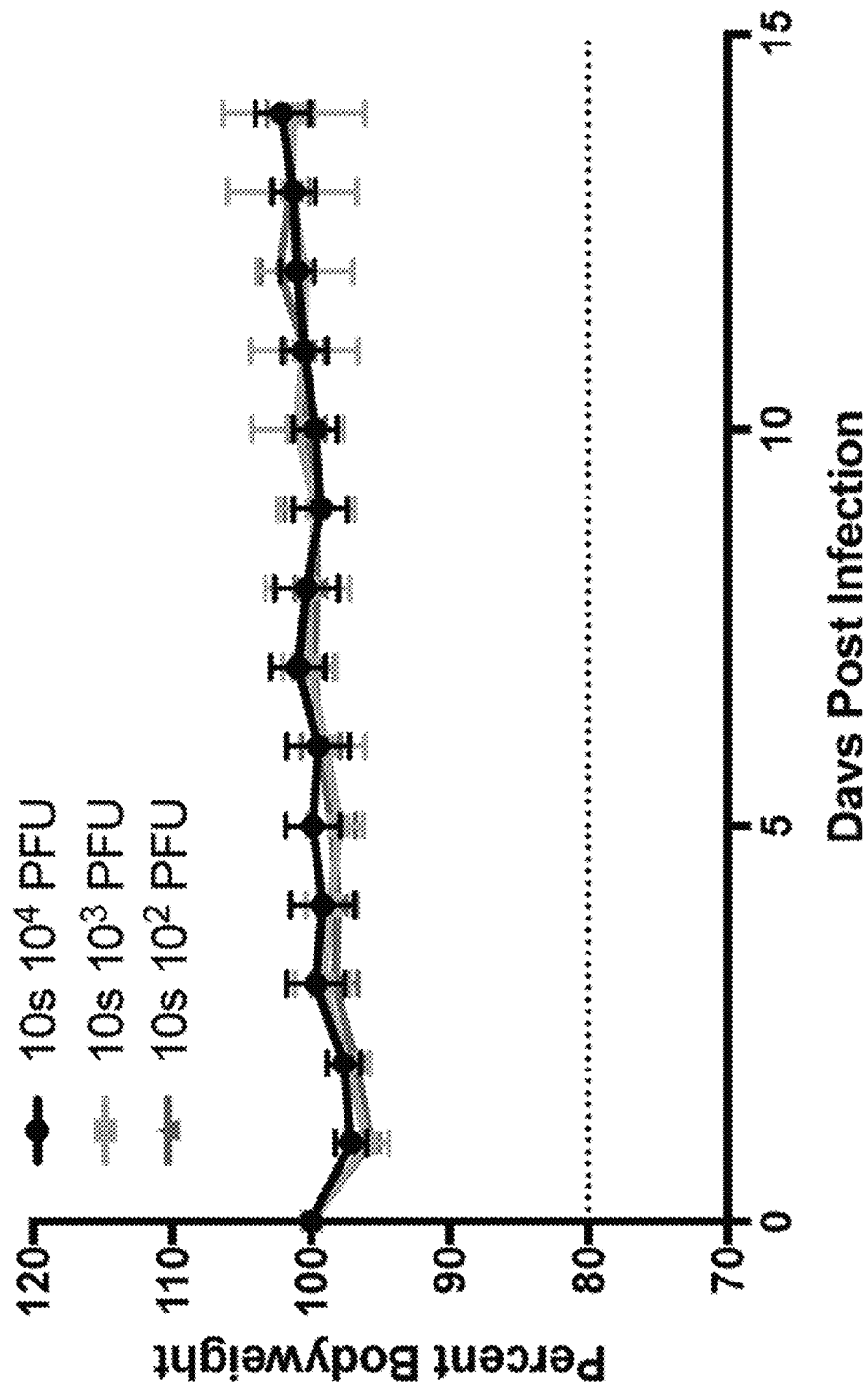
FIG. 5. 10-Segmented influenza viruses are highly attenuated and protect from lethal viral challenge when administered therapeutically. (A) Weight loss curves from infections with the indicated doses of 10s virus. (B) Survival curves from infections with the indicated doses of 10s virus. (C) Schema of C57BL/6J coinfection challenge at D0. (D) Weight loss curves from infecting mice with a sublethal dose of the 10s virus ((▲), 5000 PFU), a lethal dose of WT PR8 ((●), 20 PFU), or a lethal dose of WT PR8 virus in combination with 5000 PFU 10s virus (○). (E) Survival curves from the infection groups described in panel D. (F) Schema of C57BL/6J therapeutic 10s administration at 24 hours post-infection with lethal dose of WT PR8 virus. (G) Weight loss curves from infecting mice with a sublethal dose of the 10s virus ((▲), 5000 PFU), a lethal dose of WT PR8 ((●), 20 PFU), or a lethal dose of WT PR8 virus in combination with a dose of 5000 PFU 10s virus administered 24 hours later (○). (H) Survival curves from the infection groups described in panel G.
Figure 5:
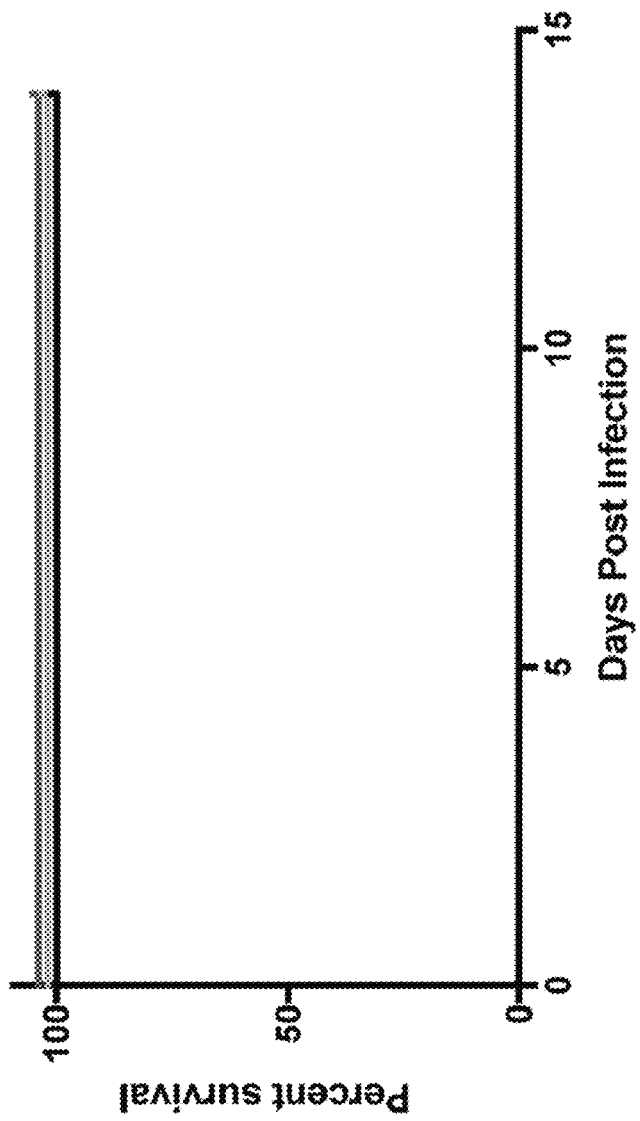
Figure 5:
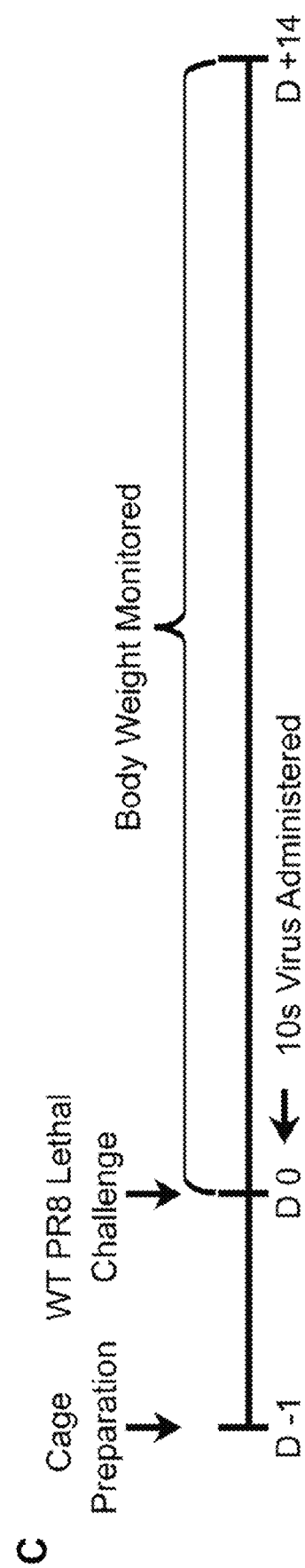
Figure 5:
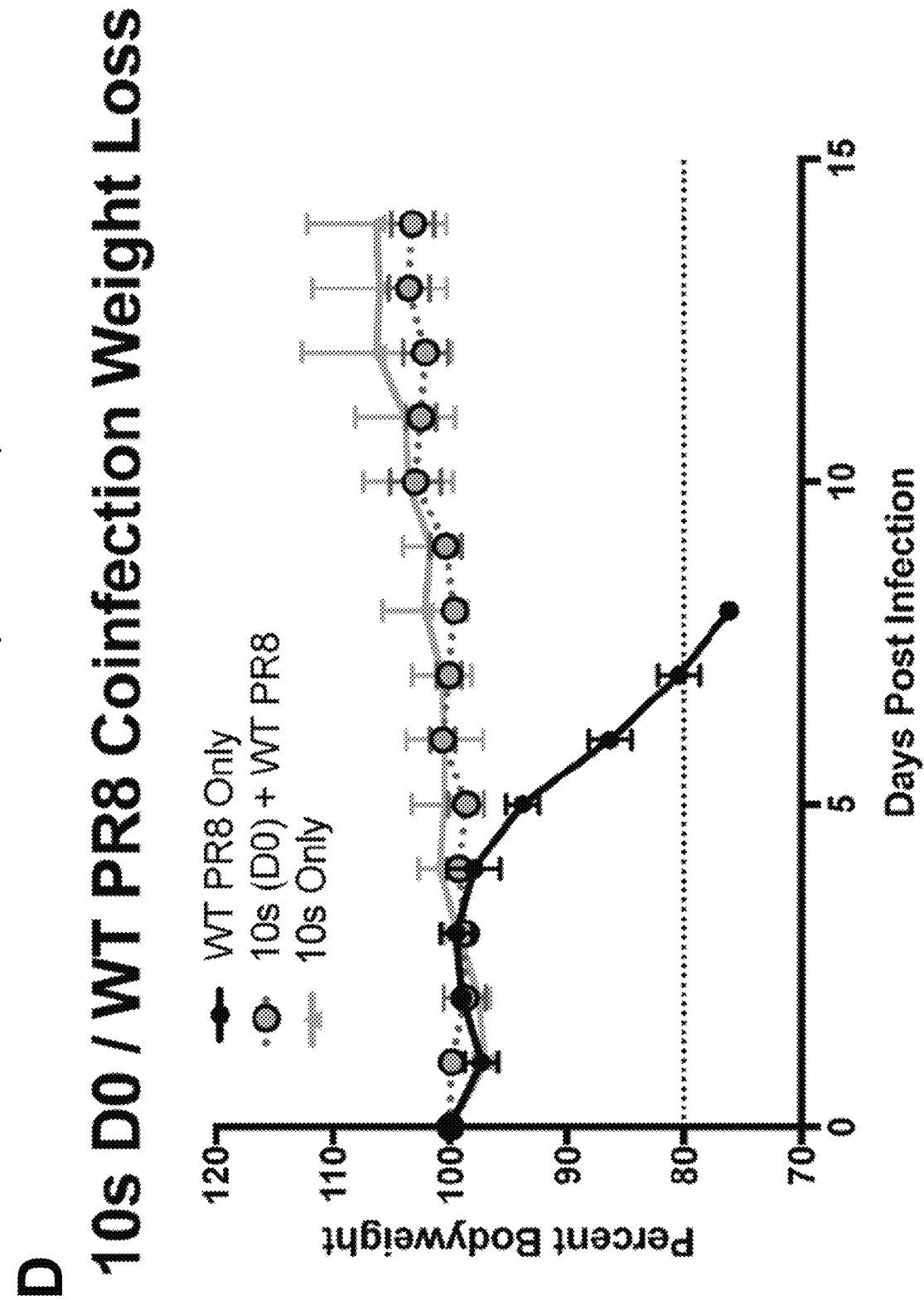
Figure 5:
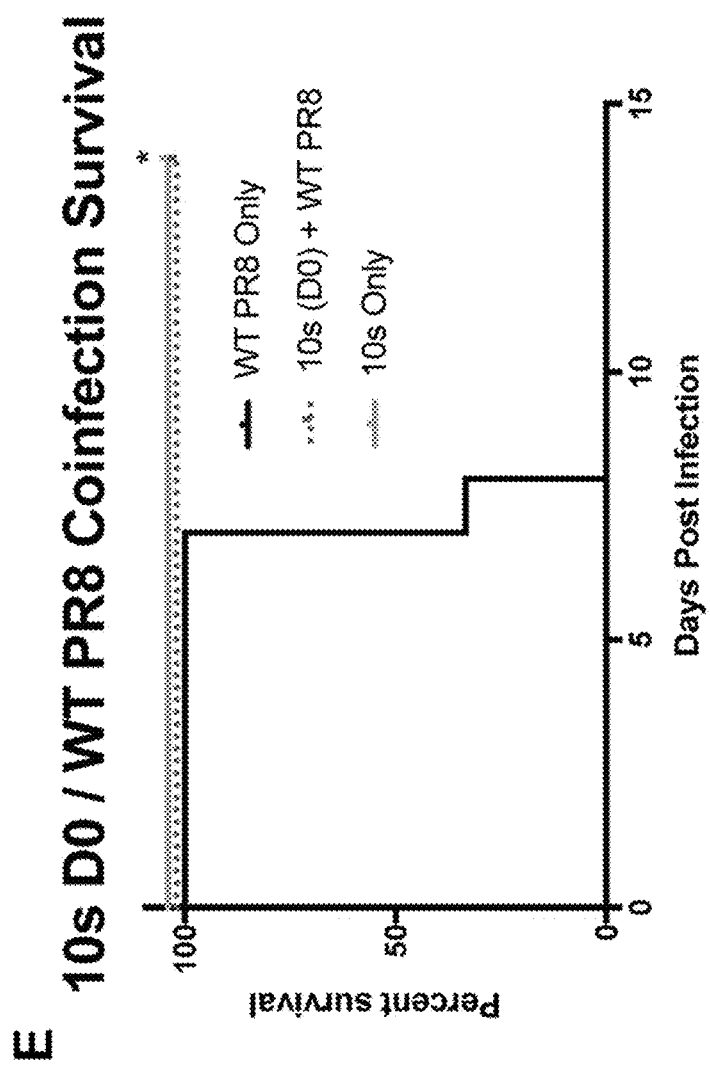
Figure 5:
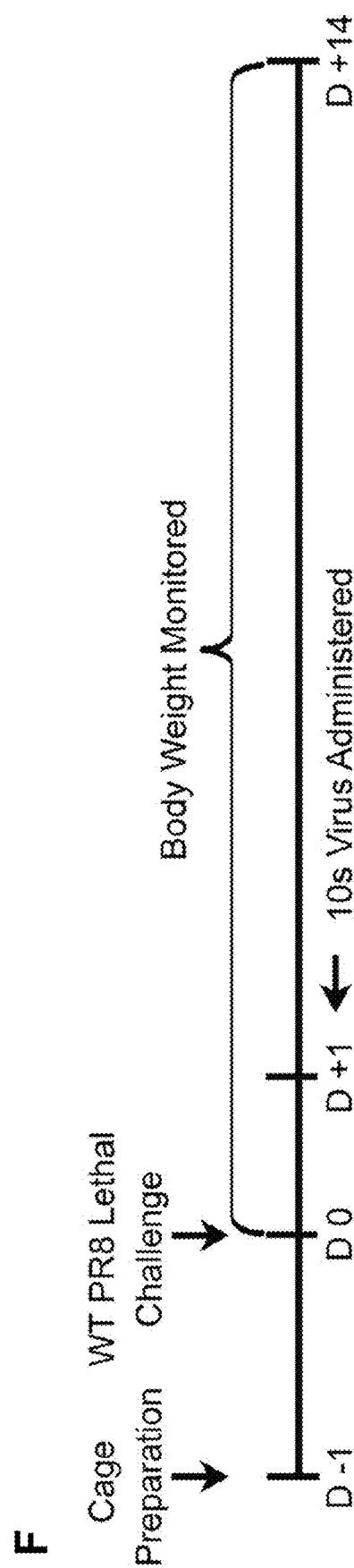
Figure 5:
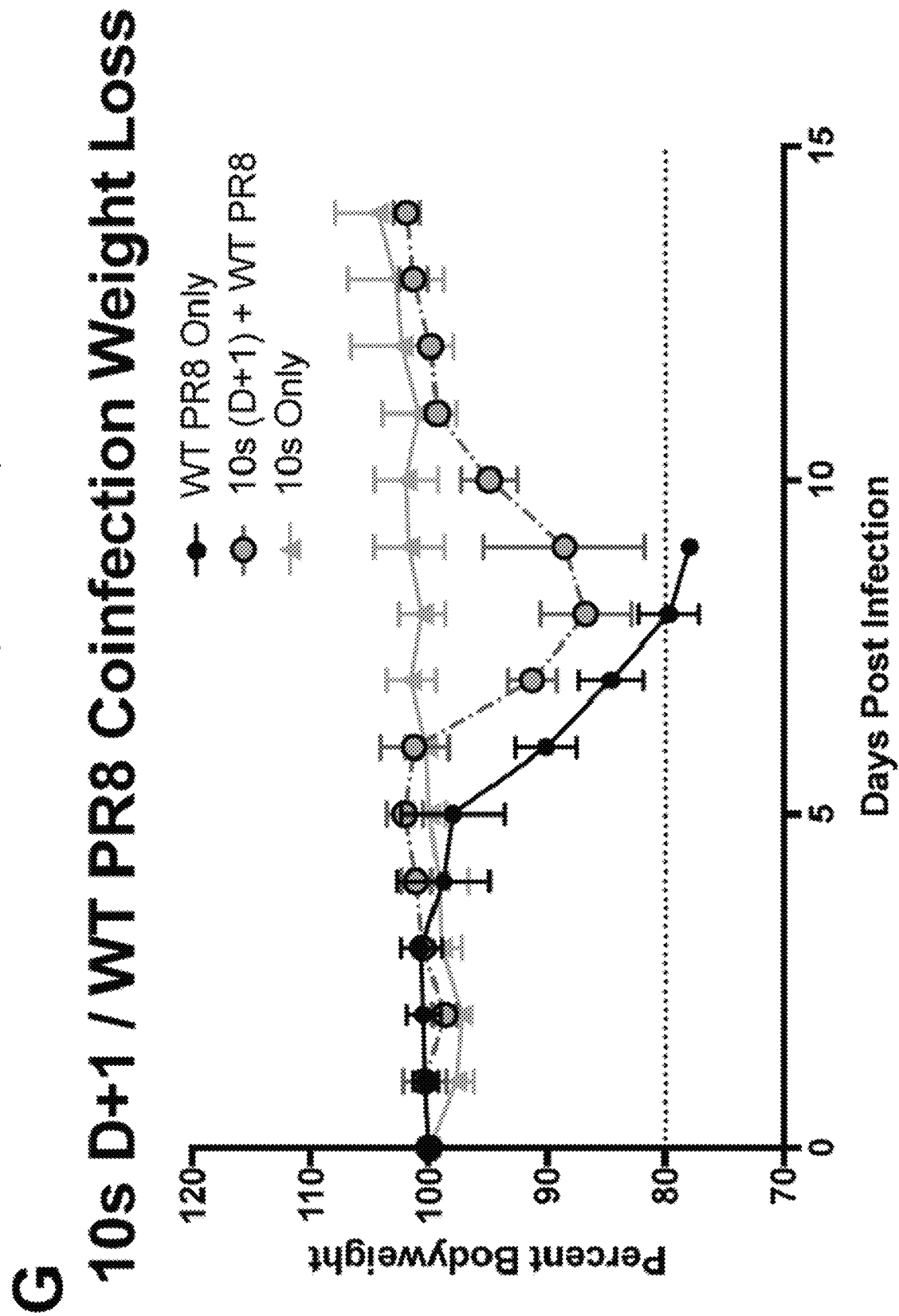
Figure 5:
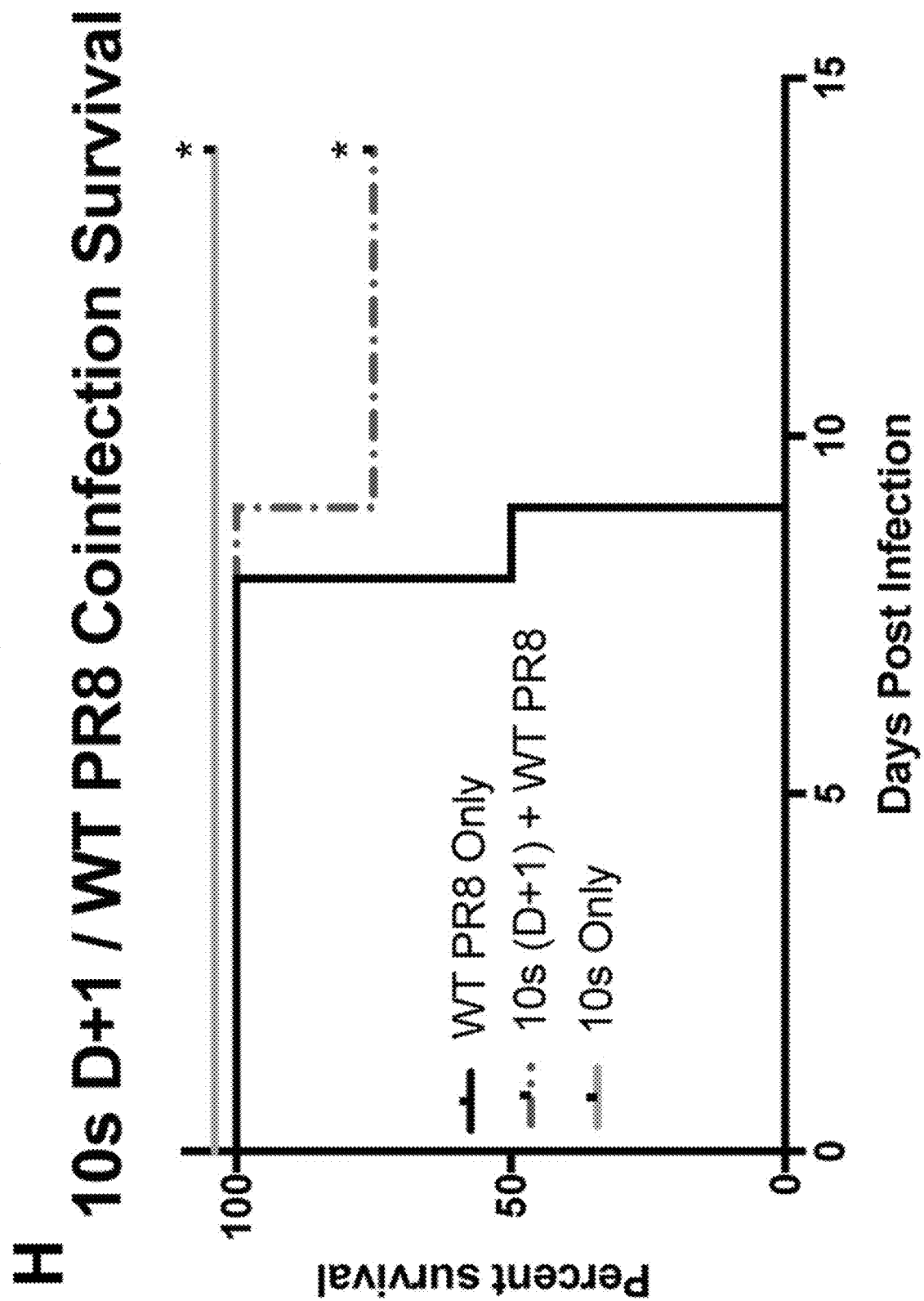

Next, we assessed the virulence of the 10S virus via an LD50 experiment in C57BL/6 mice. The virus was highly attenuated; animals infected with doses as high as $10^4$ PFU, which caused mortality when using any of the 9S viruses, experienced no detectable decline in body weight and all survived (FIG. 5A-5B). This increased attenuation is highly desirable when considering its use as a potential antiviral therapeutic. We were concerned, however, that this attenuated replication level would be too low to demonstrate any protective efficacy against WT IAV. As an initial test of the potential efficacy of a 10S virus as an antiviral agent, we challenged C57BL/6 mice with 20 PFU of WT PR8 virus in combination with 5000 PFU of the 10S virus (FIG. 5C). Remarkably, animals infected with both WT PR8 virus and 10S virus exhibited no detectable weight loss, whereas WT PR8 only infected control animals began to lose body weight as early as 5 days post-infection (FIG. 5D). All of the 10S treated animals survived the infection, whereas all of the WT PR8 only infected animals succumbed (FIG. 5E). We were next curious to assess 10S virus efficacy in more authentic therapeutic application. We therefore infected mice with a lethal dose of 20 PFU of WT PR8 virus, administered the 10S therapeutic dose 24 hours later, and then monitored animals for weight loss for 14 days post-infection (FIG. 5F). While the 10S virus treatment 24 hours after WT infection was not as effective as a simultaneous coinfection, we did observe a significant reduction in weight loss of the 10S treated animals, when compared to animals infected with WT PR8 alone (FIG. 5G). Furthermore, animals that were administered the 10S virus at 24 hours after WT PR8 infection had a significantly increased survival rate, 25% mortality versus 100% mortality, when compared to control WT PR8 only infected animals (FIG. 5II). Thus, we have developed an approach to generate viable 10S viruses and have shown that administration of 10S viruses either at the time of infection with WT IAV, or up to 24 h later, can effectively prevent, lethal influenza virus disease.

Discussion

This research was initially started with the goal of creating a replication competent, live attenuated virus that would be able to encode genomic segments capable of disrupting effective genomic packaging of a co-infecting WT virus. Our approach is mechanistically distinct from naturally occurring DI particles, which are naturally generated via large deletions of a viral segment. The 10S platform however, essentially mimics the concept of facilitating packaging of a defective viral segment, which then leads to the release of virions bearing incomplete viral genomes. In order to produce this virus, we first verified that a previously published approach of duplicating the NA segment packaging signals could be utilized to make the virus encode a $9^{th}$ genomic segment [51]. We next expanded upon that work and tested a variety of other genomic organizations and found that only rare combinations of viral genes and packaging signals were able to be tolerated by the virus. There are probably a number of constraints that underlie this phenomenon. First there is known to be a hierarchy of viral segment packaging [9], and thus, some segments (distinguished by the virus based on the packaging signals) may be less tolerant of duplication than others and lead to a disruption of the structure/assembly of the IAV genome. In line with this concept, work using 7-segmented influenza viruses has demonstrated that the requirement for different packaging signals is variable with respect to viral assembly [52]. Interestingly, this earlier work demonstrated that both the NA and PA packaging signals are not required for the packaging of the other genomic segments. Our ability to duplicate both of those packaging signals agrees with the concept that these particular packaging signals play a relatively less important role in viral assembly.

The 7-segmented virus work however, does not necessarily predict the ability of a given packaging signal to be duplicated. For example, NS packaging signals were also shown to be dispensable, yet we were unable to rescue a virus with duplicated NS packaging signals (Table 1). This discrepancy may be explained by the fact that the levels of transcription and translation of these viral segments is controlled by motifs in these specific segments [53, 54], and thus the combination of different viral ORFs and packaging signals leads to a disruption of the normal controllers of viral transcription/translation rates, negatively impacting viral fitness. This concept is somewhat supported by our data that a virus encoding the PB2 protein flanked by NP packaging signals is non-viable; NP is expressed in cells to a much higher level than PB2. When we encoded PB2 flanked by PA packaging signals however, the virus was viable, and PA and PB2 levels in the infected cell are reasonably similar [55].

To our knowledge, 9S viruses had never previously been tested for their ability to interfere with IAV disease progression, and we therefore decided to test our 9S viruses in that capacity. We chose to administer these viruses at the time of infection with a lethal dose of WT virus as a reasonably stringent test for potential efficacy of the approach. Disappointingly, only one of our 9S viruses displayed any protective efficacy, and the effect was limited. In order to try and improve the ability of our artificial viral segments to titrate viral RdRPs away from WT genomic segments, we made the artificial segment much smaller. Naturally occurring defective interfering viral segments are much smaller than our fluorescent protein encoding artificial $9^{th}$ segments, and we therefore generated a 9S virus harboring a segment that was more similar in size to naturally occurring DI segments [38]. While we were able to generate viruses that harbored these DI like segments, we found that the reduction in segment size led to very little, if any, improvement in efficacy. Although these insights are derived from a highly artificial system, our data suggest that it may be interesting to reevaluate the relative importance of segment length in the context of naturally occurring DI particles.

Since varying the artificial segment size was not correlated with protection from IAV, we hypothesized that the efficacy of our approach was instead dependent on the efficiency of packaging of our artificial genome segments by WT viruses, leading to progeny virions with incomplete genomes. Were that the case, making a virus which encoded more artificial segments could potentially confer higher protective efficacy. We therefore produced a 10S IAV that possessed 2 artificial genome segments instead of 1. Since our two validated genetic approaches were compatible with each other (i.e. different segments and packaging signals were utilized in the two approaches), we attempted to combine our 9s PB1 mCherry and 9s PB2 sfGFP virus strategies to produce a 10S virus. This effort was successful, resulting in the first known report of a stable 10S IAV. Although the growth rates of 10S viruses were significantly reduced relative to both WT and 9S viruses, the protective effect observed was far superior to that seen with any of the 9S viruses. When administered at the same time of infection, 100% of our treated mice survived a normally lethal dose of WT PR8 while exhibiting no detectable weight loss. While the effect of truly therapeutic administration 24 HPI had a less striking effect, we were still able to significantly delay the onset of clinical symptoms and reduce mortality rates by up to 75%.

Aside from the therapeutic potential of the 10s virus, its generation raises a multitude of interesting questions that warrant additional study. Perhaps most obvious is the question of IAV genome architecture. It is well accepted that IAVs package their segments in a "pinwheel" or 7+1 conformation, wherein a single segment, most likely one of the polymerase segments based on its size, is packaged in the center with the remaining 7 segments arranged around it in a circular shape [56]. The genomic architecture of both 9S and 10S IAVs, however, has not yet been evaluated. Understanding how the addition of one, or even two, segments impacts this structure could lead to a much better comprehension of both its assembly and stability during IAV packaging. Along these same lines, it has been shown that these genomic segments are tightly organized within the viral particle, leaving little room for excess genomic material [57]. The ability to generate 9S viruses, let alone 10S, viruses raises important questions as to the maximum amount of genetic material IAV virions can hold. This becomes an especially important question when considering the potential for utilizing influenza viruses as viral vectors, a platform that has been used for delivering a wide variety of proteins and nucleic acids [58].

Finally, the fact that 9S and 10S viruses can interfere with WT viral propagation strongly supports the notion that cellular co-infection is a common occurrence in vivo. Despite the historical notion that most viral particles are fully infectious, likely due to the fact that IAV particles package all eight genomic segments the majority of the time [59, 60], recent work has suggested that co-infection may actually be not only a frequent occurrence that allows viral reassortment [61], but also a critical aspect of normal viral spread across infected tissues [62]. Since our 9S or 10S interfering effects are dependent on co-infection with WT viruses, we not only favor this model, but propose that even distinct viral infections that begin at different times are also subject to this co-infection phenomenon.

In summary, we have successfully defined genomic architectures that allow influenza viruses to harbor up to two additional, artificial segments. Our work suggests that not all IAV packaging signals are amenable to manipulations such as duplication, and that the particular characteristics of a "defective" viral segment are not as important to its interfering effect as the absolute number of segments that can disrupt productive genomic packaging. Continued development of the 10-segmented replication-competent IAV platform may lead to a novel class of therapeutics that can be easily manufactured, safely administered, and display protective efficacy against viruses that have evolved resistance to other antiviral therapies.

REFERENCES

1. WHO. Influenza (Seasonal): The World Health Organization 2018 [updated January 2018 Nov. 13, 2018]. Available from: http://www.who.int/mediacentre/factsheets/fs211/en/.
2. Iuliano A D, Roguski K M, Chang H H, Muscatello D J, Palekar R, Tempia S, et al. Estimates of global seasonal influenza-associated respiratory mortality: a modelling study. Lancet. 2018; 391(10127):1285-300. Epub 2017 Dec. 19. doi: 10.1016/S0140-6736(17)33293-2. PubMed PMID: 29248255; PubMed Central PMCID: PMCPMC5935243.
3. Putri W, Muscatello D J, Stockwell M S, Newall A T. Economic burden of seasonal influenza in the United States. Vaccine. 2018; 36(27):3960-6. Epub 2018 May 29. doi: 10.1016/j.vaccine.2018.05.057. PubMed PMID: 29801998.
4. Shaw M L, Palese P. Orthomyxoviruses. In: Knipe D M, Howley P M, editors. Fields Virology. Philadelphia: Lippincott Williams and Wilkins; 2013. p. 1151-85.
5. Eisfeld A J, Neumann G, Kawaoka Y. At the centre: influenza A virus ribonucleoproteins. Nat Rev Microbiol. 2015; 13(1):28-41. Epub 2014 Nov. 25 doi: 10.1038/nrmicro3367. PubMed PMID: 25417656; PubMed Central PMCID: PMCPMC5619696.
6. Fujii K, Fujii Y, Noda T, Muramoto Y, Watanabe T, Takada A, et al. Importance of both the coding and the segment-specific noncoding regions of the influenza A virus NS segment for its efficient incorporation into virions. J Virol. 2005; 79(6):3766-74. doi: 10.1128/jvi.79.6.3766-3774.2005. PubMed PMID: 15731270; PubMed Central PMCID: PMCPMC1075679.
7. Goto H, Muramoto Y, Noda T, Kawaoka Y. The genome-packaging signal of the influenza A virus genome comprises a genome incorporation signal and a genome-bundling signal. J Virol. 2013; 87(21):11316-22. Epub 2013 Aug. 9. doi: 10.1128/JVI.01301-13. PubMed PMID: 23926345; PubMed Central PMCID: PMCPMC3807325.
8. Liang Y, Hong Y, Parslow T G. cis-Acting packaging signals in the influenza virus PB1, PB2, and PA genomic RNA segments. J Virol. 2005; 79(16):10348-55. doi: 10.1128/jvi.79.16.10348-10355.2005. PubMed PMID: 16051827; PubMed Central PMCID: PMCPMC1182667.
9. Muramoto Y, Takada A, Fujii K, Noda T, Iwatsuki-Horimoto K, Watanabe S, et al. Hierarchy among viral RNA (vRNA) segments in their role in vRNA incorporation into influenza A virions. J Virol. 2006; 80(5):2318-25. Epub 2006 Feb. 14. doi: 10.1128/JVI.80.5.2318-2325.2006. PubMed PMID: 16474138; PubMed Central PMCID: PMCPMC1395381.
10. Marsh G A, Hatami R, Palese P. Specific Residues of the Influenza A Virus Hemagglutinin Viral RNA Are Important for Efficient Packaging into Budding Virions. Journal of Virology. 2007; 81(18):9727-36. doi: 10.1128/jvi.01144-07.
11. Hutchinson E C, Curran M D, Read E K, Gog J R, Digard P. Mutational analysis of cis-acting RNA signals in segment 7 of influenza A virus. Journal of virology. 2008; 82(23):11869-79. Epub September 24. doi: 10.1128/JVI.01634-08. PubMed PMID: 18815307.
12. Dadonaite B, Barilaite E, Fodor E, Laederach A, Bauer D L. The structure of the influenza A virus genome. bioRxiv. 2017:236620. doi: 10.1101/236620.
13. Lee N, Le Sage V, Nanni A V, Snyder D J, Cooper V S, Lakdawala S S. Genome-wide analysis of influenza viral RNA and nucleoprotein association. Nucleic acids research. 2017; 45(15):8968-77. Epub July 7. doi: 10.1093/nar/gkx584. PubMed PMID: 28911100.
14. Williams G D, Townsend D, Wylie K M, Kim P J, Amarasinghe G K, Kutluay S B, et al. Nucleotide resolution mapping of influenza A virus nucleoprotein-RNA interactions reveals RNA features required for replication. Nature Communications. 2018; 9(1):465. doi: 10.1038/s41467-018-02886-w.
15. Gavazzi C, Yver M, Isel C, Smyth R P, Rosa-Calatrava M, Lina B, et al. A functional sequence-specific interaction between influenza A virus genomic RNA segments. Proceedings of the National Academy of Sciences. 2013; 110(41):16604-9. doi: 10.1073/pnas.1314419110.
16. Fournier E, Moules V, Essere B, Paillart J-C, Sirbat J-D, Cavalier A, et al. Interaction network linking the human H3N2 influenza A virus genomic RNA segments. Vaccine. 2012; 30(51):7359-67.
17. Hutchinson E C, von Kirchbach J C, Gog J R, Digard P. Genome packaging in influenza A virus. J Gen Virol. 2010; 91(Pt 2):313-28. Epub 2009 Dec. 4. doi: 10.1099/vir.0.017608-0. PubMed PMID: 19955561.
18. Noda T, Sugita Y, Aoyama K, Hirase A, Kawakami E, Miyazawa A, et al. Three-dimensional analysis of ribonucleoprotein complexes in influenza A virus. Nature Communications. 2012; 3:639.
19. Gog J R, Afonso E D S, Dalton R M, Leclercq I, Tiley L, Elton D, et al. Codon conservation in the influenza A virus genome defines RNA packaging signals. Nucleic Acids Research. 2007; 35(6):1897-907. doi: 10.1093/nar/gkm087.
20. Gerber M, Isel C, Moules V, Marquet R. Selective packaging of the influenza A genome and consequences for genetic reassortment. Trends in microbiology. 2014; 22(8):446-55. Epub 2014 May 7. doi: 10.1016/j.tim.2014.04.001. PubMed PMID: 24798745.
21. Hussain M, Galvin H D, Haw T Y, Nutsford A N, Husain M. Drug resistance in influenza A virus: the epidemiology and management. Infect Drug Resist. 2017; 10:121-34. Epub 2017 May 2. doi: 10.2147/IDR.S105473. PubMed PMID: 28458567; PubMed Central PMCID: PMCPMC5404498.
22. Dong G, Peng C, Luo J, Wang C, Han L, Wu B, et al. Adamantane-resistant influenza a viruses in the world (1902-2013): frequency and distribution of M2 gene mutations. PLoS One. 2015; 10(3):e0119115. Epub 2015 Mar. 15. doi: 10.1371/journal.pone.0119115. PubMed PMID: 25768797; PubMed Central PMCID: PMCPMC4358984.
23. Bright R A, Medina M J, Xu X Y, Perez-Oronoz G, Wallis T R, Davis X H M, et al. Incidence of adamantane resistance among influenza A (H3N2) viruses isolated worldwide from 1994 to 2005: a cause for concern. Lancet. 2005; 366(9492):1175-81.
24. Garten R, Blanton L, Elal A I A, Alabi N, Barnes J, Biggerstaff M, et al. Update: Influenza Activity in the United States During the 2017-18 Season and Composition of the 2018-19 Influenza Vaccine. MMWR Morb Mortal Wkly Rep. 2018; 67(22):634-42. Epub 2018 Jun. 8. doi: 10.15585/mmwr.mm6722a4. PubMed PMID: 29879098; PubMed Central PMCID: PMCPMC5991814.
25. Moscona A. Neuraminidase Inhibitors for Influenza. New England Journal of Medicine. 2005; 353(13):1363-73. doi: 10.1056/NEJMra050740.
26. Bloom J D, Gong L I, Baltimore D. Permissive Secondary Mutations Enable the Evolution of Influenza Oselta- 27. Sheu T G, Deyde V M, Okomo-Adhiambo M, Garten R J, Xu X, Bright R A, et al. Surveillance for neuraminidase inhibitor resistance among human influenza A and B viruses circulating worldwide from 2004 to 2008. Antimicrob Agents Chemother. 2008; 52(9):3284-92. doi: 10.1128/aac.00555-08. PubMed PMID: WOS: 000258667300039.

28. Monto A S, McKimm-Breschkin J L, Macken C, Hampson A W, Hay A, Klimov A, et al. Detection of influenza viruses resistant to neuraminidase inhibitors in global surveillance during the first 3 years of their use. Antimicrob Agents Chemother. 2006; 50(7):2395-402. doi: 10.1128/aac.01339-05. PubMed PMID: WOS: 000238721200016.

29. Takashita E, Meijer A, Lackenby A, Gubareva L, Rebelo-de-Andrade H, Besselaar T, et al. Global update on the susceptibility of human influenza viruses to neuraminidase inhibitors, 2013-2014. Antiviral Res. 2015; 117:27-38. doi: 10.1016/j.antiviral.2015.02.003. PubMed PMID: WOS:000353734800004.

30. Nguyen H T, Fry A M, Gubareva L V. Neuraminidase inhibitor resistance in influenza viruses and laboratory testing methods. Antivir Ther. 2012; 17(1):159-73. doi: 10.3851/imp2067. PubMed PMID: WOS: 000303653400004.

31. Bank S. New treatments for influenza. BMC Med. 2012; 10:104. Epub 2012 Sep. 15. doi: 10.1186/1741-7015-10-104. PubMed PMID: 22973873; PubMed Central PMCID: PMCPMC3523090.

32. Mullard A. FDA approves first new flu drug in 20 years. Nat Rev Drug Discov. 2018; 17(12):853. Epub 2018 Nov. 30. doi: 10.1038/nrd.2018.219. PubMed PMID: 30482963.

33. Dimmock N J, Easton A J. Defective interfering influenza virus RNAs: time to reevaluate their clinical potential as broad-spectrum antivirals? J Virol. 2014; 88(10): 5217-27. Epub 2014 Feb. 28. doi: 10.1128/JVI.03193-13. PubMed PMID: 24574404; PubMed Central PMCID: PMCPMC4019098.

34. Sun Y, Jain D, Koziol-White C J, Genoyer E, Gilbert M, Tapia K, et al. Immunostimulatory Defective Viral Genomes from Respiratory Syncytial Virus Promote a Strong Innate Antiviral Response during Infection in Mice and Humans. PLoS pathogens. 2015; 11(9):e1005122. Epub 2015 Sep. 4. doi: 10.1371/journal.ppat.1005122. PubMed PMID: 26336095; PubMed Central PMCID: PMCPMC4559413.

35. Yount J S, Kraus T A, Horvath C M, Moran T M, Lopez C B. A novel role for viral-defective interfering particles in enhancing dendritic cell maturation. Journal of immunology (Baltimore, Md: 1950). 2006; 177(7):4503-13. Epub 2006 Sep. 20. PubMed PMID: 16982887.

36. Li D, Lott W B, Lowry K, Jones A, Thu H M, Aaskov J. Defective interfering viral particles in acute dengue infections. PLoS One. 2011; 6(4):e19447. Epub 2011 May 12. doi: 10.1371/journal.pone.0019447. PubMed PMID: 21559384; PubMed Central PMCID: PMCPMC3084866.

37. Davis A R, Hiti A L, Nayak D P. Influenza defective interfering viral RNA is formed by internal deletion of genomic RNA. Proc Natl Acad Sci USA. 1980; 77(1): 215-9. Epub 1980 Jan. 1. PubMed PMID: 6928614; PubMed Central PMCID: PMCPMC348239.

38. Saira K, Lin X, DePasse J V, Halpin R, Twaddle A, Stockwell T, et al. Sequence analysis of in vivo defective interfering-like RNA of influenza A H1N1 pandemic virus. J Virol. 2013; 87(14):8064-74. Epub 2013 May 17. doi: 10.1128/JVI.00240-13. PubMed PMID: 23678180; PubMed Central PMCID: PMCPMC3700204.

39. Brooke C B. Population Diversity and Collective Interactions during Influenza Virus Infection. J Virol. 2017; 91(22). Epub 2017 Sep. 1. doi: 10.1128/JVI.01164-17. PubMed PMID: 28855247; PubMed Central PMCID: PMCPMC5660503.

40. Diefenbacher M, Sun J, Brooke C B. The parts are greater than the whole: the role of semi-infectious particles in influenza A virus biology. Curr Opin Virol. 2018; 33:42-6. Epub 2018 Jul. 28. doi: 10.1016/j.coviro.2018.07.002. PubMed PMID: 30053722.

41. Laske T, Heldt F S, Hoffmann H, Frensing T, Reichl U. Modeling the intracellular replication of influenza A virus in the presence of defective interfering RNAs. Virus Research. 2016; 213:90-9. doi: https://doi.org/10.1016/j.virusres.2015.11.016.

42. Lamb R A, Choppin P W. The Gene Structure and Replication of Influenza Virus. Annual Review of Biochemistry. 1983; 52(1):467-506. doi: 10.1146/annurev.bi.52.070183.002343. PubMed PMID: 6351727.

43. Huang A S, Palma E L. Chapter 4—Defective Interfering Particles As Antiviral Agents. In: Pollard M, editor. Perspectives in Virology. 9: Elsevier; 1975. p. 77-90.

44. Noble S, McLain L, Dimmock N J. Interfering vaccine: a novel antiviral that converts a potentially virulent infection into one that is subclinical and immunizing. Vaccine. 2004; 22(23-24):3018-25. doi: 10.1016/j.vaccine.2004.02.013. PubMed PMID: 15297051.

45. Dimmock N J, Rainsford E W, Scott P D, Marriott A C. Influenza virus protecting RNA: an effective prophylactic and therapeutic antiviral. J Virol. 2008; 82(17):8570-8. Epub 2008 Jun. 27. doi: 10.1128/JVI.00743-08. PubMed PMID: 18579602; PubMed Central PMCID: PMCPMC2519629.

46. Dimmock N J, Dove B K, Scott P D, Meng B, Taylor I, Cheung L, et al. Cloned defective interfering influenza virus protects ferrets from pandemic 2009 influenza A virus and allows protective immunity to be established. PLoS One. 2012; 7(12):e49394. Epub 2012 Dec. 20. doi: 10.1371/journal.pone.0049394. PubMed PMID: 23251341; PubMed Central PMCID: PMCPMC3521014.

47. Smith C M, Scott P D, O'Callaghan C, Easton A J, Dimmock N J. A Defective Interfering Influenza RNA Inhibits Infectious Influenza Virus Replication in Human Respiratory Tract Cells: A Potential New Human Antiviral. Viruses. 2016; 8(8). Epub 2016 Aug. 25. doi: 10.3390/v8080237. PubMed PMID: 27556481; PubMed Central PMCID: PMCPMC4997599.

48. von Magnus P. Incomplete Forms of Influenza Virus. In: Smith K M, Lauffer M A, editors. Advances in Virus Research. 2: Academic Press; 1954. p. 59-79.

49. Holland J J. Generation and replication of defective viral genomes. In: Fields B N, Knipe D M, editors. Fields Virology. 2 ed. New York, NY: Raven Press; 1990. p. 77-99.

50. Wasik M A, Eichwald L, Genzel Y, Reichl U. Cell culture-based production of defective interfering particles for influenza antiviral therapy. Appl Microbiol Biotechnol. 2018; 102(3):1167-77. Epub 2017 Dec. 6. doi: 10.1007/s00253-017-8660-3. PubMed PMID: 29204901; PubMed Central PMCID: PMCPMC5778153.

51. Gao Q, Lowen A C, Wang T T, Palese P. A nine-segment influenza a virus carrying subtype H1 and H3 hemagglutinins. J Virol. 2010; 84(16):8062-71. Epub 2010 Jun. 4. doi: 10.1128/JVI.00722-10. PubMed PMID: 20519387; PubMed Central PMCID: PMCPMC2916553.
52. Gao Q, Chou Y-Y, Doğanay S, Vafabakhsh R, Ha T, Palese P. The Influenza A Virus PB2, PA, NP, and M Segments Play a Pivotal Role during Genome Packaging. Journal of Virology. 2012; 86(13):7043. doi: 10.1128/JVI.00662-12.
53. Shapiro G I, Gurney T, Jr., Krug R M. Influenza virus gene expression: control mechanisms at early and late times of infection and nuclear-cytoplasmic transport of virus-specific RNAs. J Virol. 1987; 61(3):764-73. Epub 1987 Mar. 1. PubMed PMID: 3806797; PubMed Central PMCID: PMCPMC254018.
54. Hatada E, Hasegawa M, Mukaigawa J, Shimizu K, Fukuda R. Control of influenza virus gene expression: quantitative analysis of each viral RNA species in infected cells. J Biochem. 1989; 105(4):537-46. Epub 1989 Apr. 1. PubMed PMID: 2760014.
55. Kummer S, Flottmann M, Schwanhausser B, Sieben C, Veit M, Selbach M, et al. Alteration of protein levels during influenza virus H1N1 infection in host cells: a proteomic survey of host and virus reveals differential dynamics. PLoS One. 2014; 9(4):e94257. Epub 2014 Apr. 11. doi: 10.1371/journal.pone.0094257. PubMed PMID: 24718678; PubMed Central PMCID: PMCPMC3981805.
56. Noda T, Sagara H, Yen A, Takada A, Kida H, Cheng R H, et al. Architecture of ribonucleoprotein complexes in influenza A virus particles. Nature. 2006; 439(7075):490-2. Epub 2006 Jan. 27. doi: 10.1038/nature04378. PubMed PMID: 16437116.
57. Noda T, Sugita Y, Aoyama K, Hirase A, Kawakami E, Miyazawa A, et al. Three-dimensional analysis of ribonucleoprotein complexes in influenza A virus. Nat Commun. 2012; 3:639. Epub 2012 Jan. 26. doi: 10.1038/ncomms1647. PubMed PMID: 22273677; PubMed Central PMCID: PMCPMC3272569.
58. Li J, Arevalo M T, Zeng M. Engineering influenza viral vectors. Bioengineered. 2013; 4(1):9-14. Epub 2012 Aug. 28. doi: 10.4161/bioe.21950. PubMed PMID: 22922205; PubMed Central PMCID: PMCPMC3566024.
59. Chou Y Y, Vafabakhsh R, Doganay S, Gao Q S, Ha T, Palese P. One influenza virus particle packages eight unique viral RNAs as shown by FISH analysis. P Natl Acad Sci USA. 2012; 109(23):9101-6. doi: 10.1073/pnas.1206069109. PubMed PMID: WOS:000304991100066.
60. Nakatsu S, Sagara H, Sakai-Tagawa Y, Sugaya N, Noda T, Kawaoka Y. Complete and Incomplete Genome Packaging of Influenza A and B Viruses. Mbio. 2016; 7(5).
61. Marshall N, Priyamvada L, Ende Z, Steel J, Lowen A C. Influenza Virus Reassortment Occurs with High Frequency in the Absence of Segment Mismatch. Plos Pathog. 2013; 9(6).
62. Jacobs N T, Onuoha N O, Anita A, Anita R, Steel J, Lowen A C. Incomplete influenza A virus genomes are abundant but readily complemented during spatially structured viral spread. bioRxiv. 2019. Epub Jan. 23, 2019. doi: https://doi.org/10.1101/529065.
63. Heaton N S, Leyva-Grado V H, Tan G S, Eggink D, Hai R, Palese P. In vivo bioluminescent imaging of influenza a virus infection and characterization of novel cross-protective monoclonal antibodies. J Virol. 2013; 87(15): 8272-81. Epub 2013 May 24. doi: 10.1128/JVI.00969-13. PubMed PMID: 23698304; PubMed Central PMCID: PMCPMC3719835.

What is claimed is:

1. A polynucleotide construct or set of constructs comprising:
   (i) a first domain comprising from 5' to 3': a 5' packaging signal of polymerase acid (PA), a polynucleotide sequence encoding polymerase basic subunit 2 (PB2), and a 3' packaging signal of PA;
   (ii) a second domain comprising from 5' to 3': a 5' packaging signal of PB2, a first heterologous polynucleotide sequence, and a 3' packaging signal of PB2; and
   (iii) a third domain comprising from 5' to 3': the 5' packaging signal of PA, a polynucleotide sequence encoding PA, and the 3' packaging signal of PA;
   wherein the construct or set of constructs can be used to produce a replication competent modified influenza A virus (IAV) having at least nine gene segments.

2. The polynucleotide construct or set of constructs of claim 1, further comprising:
   (iii) a fourth domain comprising from 5' to 3': a 5' packaging signal of neuraminidase (NA), a polynucleotide sequence encoding polymerase basic subunit 1 (PB1), and a 3' packaging signal of NA;
   (iv) a fifth domain comprising from 5' to 3': a 5' packaging signal of PB1, a second heterologous polynucleotide sequence, and a 3' packaging signal of PB1; and
   (v) a sixth domain comprising from 5' to 3': the 5' packaging signal of NA, a polynucleotide sequence encoding NA, and the 3' packaging signal of NA;
   wherein the construct or set of constructs can be used to produce a replication competent modified IA V having at least ten gene segments.

3. The polynucleotide construct or set of constructs of claim 1, further comprising at least six additional domains comprising wild-type viral segments encoding, hemagglutinin (HA), nucleoprotein (NP), neuraminidase (NA), matrix (M), PB1, and nonstructural protein (NS).

4. The polynucleotide construct or set of constructs of claim 2, wherein:
   the 5' packaging signal of PA is SEQ ID NO:1,
   the 3' packaging signal of PA is SEQ ID NO:2,
   the 5' packaging signal of PB1 is SEQ ID NO:5,
   the 3' packaging signal of PB1 is SEQ ID NO:6
   the 5' packaging signal of PB2 is SEQ ID NO:7;
   the 3' packaging signal of PB2 is SEQ ID NO:8;
   the 5' packaging signal of NA is SEQ ID NO:3, and/or
   the 3' packaging signal of NA is SEQ ID NO:4.

5. The polynucleotide construct or set of constructs of claim 1, wherein the polynucleotide sequence encoding PB2 comprises a disabled version of the 5' packaging signal of PB2 and a disabled version of the 3' packaging signal of PB2.

6. The polynucleotide construct or set of constructs of claim 2, wherein the polynucleotide sequence encoding PB1 comprises a disabled version of the 5' packaging signal of PB1 and a disabled version of the 3' packaging signal of PB1.

7. The polynucleotide construct or set of constructs of claim 2, wherein
   the first domain is SEQ ID NO: 12 or SEQ ID NO:14; and/or
   the fourth domain is SEQ ID NO:11.

8. A cultured cell comprising the polynucleotide construct or set of constructs of claim 1,
   wherein the cell produces a replication competent modified IAV having at least nine gene segments.

9. A cultured cell comprising the polynucleotide construct or set of constructs of claim 2,
   wherein the cell produces a replication competent modified IAV having at least ten gene segments.

10. A modified IAV produced by the cell of claim 8, wherein the modified IAV has at least nine gene segments.

11. The modified IAV of claim 10, wherein the modified IAV is replication competent.

12. A vaccine comprising the modified IAV of claim 10.

13. The vaccine of claim 12, wherein the vaccine is formulated for intramuscular or intranasal delivery.

14. A method of treating or reducing at least one symptom caused by an IAV infection in a subject, the method comprising administering to the subject a therapeutically effective amount of the modified IAV of claim 10.

15. The method of claim 14, wherein the subject is administered the modified IAV (a) after having contracted an IAV infection or (b) prior to showing symptoms of IAV infection.

16. The method of claim 14, wherein the modified IAV encodes (a) a heterologous influenza antigen or (b) an immunomodulatory protein.

17. A method of inducing an immune response in a subject to modified IAV and a heterologous antigen, the method comprising:
   administering an effective amount of the modified IAV of claim 10 to the subject, wherein the heterologous polynucleotide encodes the heterologous antigen.

18. The method of claim 17, wherein the heterologous antigen is from a virus, bacteria, fungus or parasite.

19. A kit comprising the polynucleotide construct or set of constructs of claim 1 and instructions.

20. The polynucleotide construct or set of constructs of claim 2, further comprising at least four additional domains comprising wild-type viral segments encoding HA, NP, M, and NS.

* * * * *

SEQUENCE LISTING

```
<160> NUMBER OF SEQ ID NOS: 17

<210> SEQ ID NO 1
<211> LENGTH: 129
<212> TYPE: DNA
<213> ORGANISM: Artificial Sequence
<220> FEATURE:
<223> OTHER INFORMATION: Synthetic- PA 5' packaging signal

<400> SEQUENCE: 1
agcgaaagca ggtactgatc caaattggaa gattttgtgc gacattgctt caatccgttg     60
attgtcgagc ttgcggaaaa aacattgaaa gagtttgggg aggacctgaa aatcgaaaca    120
aacaaattt                                                            129

<210> SEQ ID NO 2
<211> LENGTH: 184
<212> TYPE: DNA
<213> ORGANISM: Artificial Sequence
<220> FEATURE:
<223> OTHER INFORMATION: Synthetic- PA 3' packaging signal

<400> SEQUENCE: 2
cttgaacctg ggacctttga tcttgggggg ctatatgaag caattgagga gtgcctgatt     60
aatgatccct gggtttttgct taatgcttct tggttcaact ccttccttac acatgcattg   120
agttagttgt ggcagtgcta ctatttgcta tccatactgt ccaaaaaagt accttgtttc    180
tact                                                                 184
```

<210> SEQ ID NO 3
<211> LENGTH: 173
<212> TYPE: DNA
<213> ORGANISM: Artificial Sequence
<220> FEATURE:
<223> OTHER INFORMATION: Synthetic- NA 5' packaging signal

<400> SEQUENCE: 3

```
agcgaaagca ggggtttaaa ttgaatccaa atcagaaaat aacaaccatt ggatcaatct      60
gtctggtagt cggactaatt agcctaatat tgcaaatagg gaatataatc tcaatttgga     120
ttagccattc aattcaaact ggaagtcaaa accatactgg aatttgcaac caa            173
```

<210> SEQ ID NO 4
<211> LENGTH: 209
<212> TYPE: DNA
<213> ORGANISM: Artificial Sequence
<220> FEATURE:
<223> OTHER INFORMATION: Synthetic- NA 3' packaging signal

<400> SEQUENCE: 4

```
tgagctaaca gggctagact gtatgaggcc gtgcttctgg gttgaattaa tcaggggacg      60
acctaaagaa aaaacaatct ggactagtgc gagcagcatt tcttttgtg gcgtgaatag      120
tgatactgta gattggtctt ggccagacgg tgctgagttg ccattcagca ttgacaagta     180
gtctgttcaa aaaactcctt gtttctact                                        209
```

<210> SEQ ID NO 5
<211> LENGTH: 146
<212> TYPE: DNA
<213> ORGANISM: Artificial Sequence
<220> FEATURE:
<223> OTHER INFORMATION: Synthetic- PB1 5' packaging signal

<400> SEQUENCE: 5

```
agcgaaagca ggcaaaccat ttgattggtt gtcaatccga ccttactttt cttaaaagtg      60
ccagcacaaa ttgctataag cacaactttc ccttatactg gagaccctcc ttacagcctt     120
gggacaggaa caggatacac cttgga                                           146
```

<210> SEQ ID NO 6
<211> LENGTH: 153
<212> TYPE: DNA
<213> ORGANISM: Artificial Sequence
<220> FEATURE:
<223> OTHER INFORMATION: Synthetic- PB1 3' packaging signal

<400> SEQUENCE: 6

```
cccgaattga tgcacggatt gatttcgaat ctggaaggat aaagaaagaa gagttcactg      60
agatcatgaa gatctgttcc accattgaag agctcagacg gcaaaaatag tgaatttagc     120
ttgtccttca tgaaaaaatg ccttgtttct act                                   153
```

<210> SEQ ID NO 7
<211> LENGTH: 152
<212> TYPE: DNA
<213> ORGANISM: Artificial Sequence
<220> FEATURE:
<223> OTHER INFORMATION: Synthetic- PB2 5' packaging signal

<400> SEQUENCE: 7

```
agcgaaagca ggtcaattat attcaatttg gaaagaataa agaactaag aaatctattg       60
tcgcagtctc gcacccgcga gatactcaca aaaaccaccg tggaccattt ggccataatc     120
```
aagaagtaca catcaggaag acaggagaag aa                                       152

<210> SEQ ID NO 8
<211> LENGTH: 163
<212> TYPE: DNA
<213> ORGANISM: Artificial Sequence
<220> FEATURE:
<223> OTHER INFORMATION: Synthetic- PB2 3' packaging signal

<400> SEQUENCE: 8
aaaggagaga aggctaatgt gctaattggg caaggagacg tggtgttggt aatgaaacgg           60
aaacgggact ctagcatact tactgacagc cagacagcga ccaaaagaat tcggatggcc         120
atcaattagt gtcgaatagt ttaaaaacga ccttgtttct act                           163

<210> SEQ ID NO 9
<211> LENGTH: 1030
<212> TYPE: DNA
<213> ORGANISM: Artificial Sequence
<220> FEATURE:
<223> OTHER INFORMATION: Synthetic- mCherry with PB1 packaging signals
      (A/Puerto Rico/8/1934)
<220> FEATURE:
<221> NAME/KEY: misc_feature
<222> LOCATION: (1)..(146)
<223> OTHER INFORMATION: PB1 5' packaging signal
<220> FEATURE:
<221> NAME/KEY: misc_feature
<222> LOCATION: (147)..(152)
<223> OTHER INFORMATION: EcoRV site
<220> FEATURE:
<221> NAME/KEY: misc_feature
<222> LOCATION: (153)..(158)
<223> OTHER INFORMATION: Kozak sequence
<220> FEATURE:
<221> NAME/KEY: misc_feature
<222> LOCATION: (159)..(869)
<223> OTHER INFORMATION: Open reading frame of mCherry
<220> FEATURE:
<221> NAME/KEY: misc_feature
<222> LOCATION: (870)..(877)
<223> OTHER INFORMATION: PmeI site
<220> FEATURE:
<221> NAME/KEY: misc_feature
<222> LOCATION: (878)..(1030)
<223> OTHER INFORMATION: PB1 3' packaging signal

<400> SEQUENCE: 9
agcgaaagca ggcaaaccat ttgattggtt gtcaatccga ccttactttt cttaaaagtg          60
ccagcacaaa ttgctataag cacaactttc ccttatactg gagaccctcc ttacagcctt        120
gggacaggaa caggatacac cttggagata tcgccaccat ggtctcaaaa ggggaagaag        180
acaatatggc tatcattaag gaatttatgc gatttaaagt tcacatggaa ggaagtgtca        240
atggccatga gtttgagatt gagggagaag gcgaaggaag accatatgag gggactcaga        300
ctgctaaatt aaaagtgaca aagggaggtc ccttaccatt tgcatgggac attctttctc        360
cccagttcat gtatggatcc aaagcatatg ttaagcatcc tgctgatatt cccgattatt        420
tgaaactctc atttccagaa ggtttcaaat gggagagagt catgaacttt gaagatggag        480
gagttgttac tgtcacccaa gattcttctc tccaggatgg ggaatttatt tacaaagtca        540
agctccgagg aacaaatttc ccaagtgatg gaccagtcat gcaaaagaag acaatgggat        600
gggaagcaag ctcagaacgg atgtatcctg aagatggtgc tcttaaaggc gagataaaac        660
aaagacttaa gcttaaagac ggaggacatt atgatgcaga agtaaagacc acttacaagg        720
ctaagaaacc agtacaactg cccggagctt ataatgtcaa tattaaattg gatatcacca        780

```
gtcacaatga agactacact attgttgaac aatatgaaag agctgaaggt agacatagta    840
ctggtggaat ggatgaactt tataaatgag tttaaacccc gaattgatgc acggattgat    900
ttcgaatctg gaaggataaa gaaagaagag ttcactgaga tcatgaagat ctgttccacc    960
attgaagagc tcagacggca aaaatagtga atttagcttg tccttcatga aaaatgcct    1020 tgtttctact                                                          1030
```

<210> SEQ ID NO 10
<211> LENGTH: 1053
<212> TYPE: DNA
<213> ORGANISM: Artificial Sequence
<220> FEATURE:
<223> OTHER INFORMATION: Synthetic- sfGFP with PB2 packaging signals
      (A/Puerto Rico/8/1934)
<220> FEATURE:
<221> NAME/KEY: misc_feature
<222> LOCATION: (1)..(152)
<223> OTHER INFORMATION: PB2 5' packaging signal.
<220> FEATURE:
<221> NAME/KEY: misc_feature
<222> LOCATION: (153)..(158)
<223> OTHER INFORMATION: NheI site
<220> FEATURE:
<221> NAME/KEY: misc_feature
<222> LOCATION: (159)..(164)
<223> OTHER INFORMATION: Kozak sequence
<220> FEATURE:
<221> NAME/KEY: misc_feature
<222> LOCATION: (165)..(884)
<223> OTHER INFORMATION: Open reading frame of sfGFP
<220> FEATURE:
<221> NAME/KEY: misc_feature
<222> LOCATION: (885)..(890)
<223> OTHER INFORMATION: XhoI site
<220> FEATURE:
<221> NAME/KEY: misc_feature
<222> LOCATION: (891)..(1053)
<223> OTHER INFORMATION: PB2 3' packaging signal

<400> SEQUENCE: 10
agcgaaagca ggtcaattat attcaatttg gaaagaataa aagaactaag aaatctattg 60
tcgcagtctc gcacccgcga gatactcaca aaaaccaccg tggaccattt ggccataatc 120
aagaagtaca catcaggaag acaggagaag aagctagcgc caccatggtc tcaaaaggag 180
aagaattatt cactggtgtg gtcccaattc ttgttgaact tgatggagac gtcaatggac 240
ataagttttc agtgagaggg gaaggtgagg gcgatgcaac taatggaaaa ttaacactca 300
aatttatttg tactactggg aagctgcccg taccatggcc cactctcgtc accacgctta 360
cttacggggt tcagtgcttc tccaggtacc ccgatcatat gaaacaacat gacttcttca 420
aatcagctat gccagaaggc tatgttcagg agagaaccat ttcattcaag gatgatggca 480
cctataagac cagagccgag gtcaagtttg aaggagatac tcttgtcaat agaattgagc 540
ttaaagggat tgattttaag gaagatggta atattcttgg ccataaattg gagtataatt 600
tcaacagcca taatgtatac atcaccgctg ataaacagaa gaatggcatt aaagcaaatt 660
ttaaaattag gcataatgtc gaggatggaa gtgttcaact tgctgaccat tatcagcaga 720
acacacccat tggagatgga ccagtccttc ttcctgataa ccattaccta tcaacccaat 780
ccgtcttgag taaagaccct aatgagaaga gagaccacat ggttctcctt gaatttgtaa 840
ctgctgctgg aattactctc ggaatggatg aactttataa atgactcgag aaaggagaga 900
aggctaatgt gctaattggg caaggagacg tggtgttggt aatgaaacgg aaacgggact 960
ctagcatact tactgacagc cagacagcga ccaaaagaat tcggatggcc atcaattagt 1020
gtcgaatagt ttaaaaacga ccttgtttct act                                          1053

<210> SEQ ID NO 11
<211> LENGTH: 2676
<212> TYPE: DNA
<213> ORGANISM: Artificial Sequence
<220> FEATURE:
<223> OTHER INFORMATION: Synthetic- PB1 with NA packaging signals
      (A/Puerto Rico/8/1934)
<220> FEATURE:
<221> NAME/KEY: misc_feature
<222> LOCATION: (1)..(173)
<223> OTHER INFORMATION: NA 5' packaging signal
<220> FEATURE:
<221> NAME/KEY: misc_feature
<222> LOCATION: (174)..(179)
<223> OTHER INFORMATION: EcoRV site
<220> FEATURE:
<221> NAME/KEY: misc_feature
<222> LOCATION: (180)..(185)
<223> OTHER INFORMATION: Kozak sequence
<220> FEATURE:
<221> NAME/KEY: misc_feature
<222> LOCATION: (186)..(2459)
<223> OTHER INFORMATION: Open reading frame of PB1
<220> FEATURE:
<221> NAME/KEY: misc_feature
<222> LOCATION: (186)..(260)
<223> OTHER INFORMATION: Region of the PB1 open reading frame that
      contains silent mutations to disrupt the naturally encoded
      packaging signals
<220> FEATURE:
<221> NAME/KEY: misc_feature
<222> LOCATION: (2378)..(2459)
<223> OTHER INFORMATION: Region of the PB1 open reading frame that
      contains silent mutations to disrupt the naturally encoded
      packaging signals
<220> FEATURE:
<221> NAME/KEY: misc_feature
<222> LOCATION: (2460)..(2467)
<223> OTHER INFORMATION: PmeI site
<220> FEATURE:
<221> NAME/KEY: misc_feature
<222> LOCATION: (2468)..(2676)
<223> OTHER INFORMATION: NA 3' packaging signal

<400> SEQUENCE: 11
agcgaaagca ggggtttaaa ttgaatccaa atcagaaaat aacaaccatt ggatcaatct    60
gtctggtagt cggactaatt agcctaatat tgcaatagg gaatataatc tcaatttgga   120
ttagccattc aattcaaact ggaagtcaaa accatactgg aatttgcaac caagatatcg   180
ccaccatgga cgtgaaccct actttgcttt tcctgaaagt acctgcccag aatgctattt   240
ccactacatt tccatacacc ggagaccctc cttacagcca tgggacagga acaggataca   300
ccatggatac tgtcaacagg acacatcagt actcagaaaa gggaagatgg acaacaaaca   360
ccgaaactgg agcaccgcaa ctcaacccga ttgatgggcc actgccagaa gacaatgaac   420
caagtggtta tgcccaaaca gattgtgtat tggaagcaat gctttccctt gaggaatccc   480
atcctggtat ttttgaaaac tcgtgtattg aaacgatgga ggttgttcag caaacacgag   540
tagacaagct gacacaaggc cgacagacct atgactggac tctaaataga accaacctg   600 ctgcaacagc attggccaac acaatagaag tgttcagatc aaatggcctc acggccaatg   660
agtctggaag gctcatagac ttccttaagg atgtaatgga gtcaatgaaa aagaagaaa   720 tggggatcac aactcatttt cagagaaaga cagggtgag agacaatatg actaagaaaa   780
tgataacaca gagaacaata ggtaaaaaga gcagagatt gaacaaaagg agttatctaa   840
ttagagcatt gacctgaac acaatgacca agatgctga gagagggaag ctaaaacgga   900

```
gagcaattgc aacccagggg atgcaaataa gggggttgtg tactttgtt gagacactgg      960 caaggagtat atgtgagaaa cttgaacaat cagggttgcc agttggaggc aatgagaaga    1020
aagcaaagtt ggcaaatgtt gtaaggaaga tgatgaccaa ttctcaggac accgaacttt    1080 cttttcaccat cactggagat aacaccaaat ggaacgaaaa tcagaatcct cggatgtttt    1140
tggccatgat cacatatatg acaagaaatc agcccgaatg gttcagaaat gttctaagta    1200
ttgctccaat aatgttctca aacaaaatgg cgagactggg aaaagggtat atgtttgaga    1260
gcaagagtat gaaacttaga actcaaatac ctgcagaaat gctagcaagc atcgatttga    1320
aatatttcaa tgattcaaca agaagaaga ttgaaaaaat ccgaccgctc ttaatagagg      1380
ggactgcatc attgagccct ggaatgatga tgggcatgtt caatatgtta agcactgtat    1440
taggcgtctc catcctgaat cttggacaaa agagatacac caagactact tactggtggg    1500
atggtcttca atcctctgac gattttgctc tgattgtgaa tgcacccaat catgaaggga    1560
ttcaagccgg agtcgacagg ttttatcgaa cctgtaagct acttggaatc aatatgagca    1620
agaaaaagtc ttacataaac agaacaggta catttgaatt cacaagtttt ttctatcgtt    1680
atgggtttgt tgccaatttc agcatggagc tccccagttt tgggggtgtct gggatcaacg    1740 agtcagcgga catgagtatt ggagttactg tcatcaaaaa caatatgata aacaatgatc    1800
ttggtccagc aacagctcaa atggcccttc agttgttcat caaagattac aggtacacgt    1860
accgatgcca tagaggtgac acacaaatac aaacccgaag atcatttgaa ataaagaaac    1920
tgtgggagca accccgttcc aaagctggac tgctggtctc cgacggaggc ccaaatttat    1980
acaacattag aaatctccac attcctgaag tctgcctaaa atgggaattg atggatgagg    2040
attaccaggg gcgtttatgc aacccactga acccatttgt cagccataaa gaaattgaat    2100
caatgaacaa tgcagtgatg atgccagcac atggtccagc caaaaacatg gagtatgatg    2160
ctgttgcaac aacacactcc tggatcccca aagaaatcg atccatcttg aatacaagtc    2220
aaagaggagt acttgaagat gaacaaatgt accaaaggtg ctgcaattta tttgaaaaat    2280
tcttccccag cagttcatac agaagaccag tcgggatatc cagtatggtg gaggctatgg    2340
tttccagagc ccgaattgat gcacggattg atttcgaatc aggcagaatc aagaaggagg    2400
aatttacaga gattatgaaa atatgctcaa ccatagagga acttcgaagg caaaaatagg    2460
tttaaactga gctaacaggg ctagactgta tgaggccgtg cttctgggtt gaattaatca    2520
ggggacgacc taaagaaaaa acaatctgga ctagtgcgag cagcatttct ttttgtggcg    2580
tgaatagtga tactgtagat tggtcttggc cagacggtgc tgagttgcca ttcagcattg    2640
acaagtagtc tgttcaaaaa actccttgtt tctact                             2676
```

<210> SEQ ID NO 12  
<211> LENGTH: 2613  
<212> TYPE: DNA  
<213> ORGANISM: Artificial Sequence  
<220> FEATURE:  
<223> OTHER INFORMATION: Synthetic- PB2 with PA packaging signals (A/Puerto Rico/8/1934)  
<220> FEATURE:  
<221> NAME/KEY: misc_feature  
<222> LOCATION: (1)..(129)  
<223> OTHER INFORMATION: PA 5' packaging signal  
<220> FEATURE:  
<221> NAME/KEY: misc_feature  
<222> LOCATION: (130)..(135)  
<223> OTHER INFORMATION: EcoRV site  
<220> FEATURE:  
<221> NAME/KEY: misc_feature

```
<222> LOCATION: (136)..(141)
<223> OTHER INFORMATION: Kozak sequence
<220> FEATURE:
<221> NAME/KEY: misc_feature
<222> LOCATION: (142)..(2421)
<223> OTHER INFORMATION: Open reading frame of PB2
<220> FEATURE:
<221> NAME/KEY: misc_feature
<222> LOCATION: (142)..(171)
<223> OTHER INFORMATION: Region of the PB2 open reading frame that
      contains silent mutations to disrupt the naturally encoded
      packaging signals
<220> FEATURE:
<221> NAME/KEY: misc_feature
<222> LOCATION: (2336)..(2421)
<223> OTHER INFORMATION: Region of the PB2 open reading frame that
      contains silent mutations to disrupt the naturally encoded
      packaging signals
<220> FEATURE:
<221> NAME/KEY: misc_feature
<222> LOCATION: (2422)..(2429)
<223> OTHER INFORMATION: PMeI site
<220> FEATURE:
<221> NAME/KEY: misc_feature
<222> LOCATION: (2430)..(2613)
<223> OTHER INFORMATION: PA 3' packaging signal

<400> SEQUENCE: 12
agcgaaagca ggtactgatc caaattggaa gattttgtgc gacattgctt caatccgttg      60
attgtcgagc ttgcggaaaa aacattgaaa gagtttgggg aggacctgaa atcgaaaca     120 aacaaatttg atatcgccac catggagcgg atcaaggagt tgcggaactt gatgtcgcag    180
tctcgcaccc gcgagatact cacaaaaacc accgtggacc atatggccat aatcaagaag    240
tacacatcag gaagacagga gaagaaccca gcacttagga tgaaatggat gatggcaatg    300
aaatatccaa ttacagcaga caagaggata acggaaatga tccctgagag aaatgagcaa    360
ggacaaactt tatggagtaa atgaatgat gcaggatcag accgagtgat ggtatcacct    420
ctggctgtga catggtggaa taggaatgga ccaataacaa atacagttca ttatccaaaa    480
atctacaaaa cttattttga aagagtcgaa aggctaaagc atggaacctt tggccctgtc    540
cattttagaa accaagtcaa atacgtcgg agagttgaca taaatcctgg tcatgcagat    600
ctcagtgcca aggaggcaca ggatgtaatc atggaagttg ttttccctaa cgaagtggga    660
gccaggatac taacatcgga atcgcaacta acgataacca agagaagaa agaagaactc    720 caggattgca aaatttctcc tttgatggtt gcatacatgt ggagagaga actggtccgc    780 aaaacgagat tcctcccagt ggctggtgga caagcagtg tgtacattga agtgttgcat    840
ttgactcaag gaacatgctg ggaacagatg tatactccag gagggaagt gaggaatgat    900 gatgttgatc aaagcttgat tattgctgct aggaacatag tgagaagagc tgcagtatca    960
gcagatccac tagcatcttt attggagatg tgccacagca cacagattgg tggaattagg    1020
atggtagaca tccttaggca gaacccaaca gaagagcaag ccgtggatat atgcaaggct    1080
gcaatgggac tgagaattag ctcatccttc agttttggtg gattcacatt taagagaaca    1140
agcggatcat cagtcaagag agaggaagag gtgcttacgg gcaatcttca acattgaag    1200 ataagagtgc atgagggata tgaagagttc acaatggttg ggagaagagc aacagccata    1260
ctcagaaaag caaccaggag attgattcag ctgatagtg gtgggagaga cgaacagtcg    1320
attgccgaag caataattgt ggccatggta ttttcacaag aggattgtat gataaaagca    1380
gtcagaggtg atctgaattt cgtcaatagg gcgaatcagc gattgaatcc tatgcatcaa    1440
cttttaagac atttttcagaa ggatgcgaaa gtgctttttc aaaattgggg agttgaacct    1500
```

```
atcgacaatg tgatgggaat gattgggata ttgccagaca tgactccaag catcgagatg   1560
tcaatgagag gagtgagaat cagcaaaatg ggtgtagatg agtactccag cacggagagg   1620
gtagtggtga gcattgaccg ttttttgaga atccgggacc aacgaggaaa tgtactactg   1680
tctcccgagg aggtcagtga acacagggga acagagaaac tgacaataac ttactcatcg   1740
tcaatgatgt gggagattaa tggtcctgaa tcagtgttgg tcaataccta tcaatggatc   1800
atcagaaact gggaaactgt taaaattcag tggtcccaga accctacaat gctatacaat   1860
aaaatggaat ttgaaccatt tcagtcttta gtacctaagg ccattagagg ccaatacagt   1920
gggtttgtaa gaactctgtt ccaacaaatg agggatgtgc ttgggacatt tgataccgca   1980
cagataataa aacttcttcc cttcgcagcc gctccaccaa agcaaagtag aatgcagttc   2040
tcctcattta ctgtgaatgt gaggggatca ggaatgagaa tacttgtaag ggcaattct    2100 cctgtattca actataacaa ggccacgaag agactcacag ttctcggaaa ggatgctggc   2160
actttaactg aagacccaga tgaaggcaca gctggagtgg agtccgctgt tctgaggga   2220 ttcctcattc tgggcaaaga agacaagaga tatgggccag cactaagcat caatgaactg   2280
agcaaccttg cgaaggaga gaaggctaat gtgctaattg ggcaaggaga cgtggtacta   2340
gtgatgaaga gaaagagaga tagctctatc ttgacggatt cacaaacggc aactaagagg   2400
atccgtatgg ctattaacta ggtttaaacc ttgaacctgg gacctttgat cttgggggc    2460 tatatgaagc aattgaggag tgcctgatta atgatccctg ggttttgctt aatgcttctt   2520
ggttcaactc cttccttaca catgcattga gttagttgtg gcagtgctac tatttgctat   2580
ccatactgtc caaaaaagta ccttgtttct act                                 2613
```

```
<210> SEQ ID NO 13
<211> LENGTH: 1053
<212> TYPE: DNA
<213> ORGANISM: Artificial Sequence
<220> FEATURE:
<223> OTHER INFORMATION: Synthetic- sfGFP with PB2 packaging signals
      (A/Wyoming/03/2003)
<220> FEATURE:
<221> NAME/KEY: misc_feature
<222> LOCATION: (1)..(152)
<223> OTHER INFORMATION: PB2 5' packaging signal
<220> FEATURE:
<221> NAME/KEY: misc_feature
<222> LOCATION: (153)..(158)
<223> OTHER INFORMATION: NheI site
<220> FEATURE:
<221> NAME/KEY: misc_feature
<222> LOCATION: (159)..(164)
<223> OTHER INFORMATION: Kozak sequence
<220> FEATURE:
<221> NAME/KEY: misc_feature
<222> LOCATION: (165)..(884)
<223> OTHER INFORMATION: Open reading frame of sfGFP
<220> FEATURE:
<221> NAME/KEY: misc_feature
<222> LOCATION: (885)..(890)
<223> OTHER INFORMATION: XhoI site
<220> FEATURE:
<221> NAME/KEY: misc_feature
<222> LOCATION: (891)..(1053)
<223> OTHER INFORMATION: PB2 3' packaging signal

<400> SEQUENCE: 13
agcgaaagca ggtcaattat attcagtttg gaaagaataa agaactacg gaacctgttg     60 tcgcagtctc gcactcgcga gatactgaca aaaaccacag tggaccattt ggccataatt    120
aagaagtaca catcggggag acaggaaaag aagctagcgc caccatggtc tcaaaaggag    180
```

```
aagaattatt cactggtgtg gtcccaattc ttgttgaact tgatggagac gtcaatggac    240
ataagttttc agtgagaggg gaaggtgagg gcgatgcaac taatgaaaaa ttaacactca    300
aatttatttg tactactggg aagctgcccg taccatggcc cactctcgtc accacgctta    360
cttacggggt tcagtgcttc tccaggtacc ccgatcatat gaaacaacat gacttcttca    420
aatcagctat gccagaaggc tatgttcagg agagaaccat ttcattcaag gatgatggca    480
cctataagac cagagccgag gtcaagtttg aaggagatac tcttgtcaat gaattgagc     540 ttaagggat tgattttaag gaagatggta atattcttgg ccataaattg gagtataatt     600
tcaacagcca taatgtatac atcaccgctg ataaacagaa gaatggcatt aaagcaaatt    660
ttaaaattag gcataatgtc gaggatggaa gtgttcaact tgctgaccat tatcagcaga    720
acacacccat tggagatgga ccagtccttc ttcctgataa ccattaccta tcaacccaat    780
ccgtcttgag taaagaccct aatgagaaga gagaccacat ggttctcctt gaatttgtaa    840
ctgctgctgg aattactctc ggaatggatg aactttataa atgactcgag aaagggaaa     900 aggctaatgt gctaatcggg caaggagacg tggtgttggt aatgaaacga aaacgggact    960
ctagcatact tactgacagc cagacagcga ccaaaagaat tcggatggcc atcaattaat   1020
gttgaatagt ttaaaaacga ccttgtttct act                                1053
```

<210> SEQ ID NO 14
<211> LENGTH: 2613
<212> TYPE: DNA
<213> ORGANISM: Artificial Sequence
<220> FEATURE:
<223> OTHER INFORMATION: Synthetic- PB2 with PA packaging signals
      (A/Wyoming/03/2003)
<220> FEATURE:
<221> NAME/KEY: misc_feature
<222> LOCATION: (1)..(129)
<223> OTHER INFORMATION: PA 5' packaging signal
<220> FEATURE:
<221> NAME/KEY: misc_feature
<222> LOCATION: (130)..(135)
<223> OTHER INFORMATION: EcoRV site
<220> FEATURE:
<221> NAME/KEY: misc_feature
<222> LOCATION: (136)..(141)
<223> OTHER INFORMATION: Kozak sequence
<220> FEATURE:
<221> NAME/KEY: misc_feature
<222> LOCATION: (142)..(2421)
<223> OTHER INFORMATION: Open reading frame of PB2
<220> FEATURE:
<221> NAME/KEY: misc_feature
<222> LOCATION: (142)..(201)
<223> OTHER INFORMATION: Region of the PB2 open reading frame that
      contains silent mutations to disrupt the naturally encoded
      packaging signals
<220> FEATURE:
<221> NAME/KEY: misc_feature
<222> LOCATION: (1002)..(1002)
<223> OTHER INFORMATION: N is a G, C, A, or T
<220> FEATURE:
<221> NAME/KEY: misc_feature
<222> LOCATION: (1280)..(1281)
<223> OTHER INFORMATION: N is a G, C, A, or T
<220> FEATURE:
<221> NAME/KEY: misc_feature
<222> LOCATION: (2370)..(2421)
<223> OTHER INFORMATION: Region of the PB2 open reading frame that
      contains silent mutations to disrupt the naturally encoded
      packaging signals
<220> FEATURE:
<221> NAME/KEY: misc_feature
<222> LOCATION: (2422)..(2429)
<223> OTHER INFORMATION: PMeI site
<220> FEATURE:

<221> NAME/KEY: misc_feature
<222> LOCATION: (2430)..(2613)
<223> OTHER INFORMATION: PA 3' packaging signal

<400> SEQUENCE: 14

```
agcgaaagca ggtactgatt cgaattggaa gattttgtgc gacattgctt caacccgttg      60
attgtcgaac ttgcagaaaa agcattgaaa gagtttgggg aggatctgaa aattgaaaca     120
aacaaatttg atatcgccac catggaaagg atcaaagaat taagaaatct aatgagccaa     180
tccagaaccc gcgagatact gacaaaaacc acagtggacc atatggccat aattaagaag     240
tacacatcgg ggagacagga aaagaacccg tcacttagga tgaaatggat gatggcaatg     300
aaatacccaa tcactgctga caaaaggata acggaaatga ttccggagag aaatgaacaa     360
ggacaaactc tatggagtaa atgagtgat gctggatcag atcgagtgat ggtatcacct      420
ttggctgtga catggtggaa tagaaatgga cccgtgacaa gtacggtcca ttacccaaaa     480
gtatacaaga cttattttga caaagtcgaa aggttaaaac atggaacctt tggccctgtt     540
cattttagaa atcaagtcaa gatacgccga agagtagaca taaaccctgg tcatgcggac     600
ctcagtgcca aggaggcaca agatgtaatt atggaagttg ttttcccaa tgaagtggga     660
gccaggatac taacatcaga atcgcaatta acaataacta agagaaaaa agaagaactc     720
cgagattgca aaatttctcc cttgatggtt gcatacatgt tagagagaga acttgtccga     780
aaaacaagat ttctcccagt tgctggcgga acaagcagta tatacattga agttttacat     840
ttgactcaag ggacgtgttg gaacaaatg tacactccag gtggagaagt gaggaatgac      900
gatgttgacc aaagcctaat tattgcagcc aggaacatag taagaagagc cgcagtatca     960
gcagatccac tagcatcttt attggagatg tgccacagca cncaaattgg cgggacaagg    1020
atggtggaca ttcttagaca gaacccgact gaagaacaag ctgtggatat atgcaaggct    1080
gcaatgggat tgagaatcag ctcatcccttc agctttggtg ggtttacatt taaaagaaca    1140
agcgggtcat cagtcaaaaa agaggaagaa gtgcttacag caatctcca acattgaag      1200
ataagagtac atgaggggta tgaggagttc acaatggtgg ggaaagagc aacagctata    1260
ctcagaaaag caaccagaan nttggttcag ctcatagtga gtggaagaga cgaacagtca    1320
atagccgaag caataattgt ggccatggtg ttttcacaag aggattgcat gataaaagca    1380
gttagaggtg acctgaattt cgtcaacaga gcaaatcagc ggttgaaccc catgcatcag    1440
cttttaaggc attttcagaa agatgcgaaa gtgcttttc agaattgggg aattgagcac    1500
atcgacagtg taatgggaat ggttggagta ttaccagata tgactccaag cacagagatg    1560
tcaatgagag gaataagagt cagcaaaatg ggtgtggatg aatactccag tacagagagg    1620
gtggtggtta gcattgatcg ttttttgaga gttcgagacc aacgcgggaa tgtattatta    1680
tctcctgaag aggtcagtga acacaggga actgagagac tgacaataac ttattcatcg    1740
tcgatgatgt gggagattaa cggtcctgag tcggttttag tcaatactta tcaatggatc    1800
atcagaaatt gggaagctgt caaaattcaa tggtctcaga tcctgcaat gttgtacaac    1860
aaaatggaat ttgaaccatt tcaatctta gtccccaagg ccattagaag ccaatacagt    1920
gggtttgtca gaactctatt ccaacaaatg agagacgtac ttgggacatt tgacaccacc    1980
cagataataa agcttctccc ttttgcagcc gctccaccaa agcaaagcag aatgcagttc    2040
tcttcactga ctgtaaatgt gagggatca gggatgagaa tacttgtaag ggcaattct    2100
cctgtattca actacaacaa gaccactaaa agactaacaa ttctcggaaa agatgccggc    2160
actttaattg aagacccaga tgaaagcaca tccgagtgg agtccgctgt attgagaggg    2220
```

```
tttctcatta taggtaagga agacagaaga tacgggccag cattaagcat caatgaactg    2280
agtaaccttg caaaagggga aaaggctaat gtgctaatcg ggcaaggaga cgtggtgttg    2340
gtaatgaaac gaaaacggga ctctagcata cttacagatt cacaaacagc cactaagcgt    2400
ataaggatgg ccataaacta agtttaaacc tcgaacctgg gacttttgat cttggggggc    2460
tatatgaagc aattgaggag tgcctgatta atgatccctg ggttttgctc aatgcgtctt    2520
ggttcaactc cttcctgaca catgcattaa aatagttatg gcagtgctac tatttgttat    2580
ccgtactgtc caaaaagta ccttgtttct act                                  2613
```

<210> SEQ ID NO 15
<211> LENGTH: 2274
<212> TYPE: DNA
<213> ORGANISM: Artificial Sequence
<220> FEATURE:
<223> OTHER INFORMATION: Synthetic- PB1 ORF with mutations to remove the
      PB1 packaging signal (A/Puerto Rico/8/1934)
<220> FEATURE:
<221> NAME/KEY: misc_feature
<222> LOCATION: (1)..(75)
<223> OTHER INFORMATION: Mutated region
<220> FEATURE:
<221> NAME/KEY: misc_feature
<222> LOCATION: (2193)..(2274)
<223> OTHER INFORMATION: Mutated region

<400> SEQUENCE: 15

```
atggacgtga accctacttt gcttttcctg aaagtacctg cccagaatgc tatttccact     60
acatttccat acaccggaga ccctccttac agccatggga caggaacagg atacaccatg    120
gatactgtca acaggacaca tcagtactca gaaaagggaa gatggacaac aaacaccgaa    180
actggagcac cgcaactcaa cccgattgat gggccactgc cagaagacaa tgaaccaagt    240
ggttatgccc aaacagattg tgtattggaa gcaatggctt tccttgagga atcccatcct    300
ggtatttttg aaaactcgtg tattgaaacg atggaggttg ttcagcaaac acgagtagac    360
aagctgacac aaggccgaca gacctatgac tggactctaa atagaaacca acctgctgca    420
acagcattgg ccaacacaat agaagtgttc agatcaaatg gcctcacggc caatgagtct    480
ggaaggctca tagacttcct taaggatgta atggagtcaa tgaaaaaaga agaaatgggg    540
atcacaactc attttcagag aaagagacgg gtgagagaca atatgactaa gaaaatgata    600
acacagagaa caataggtaa aaagaagcag agattgaaca aaaggagtta tctaattaga    660
gcattgaccc tgaacacaat gaccaaagat gctgagagag ggaagctaaa acggagagca    720
attgcaaccc cagggatgca aataaggggg tttgtatact ttgttgagac actggcaagg    780
agtatatgtg agaaacttga acaatcaggg ttgccagttg gaggcaatga gaagaaagca    840
aagttggcaa atgttgtaag gaagatgatg accaattctc aggacaccga actttctttc    900
accatcactg gagataacac caaatggaac gaaaatcaga atcctcggat gtttttggcc    960
atgatcacat atatgacaag aaatcagccc gaatggttca gaaatgttct aagtattgct   1020
ccaataatgt tctcaaacaa aatggcgaga ctgggaaaag ggtatatgtt tgagagcaag   1080
agtatgaaac ttagaactca aatacctgca gaaatgctag caagcatcga tttgaaatat   1140
ttcaatgatt caacaagaaa gaagattgaa aaaatccgac cgctcttaat agaggggact   1200
gcatcattga gccctggaat gatgatgggc atgttcaata tgttaagcac tgtattaggc   1260
gtctccatcc tgaatcttgg acaaaagaga tacaccaaga ctacttactg gtgggatggt   1320
cttcaatcct ctgacgattt tgctctgatt gtgaatgcac ccaatcatga agggattcaa   1380
```

```
gccggagtcg acaggtttta tcgaacctgt aagctacttg aatcaatat gagcaagaaa    1440 aagtcttaca taaacagaac aggtacattt gaattcacaa gttttttcta tcgttatggg    1500
tttgttgcca atttcagcat ggagctcccc agttttgggg tgtctgggat caacgagtca    1560
gcggacatga gtattggagt tactgtcatc aaaaacaata tgataaacaa tgatcttggt    1620
ccagcaacag ctcaaatggc ccttcagttg ttcatcaaag attacaggta cacgtaccga    1680
tgccatagag gtgacacaca aatacaaacc cgaagatcat ttgaaataaa gaactgtgg    1740 gagcaaaccc gttccaaagc tggactgctg gtctccgacg gaggcccaaa tttatacaac    1800
attagaaatc tccacattcc tgaagtctgc ctaaatggg aattgatgga tgaggattac    1860
caggggcgtt tatgcaaccc actgaaccca tttgtcagcc ataaagaaat gaatcaatg    1920 aacaatgcag tgatgatgcc agcacatggt ccagccaaaa acatggagta tgatgctgtt    1980
gcaacaacac actcctggat ccccaaaaga aatcgatcca tcttgaatac aagtcaaaga    2040
ggagtacttg aagatgaaca aatgtaccaa aggtgctgca atttatttga aaaattcttc    2100
cccagcagtt catacagaag accagtcggg atatccagta tggtggaggc tatggtttcc    2160
agagcccgaa ttgatgcacg gattgatttc gaatcaggca gaatcaagaa ggaggaattt    2220
acagagatta tgaaaatatg ctcaaccata gaggaacttc gaaggcaaaa atag          2274
```

<210> SEQ ID NO 16
<211> LENGTH: 2280
<212> TYPE: DNA
<213> ORGANISM: Artificial Sequence
<220> FEATURE:
<223> OTHER INFORMATION: Synthetic- PB2 ORF with mutations to remove the PB2 packaging signal (A/Puerto Rico/8/1934)
<220> FEATURE:
<221> NAME/KEY: misc_feature
<222> LOCATION: (1)..(30)
<223> OTHER INFORMATION: Mutated region
<220> FEATURE:
<221> NAME/KEY: misc_feature
<222> LOCATION: (2195)..(2280)
<223> OTHER INFORMATION: Mutated region

<400> SEQUENCE: 16

```
atggagcgga tcaaggagtt gcggaacttg atgtcgcagt ctcgcacccg cgagatactc    60
acaaaaacca ccgtggacca tatggccata atcaagaagt acacatcagg aagacaggag    120
aagaacccag cacttaggat gaaatggatg atggcaatga aatatccaat tacagcagac    180
aagaggataa cggaaatgat tcctgagaga atgagcaag acaaactttt atggagtaaa    240
atgaatgatg caggatcaga ccgagtgatg gtatcacctc tggctgtgac atggtggaat    300
aggaatggac caataacaaa tacagttcat tatccaaaaa tctacaaaac ttattttgaa    360
agagtcgaaa ggctaaagca tggaaccttt ggccctgtcc attttagaaa ccaagtcaaa    420
atacgtcgga gagttgacat aaatcctggt catgcagatc tcagtgccaa ggaggcacag    480
gatgtaatca tggaagttgt tttccctaac gaagtgggag ccaggatact aacatcggaa    540
tcgcaactaa cgataaccaa agagaagaaa gaagaactcc aggattgcaa aatttctcct    600
ttgatggttg catacatgtt ggagagagaa ctggtccgca aaacgagatt cctcccagtg    660
gctggtggaa caagcagtgt gtacattgaa gtgttgcatt tgactcaagg aacatgctgg    720
gaacagatgt atactccagg agggaagtg aggaatgatg atgttgatca aagcttgatt    780
attgctgcta ggaacatagt gagaagagct gcagtatcag cagatccact agcatctta    840 ttggagatgt gccacagcac acagattggt ggaattagga tggtagacat ccttaggcag    900
```

```
aacccaacag aagagcaagc cgtggatata tgcaaggctg caatgggact gagaattagc    960
tcatccttca gttttggtgg attcacattt aagagaacaa gcggatcatc agtcaagaga   1020
gaggaagagg tgcttacggg caatcttcaa acattgaaga taagagtgca tgagggatat   1080
gaagagttca caatggttgg gagaagagca acagccatac tcagaaaagc aaccaggaga   1140
ttgattcagc tgatagtgag tgggagagac gaacagtcga ttgccgaagc aataattgtg   1200
gccatggtat tttcacaaga ggattgtatg ataaaagcag tcagaggtga tctgaatttc   1260
gtcaataggg cgaatcagcg attgaatcct atgcatcaac ttttaagaca ttttcagaag   1320
gatgcgaaag tgcttttca aaattgggga gttgaaccta tcgacaatgt gatgggaatg   1380
attgggatat tgccagacat gactccaagc atcgagatgt caatgagagg agtgagaatc   1440
agcaaaatgg gtgtagatga gtactccagc acggagaggg tagtggtgag cattgaccgt   1500
tttttgagaa tccgggacca acgaggaaat gtactactgt ctcccgagga ggtcagtgaa   1560
acacagggaa cagagaaact gacaataact tactcatcgt caatgatgtg ggagattaat   1620
ggtcctgaat cagtgttggt caataccat caatggatca tcagaaactg ggaaactgtt   1680
aaaattcagt ggtcccagaa ccctacaatg ctatacaata aaatggaatt tgaaccattt   1740
cagtctttag tacctaaggc cattagaggc caatacagtg ggtttgtaag aactctgttc   1800
caacaaatga gggatgtgct tgggacattt gataccgcac agataataaa acttcttccc   1860
ttcgcagccg ctccaccaaa gcaaagtaga atgcagttct cctcatttac tgtgaatgtg   1920
aggggatcag gaatgagaat acttgtaagg ggcaattctc ctgtattcaa ctataacaag   1980
gccacgaaga gactcacagt tctcggaaag gatgctggca ctttaactga agacccagat   2040
gaaggcacag ctggagtgga gtccgctgtt ctgaggggat tcctcattct gggcaaagaa   2100
gacaagagat atgggccagc actaagcatc aatgaactga gcaaccttgc gaaaggagag   2160
aaggctaatg tgctaattgg gcaaggagac gtggtactag tgatgaagag aaagagagat   2220
agctctatct tgacggattc acaaacggca actaagagga tccgtatggc tattaactag   2280
```

<210> SEQ ID NO 17
<211> LENGTH: 2280
<212> TYPE: DNA
<213> ORGANISM: Artificial Sequence
<220> FEATURE:
<223> OTHER INFORMATION: Synthetic- PB2 ORF with mutations to disrupt
       the PB2 packaging signal (A/Wyoming/03/2003)
<220> FEATURE:
<221

```
aaaaggataa cggaaatgat tccggagaga aatgaacaag acaaactct atggagtaaa      240 atgagtgatg ctggatcaga tcgagtgatg gtatcacctt tggctgtgac atggtggaat      300
agaaatggac ccgtgacaag tacggtccat tacccaaaag tatacaagac ttattttgac      360
aaagtcgaaa ggttaaaaca tggaaccttt ggccctgttc attttagaaa tcaagtcaag      420
atacgccgaa gagtagacat aaaccctggt catgcggacc tcagtgccaa ggaggcacaa      480
gatgtaatta tggaagttgt ttttcccaat gaagtgggag ccaggatact aacatcagaa      540
tcgcaattaa caataactaa agagaaaaaa gaagaactcc gagattgcaa aatttctccc      600
ttgatggttg catacatgtt agagagagaa cttgtccgaa aaacaagatt tctcccagtt      660
gctggcggaa caagcagtat atacattgaa gttttacatt tgactcaagg acgtgttgg       720 gaacaaatgt acactccagg tggagaagtg aggaatgacg atgttgacca agcctaatt       780 attgcagcca gaacatagt aagaagagcc gcagtatcag cagatccact agcatcttta       840
ttggagatgt gccacagcac ncaaattggc gggacaagga tggtggacat tcttagacag      900
aacccgactg aagaacaagc tgtggatata tgcaaggctg caatgggatt gagaatcagc      960
tcatccttca gctttggtgg gtttacattt aaaagaacaa gcgggtcatc agtcaaaaaa     1020
gaggaagaag tgcttacagg caatctccaa acattgaaga taagagtaca tgaggggtat     1080
gaggagttca aatggtggg gaaaagagca acagctatac tcagaaaagc aaccagaann     1140
ttggttcagc tcatagtgag tggaagagac gaacagtcaa tagccgaagc aataattgtg     1200
gccatggtgt tttcacaaga ggattgcatg ataaaagcag ttagaggtga cctgaatttc     1260
gtcaacagag caaatcagcg gttgaacccc atgcatcagc ttttaaggca ttttcagaaa     1320
gatgcgaaag tgcttttttca gaattgggga attgagcaca tcgacagtgt aatgggaatg     1380
gttggagtat taccagatat gactccaagc acagagatgt caatgagagg aataagagtc     1440
agcaaaatgg gtgtggatga atactccagt acagagaggg tggtggttag cattgatcgg     1500 ttttttgagag ttcgagacca acgcgggaat gtattattat ctcctgaaga ggtcagtgaa     1560
acacagggaa ctgagagact gacaataact tattcatcgt cgatgatgtg ggagattaac     1620
ggtcctgagt cggttttagt caatacttat caatggatca tcagaaattg ggaagctgtc     1680
aaaattcaat ggtctcagaa tcctgcaatg ttgtacaaca aaatggaatt tgaaccattt     1740
caatctttag tccccaaggc cattagaagc aatacagtg ggtttgtcag aactctattc     1800
caacaaatga gagacgtact tgggacattt gacaccaccc agataataaa gcttctccct     1860
tttgcagccg ctccaccaaa gcaaagcaga atgcagttct cttcactgac tgtaaatgtg     1920
aggggatcag ggatgagaat acttgtaagg gcaattctc ctgtattcaa ctacaacaag     1980
accactaaaa gactaacaat tctcggaaaa gatgccggca ctttaattga agacccagat     2040
gaaagcacat ccgagtggga gtccgctgta ttgagagggt ttctcattat aggtaaggaa     2100
gacagaagat acgggccagc attaagcatc aatgaactga gtaaccttgc aaaagggaa     2160 aaggctaatg tgctaatcgg gcaaggagac gtggtgttgg taatgaaacg aaaacgggac     2220
tctagcatac ttacagattc acaaacagcc actaagcgta taaggatggc cataaactaa     2280
```